(12) United States Patent
Zhang et al.

(10) Patent No.: US 10,709,729 B2
(45) Date of Patent: Jul. 14, 2020

(54) COMPOSITIONS AND METHODS FOR INHIBITING EXPRESSION OF ADAMTS-5 AND ADAM17

(71) Applicants: GUANGZHOU RIBOBIO CO., LTD., Guangzhou (CN); Guangzhou Institutes of Biomedicine and Health, Chinese Academy of Sciences, Guangzhou (CN)

(72) Inventors: Bill Biliang Zhang, Guangzhou (CN); Micky Daniel Tortorella, Guangzhou (CN); Zhe Wang, Guangzhou (CN); Xiuqun Yang, Guangzhou (CN); Qiuyun Wang, Guangzhou (CN)

(73) Assignees: GUANGZHOU INSTITUTES OF BIOMEDICINE AND HEALTH, CHINESE ACADEMY OF SCIENCES, Guangzhou (CN); GUANGZHOU RIBOBIO CO., LTD., Guangzhou (CN)

( * ) Notice: Subject to any disclaimer, the term of this patent is extended or adjusted under 35 U.S.C. 154(b) by 0 days.

(21) Appl. No.: 15/539,671

(22) PCT Filed: Dec. 23, 2015

(86) PCT No.: PCT/IB2015/002574
§ 371 (c)(1),
(2) Date: Jun. 23, 2017

(87) PCT Pub. No.: WO2016/103042
PCT Pub. Date: Jun. 30, 2016

(65) Prior Publication Data
US 2018/0250323 A1 Sep. 6, 2018

(30) Foreign Application Priority Data

Dec. 25, 2014 (CN) .......................... 2014 1 0827650
Dec. 25, 2014 (CN) .......................... 2014 1 0828587

(51) Int. Cl.
*A61K 31/713* (2006.01)
*C12N 15/113* (2010.01)
*A61P 19/02* (2006.01)

(52) U.S. Cl.
CPC ........ *A61K 31/713* (2013.01); *C12N 15/1137* (2013.01); *C12Y 304/24014* (2013.01); *C12Y 304/24082* (2013.01); *A61P 19/02* (2018.01); *C12N 2310/14* (2013.01); *C12N 2310/315* (2013.01); *C12N 2310/321* (2013.01); *C12N 2310/322* (2013.01); *C12N 2310/3341* (2013.01)

(58) Field of Classification Search
CPC ............ C12N 15/1137; C12N 2310/14; C12N 2310/141; A61K 31/713

USPC ...... 424/45; 435/6.1, 6.16, 91.1, 91.31, 455, 435/458; 536/23.1, 24.5; 514/44
See application file for complete search history.

(56) References Cited

U.S. PATENT DOCUMENTS

| 7,732,421 B2 * | 6/2010 | Yanni | C12N 15/1137 514/44 R |
|---|---|---|---|
| 2005/0255487 A1 * | 11/2005 | Khvorova | A61K 31/713 435/6.11 |
| 2006/0275794 A1 * | 12/2006 | Carrino | C12Q 1/6876 435/6.18 |
| 2009/0035225 A1 * | 2/2009 | Chatterton | C12N 15/1137 424/45 |
| 2010/0330155 A1 * | 12/2010 | Berry | C12N 15/111 424/450 |

FOREIGN PATENT DOCUMENTS

| CN | 101238127 A | 8/2008 |
|---|---|---|
| CN | 102181446 A | 9/2011 |
| CN | 103285026 A | 9/2013 |
| CN | 104498498 A | 4/2015 |
| CN | 104560997 A | 4/2015 |
| CN | 104560999 A | 4/2015 |

OTHER PUBLICATIONS

Du Qingfeng et al., Effects of aggrecanase-2 shRNA transfection on chondrocytes of rheumatoid arthritis patient leaded by lentivirus leaded by lentivirus, Chinese Journal of Orthopaedics, vol. 34, No. 9, pp. 936-944, Sep. 5, 2014.
International Search Report, dated Jun. 6, 2016, in International Application No. PCT/IB2015/002574.
Written Opinion, dated May 30, 2016, in International Application No. PCT/IB2015/002574.
Chu, X., et al., Protective effect of lentivirus-mediated siRNA targeting ADAMTS-5 on cartilage degradation in a rat model of osteoarthritis, International Journal of Molecular Medicine, vol. 31, No. 5, pp. 1222-1228, 2013.
Ferandes, J.C., et al., The role of cytokines in osteoarthritis pathophysiology, Biorheology, vol. 39, pp. 237-246, 2002.

(Continued)

*Primary Examiner* — Jane J Zara
(74) *Attorney, Agent, or Firm* — Knobbe, Martens, Olson & Bear, LLP

(57) ABSTRACT

Provided are siRNAs or chemically-modified siRNAs targeted against ADAMTS-5 or ADAM17 for inhibiting the expression of ADAMTS-5 or ADAM17. Use of the siRNAs for treating an ADAMTS-5 or ADAM17 associated disease, such as arthritis and other inflammation-related diseases, by injecting the siRNAs or preparations comprising the siRNAs into an articular cavity of the patient, are also provided.

7 Claims, 20 Drawing Sheets
Specification includes a Sequence Listing.

(56) References Cited

OTHER PUBLICATIONS

Jones, B.A., et al., Role of ADAM-17, p38 MAPK, Cathepsins, and the proteasome pathway in the synthesis and shedding of fractalkine/ $CX_3CL1$ in rheumatoid arthritis, Arthritis & Rheumatism, vol. 65, No. 11, pp. 2814-2825, 2013.

* cited by examiner

SEQUENCE LISTING

<160> NUMBER OF SEQ ID NOS: 198

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggauuuaugu gggcaucau                                                    19

<210> SEQ ID NO 2
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 2
augaugccca cauaaaucc                                                  19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
ggauuuaugu gggcaucaut t                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
augaugccca cauaaaucct t                                               21

<210> SEQ ID NO 5
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agctaaaaaa tgatgcccac ataaatcctc tcttgaagga tttatgtggg catcatggg     59

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatccccatg atgcccacat aaatccttca agagaggatt tatgtgggca tcatttttt     59

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcaucaugua ucugaacaa                                                  19
```

```
<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uuguucagau acaugaugc                                                19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
gcaucaugua ucugaacaat t                                             21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
uuguucagau acaugaugct t                                             21

<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agctaaaaat tgttcagata catgatgctc tcttgaagca tcatgtatct gaacaaggg    59

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gatccccttg ttcagataca tgatgcttca agagagcatc atgtatctga acaatttt     59

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<223> OTHER INFORMATION: May be 5'-Cholesterol modified
<220> FEATURE:
<221> NAME/KEY: modified_base
<222> LOCATION: (1)..(3)
<223> OTHER INFORMATION: May be 2'-O-methyl modified deoxyribonucleotide
<220> FEATURE:
<221> NAME/KEY: modified_base
<222> LOCATION: (17)..(18)
<223> OTHER INFORMATION: May be 2'-O-methyl modified deoxyribonucleotide
<220> FEATURE:
<221> NAME/KEY: modified_base
<222> LOCATION: (19)..(19)
<223> OTHER INFORMATION: May be 2'-O-methyl modified ribonucleotide
<220> FEATURE:
<223> OTHER INFORMATION: See specification as filed for detailed
      description of substitutions and preferred embodiments

<400> SEQUENCE: 13
ggauuuaugu gggcaucaut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: May 5'-phosphorylated
<220> FEATURE:
<221> NAME/KEY: modified_base
<222> LOCATION: (1)..(1)
<223> OTHER INFORMATION: May be 2'-O-methyl modified deoxyribonucleotide
<220> FEATURE:
<221> NAME/KEY: modified_base
<222> LOCATION: (2)..(2)
<223> OTHER INFORMATION: May be 2'-O-methyl modified ribonucleotide
<220> FEATURE:
<221> NAME/KEY: modified_base
<222> LOCATION: (3)..(3)
<223> OTHER INFORMATION: May be 2'-O-methyl modified deoxyribonucleotide
<220> FEATURE:
<221> NAME/KEY: modified_base
<222> LOCATION: (17)..(17)
<223> OTHER INFORMATION: May be 2'-O-methyl modified ribonucleotide
<220> FEATURE:
<221> NAME/KEY: modified_base
<222> LOCATION: (18)..(19)
<223> OTHER INFORMATION: May be 2'-O-methyl modified deoxyribonucleotide
<220> FEATURE:
<223> OTHER INFORMATION: See specification as filed for detailed
      description of substitutions and preferred embodiments

<400> SEQUENCE: 14
augaugccca cauaaaucct t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: May be 5'-Cholesterol modified
```

```
<220> FEATURE:
<221> NAME/KEY: modified_base
<222> LOCATION: (1)..(3)
<223> OTHER INFORMATION: May be 2'-O-methyl modified deoxyribonucleotide
<220> FEATURE:
<221> NAME/KEY: modified_base
<222> LOCATION: (17)..(19)
<223> OTHER INFORMATION: May be 2'-O-methyl modified deoxyribonucleotide
<220> FEATURE:
<223> OTHER INFORMATION: See specification as filed for detailed
      description of substitutions and preferred embodiments

<400> SEQUENCE: 15
gcaucaugua ucgaacaat t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: May 5'-phosphorylated
<220> FEATURE:
<221> NAME/KEY: modified_base
<222> LOCATION: (1)..(2)
<223> OTHER INFORMATION: May be 2'-O-methyl modified ribonucleotide
<220> FEATURE:
<221> NAME/KEY: modified_base
<222> LOCATION: (3)..(3)
<223> OTHER INFORMATION: May be 2'-O-methyl modified deoxyribonucleotide
<220> FEATURE:
<221> NAME/KEY: modified_base
<222> LOCATION: (17)..(17)
<223> OTHER INFORMATION: May be 2'-O-methyl modified ribonucleotide
<220> FEATURE:
<221> NAME/KEY: modified_base
<222> LOCATION: (18)..(19)
<223> OTHER INFORMATION: May be 2'-O-methyl modified deoxyribonucleotide
<220> FEATURE:
<223> OTHER INFORMATION: See specification as filed for detailed
      description of substitutions and preferred embodiments

<400> SEQUENCE: 16
uuguucagau acaugaugct t                                             21

<210> SEQ ID NO 17
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
auuuaugugg gcauc                                                    15

<210> SEQ ID NO 18
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uuaugugggc a                                                        11
```

<210> SEQ ID NO 19
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ggauuuaugu gggcaucauu cau                                              23

<210> SEQ ID NO 20
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ggauuuaugu gggcaucauu cauguga                                          27

<210> SEQ ID NO 21
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ggacuaguuu augugggcau cau                                              23

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gcuguuaugu gggcaucau                                                   19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gguuauaugu gggcaucau                                                   19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ggauuuaugu aggcaucau                                                   19

```
<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gcuguaaugu aggcaucau                                                     19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aaguccuugu gggcaucau                                                     19

<210> SEQ ID NO 27
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
auuaaugugg gcauc                                                         15

<210> SEQ ID NO 28
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
caguuuaugu gggca                                                         15

<210> SEQ ID NO 29
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gaugcccaca uaaau                                                         15

<210> SEQ ID NO 30
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugcccacaua a                                                             11

<210> SEQ ID NO 31
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
augaaugaug cccacauaaa ucc                                              23

<210> SEQ ID NO 32
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ucacaugaau gaugcccaca uaaaucc                                          27

<210> SEQ ID NO 33
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
augggucaug cccacauaaa ucc                                              23

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
augaugccca cauagauuc                                                   19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
augaugccca cauaccauc                                                   19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
augaugccca cauaccacc                                                   19

<210> SEQ ID NO 37
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
augaugccca cagaccauc                                                      19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
augaugccca cauacaucc                                                      19

<210> SEQ ID NO 39
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
acgaugccca caugca                                                         16

<210> SEQ ID NO 40
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
uuaugugggc att                                                            13

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
ggauuuaugu gggcaucauu caugugatt                                           29

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
```
ucgggaggau uuaugugggc aucau                                          25

<210> SEQ ID NO 43
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ggauuuaugu gggcaucaua guaca                                          25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
ggauuuaugu gggcaucaua guaca                                          25

<210> SEQ ID NO 45
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
ugcccacaua att                                                       13

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
ucacaugaau gaugcccaca uaaaucctt                                      29

<210> SEQ ID NO 47
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
augaugccca cauaaauccu cccga                                          25

<210> SEQ ID NO 48
<211> LENGTH: 27

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uguacuauga ugcccacaua aauccag                                              27

<210> SEQ ID NO 49
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
uguacuauga ugcccacaua aauccuu                                              27

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: misc_feature
<222> LOCATION: (17)..(20)
<223> OTHER INFORMATION: Phosphorothioate linkage between nucleotides

<400> SEQUENCE: 50
ggauuuaugu gggcaucaut t                                                    21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: misc_feature
<222> LOCATION: (17)..(20)
<223> OTHER INFORMATION: Phosphorothioate linkage between nucleotides

<400> SEQUENCE: 51
augaugccca cauaaaucct t                                                    21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<223> OTHER INFORMATION: 5'-Chol modified

<400> SEQUENCE: 52
ggauuuaugu gggcaucaut t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
augaugccca cauaaaucct t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 54
ggauuuaugu gggcaucaut t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 55
augaugccca cauaaaucct t                                              21

<210> SEQ ID NO 56
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-F modified nucleotide
<220> FEATURE:
<221> NAME/KEY: modified_base
<222> LOCATION: (17)..(19)
<223> OTHER INFORMATION: 2'-F modified nucleotide

<400> SEQUENCE: 56
ggauuuaugu gggcaucaut t                                             21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-F modified nucleotide
<220> FEATURE:
<221> NAME/KEY: modified_base
<222> LOCATION: (17)..(19)
<223> OTHER INFORMATION: 2'-F modified nucleotide

<400> SEQUENCE: 57
augaugccca cauaaaucct t                                             21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
ggauuuaugu gggcaucaut t                                             21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: LNA modified
<220> FEATURE:
<221> NAME/KEY: modified_base
<222> LOCATION: (17)..(19)
<223> OTHER INFORMATION: LNA modified
```

```
<400> SEQUENCE: 59
augaugccca cauaaaucct t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
ggauuuaugu gggcaucaut t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: UNA modified

<400> SEQUENCE: 61
augaugccca cauaaaucct t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: Indole modified nucleotide
<220> FEATURE:
<221> NAME/KEY: modified_base
<222> LOCATION: (17)..(19)
<223> OTHER INFORMATION: Indole modified nucleotide

<400> SEQUENCE: 62
ggauuuaugu gggcaucaut t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: Indole modified nucleotide
```

```
<220> FEATURE:
<221> NAME/KEY: modified_base
<222> LOCATION: (17)..(19)
<223> OTHER INFORMATION: Indole modified nucleotide

<400> SEQUENCE: 63
augaugccca cauaaaucct t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: 5-methylcytosine
<220> FEATURE:
<221> NAME/KEY: modified_base
<222> LOCATION: (17)..(17)
<223> OTHER INFORMATION: 5-methylcytosine

<400> SEQUENCE: 64
ggauuuaugu gggcaucaut t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 5-methylcytosine
<220> FEATURE:
<221> NAME/KEY: modified_base
<222> LOCATION: (18)..(19)
<223> OTHER INFORMATION: 5-methylcytosine

<400> SEQUENCE: 65
augaugccca cauaaaucct t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(6)
<223> OTHER INFORMATION: 5-ethynyluracil
<220> FEATURE:
<221> NAME/KEY: modified_base
<222> LOCATION: (16)..(16)
<223> OTHER INFORMATION: 5-ethynyluracil
<220> FEATURE:
<221> NAME/KEY: modified_base
<222> LOCATION: (19)..(19)
```

<223> OTHER INFORMATION: 5-ethynyluracil

<400> SEQUENCE: 66
ggauuuaugu gggcaucaut t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 5-ethynyluracil
<220> FEATURE:
<221> NAME/KEY: modified_base
<222> LOCATION: (5)..(5)
<223> OTHER INFORMATION: 5-ethynyluracil
<220> FEATURE:
<221> NAME/KEY: modified_base
<222> LOCATION: (17)..(17)
<223> OTHER INFORMATION: 5-ethynyluracil

<400> SEQUENCE: 67
augaugccca cauaaaucct t                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide
<220> FEATURE:
<223> OTHER INFORMATION: 3'-galactose modified

<400> SEQUENCE: 68
ggauuuaugu gggcaucaut t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

```
<400> SEQUENCE: 69
augaugccca cauaaaaucct t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 70
ggauuuaugu gggcaucaut t                                               21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-phosphorylated
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 71
augaugccca cauaaaaucct t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' may be modified by a polypeptide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 72
```
ggauuuaugu gggcaucaut t                                           21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 73
augaugccca cauaaaucct t                                           21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Cy modified
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 74
ggauuuaugu gggcaucaut t                                           21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-phosphorylated
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 75
augaugccca cauaaaucct t                                           21

```
<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: modified_base
<222> LOCATION: (17)..(19)
<223> OTHER INFORMATION: 2'-OMe modified nucleotide
<220> FEATURE:
<221> NAME/KEY: misc_feature
<222> LOCATION: (17)..(20)
<223> OTHER INFORMATION: Phosphorothioate linkage between nucleotides

<400> SEQUENCE: 76
ggauuuaugu gggcaucaut t                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: modified_base
<222> LOCATION: (17)..(19)
<223> OTHER INFORMATION: 2'-OMe modified nucleotide
<220> FEATURE:
<221> NAME/KEY: misc_feature
<222> LOCATION: (17)..(20)
<223> OTHER INFORMATION: Phosphorothioate linkage between nucleotides

<400> SEQUENCE: 77
augaugccca cauaaauccu t                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Chol modified
<220> FEATURE:
<221> NAME/KEY: modified_base
<222> LOCATION: (1)..(3)
```

```
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 78
ggauuuaugu gggcaucaut t                                          21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 79
augaugccca cauaaaucct t                                          21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Chol modified
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 80
ggauuuaugu gggcaucaut t                                          21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-phosphorylated
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
```

<222> LOCATION: (17)..(19)
<223> OTHER INFORMATION: 2'-OMe modified nucleotide

<400> SEQUENCE: 81
augaugccca cauaaaucct t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Chol modified
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: modified_base
<222> LOCATION: (17)..(19)
<223> OTHER INFORMATION: 2'-OMe modified nucleotide
<220> FEATURE:
<221> NAME/KEY: misc_feature
<222> LOCATION: (17)..(20)
<223> OTHER INFORMATION: Phosphorothioate linkage between nucleotides

<400> SEQUENCE: 82
ggauuuaugu gggcaucaut t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-phosphorylated
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: modified_base
<222> LOCATION: (17)..(19)
<223> OTHER INFORMATION: 2'-OMe modified nucleotide
<220> FEATURE:
<221> NAME/KEY: misc_feature
<222> LOCATION: (17)..(20)
<223> OTHER INFORMATION: Phosphorothioate linkage between nucleotides

<400> SEQUENCE: 83
augaugccca cauaaaucct t                                              21

<210> SEQ ID NO 84
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe modified nucleotide
<220> FEATURE:
<221> NAME/KEY: modified_base
<222> LOCATION: (3)..(3)
<223> OTHER INFORMATION: 2'-OMe modified nucleotide
<220> FEATURE:
<221> NAME/KEY: modified_base
<222> LOCATION: (14)..(14)
<223> OTHER INFORMATION: 5-methylcytosine
<220> FEATURE:
<221> NAME/KEY: modified_base
<222> LOCATION: (17)..(17)
<223> OTHER INFORMATION: 5-methylcytosine

<400> SEQUENCE: 84
ggauuuaugu gggcaucaut t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (7)..(7)
<223> OTHER INFORMATION: 5-methylcytosine
<220> FEATURE:
<221> NAME/KEY: modified_base
<222> LOCATION: (18)..(19)
<223> OTHER INFORMATION: 5-methylcytosine

<400> SEQUENCE: 85
augaugccca cauaaaucct t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Biotin modified
<220> FEATURE:
<221> NAME/KEY: modified_base
<222> LOCATION: (1)..(2)
<223> OTHER INFORMATION: 2'-OMe modified nucleotide
<220> FEATURE:
<221> NAME/KEY: modified_base
<222> LOCATION: (18)..(19)
<223> OTHER INFORMATION: 2'-OMe modified nucleotide

<400> SEQUENCE: 86
```
ggauuuaugu gggcaucaut t                                           21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'-OMe modified nucleotide
<220> FEATURE:
<221> NAME/KEY: modified_base
<222> LOCATION: (18)..(19)
<223> OTHER INFORMATION: 2'-OMe modified nucleotide

<400> SEQUENCE: 87
augaugccca cauaaaucct t                                           21

<210> SEQ ID NO 88
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-F modified nucleotide
<220> FEATURE:
<221> NAME/KEY: modified_base
<222> LOCATION: (19)..(20)
<223> OTHER INFORMATION: 2'-OMe modified nucleotide

<400> SEQUENCE: 88
ggauuuaugu gggcaucauu                                             20

<210> SEQ ID NO 89
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-F modified nucleotide
<220> FEATURE:
<221> NAME/KEY: modified_base
<222> LOCATION: (19)..(20)
<223> OTHER INFORMATION: 2'-OMe modified nucleotide

<400> SEQUENCE: 89
aaugaugccc acauaaaucc                                             20

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (1)..(1)
<223> OTHER INFORMATION: 2'-OMe modified nucleotide
<220> FEATURE:
<221> NAME/KEY: modified_base
<222> LOCATION: (2)..(2)
<223> OTHER INFORMATION: 2'-F modified nucleotide
<220> FEATURE:
<221> NAME/KEY: modified_base
<222> LOCATION: (18)..(18)
<223> OTHER INFORMATION: 2'-F modified nucleotide
<220> FEATURE:
<221> NAME/KEY: modified_base
<222> LOCATION: (19)..(19)
<223> OTHER INFORMATION: 2'-OMe modified nucleotide

<400> SEQUENCE: 90
ggauuuaugu gggcaucau                                                 19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-F modified nucleotide
<220> FEATURE:
<221> NAME/KEY: modified_base
<222> LOCATION: (2)..(2)
<223> OTHER INFORMATION: 2'-OMe modified nucleotide
<220> FEATURE:
<221> NAME/KEY: modified_base
<222> LOCATION: (18)..(18)
<223> OTHER INFORMATION: 2'-F modified nucleotide
<220> FEATURE:
<221> NAME/KEY: modified_base
<222> LOCATION: (19)..(19)
<223> OTHER INFORMATION: 2'-OMe modified nucleotide

<400> SEQUENCE: 91
augaugccca cauaaaucc                                                 19

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (8)..(8)
<223> OTHER INFORMATION: 2'-OMe modified nucleotide
<220> FEATURE:
<221> NAME/KEY: modified_base
<222> LOCATION: (14)..(14)
<223> OTHER INFORMATION: 2'-OMe modified nucleotide
<220> FEATURE:
<221> NAME/KEY: modified_base
<222> LOCATION: (17)..(17)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage between nucleotides

<400> SEQUENCE: 92
ggauuuaugu gggcaucaut t                                              21
```

```
<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe modified nucleotide
<220> FEATURE:
<221> NAME/KEY: modified_base
<222> LOCATION: (5)..(5)
<223> OTHER INFORMATION: 2'-OMe modified nucleotide
<220> FEATURE:
<221> NAME/KEY: modified_base
<222> LOCATION: (13)..(13)
<223> OTHER INFORMATION: 2'-OMe modified nucleotide
<220> FEATURE:
<221> NAME/KEY: modified_base
<222> LOCATION: (17)..(17)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage between nucleotides

<400> SEQUENCE: 93
augaugccca cauaaaucct t                                             21

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-OMe modified nucleotide
<220> FEATURE:
<221> NAME/KEY: modified_base
<222> LOCATION: (16)..(16)
<223> OTHER INFORMATION: 2'-OMe modified nucleotide
<220> FEATURE:
<221> NAME/KEY: misc_feature
<222> LOCATION: (18)..(19)
<223> OTHER INFORMATION: Phosphorothioate linkage between nucleotides

<400> SEQUENCE: 94
ggauuuaugu gggcaucau                                                19

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2'-OMe modified nucleotide
<220> FEATURE:
<221> NAME/KEY: modified_base
<222> LOCATION: (18)..(18)
<223> OTHER INFORMATION: 2'-OMe modified nucleotide
<220> FEATURE:
```

```
<221> NAME/KEY: misc_feature
<222> LOCATION: (20)..(21)
<223> OTHER INFORMATION: Phosphorothioate linkage between nucleotides

<400> SEQUENCE: 95
augaugccca cauaaauccu c                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 3'-Chol modified

<400> SEQUENCE: 96
ggauuuaugu gggcaucaut t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
augaugccca cauaaaucct t                                              21

<210> SEQ ID NO 98
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
cauguaucug a                                                         11

<210> SEQ ID NO 99
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
aucauguauc ugaac                                                     15

<210> SEQ ID NO 100
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
```
uggcaucaug uaucugaaca acg                                              23

<210> SEQ ID NO 101
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ccuggcauca uguaucugaa caacgac                                          27

<210> SEQ ID NO 102
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gcaagcauca uguaucugaa caa                                              23

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
gucacaugua ucugaacaa                                                   19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
gcgucgugua ucugaacaa                                                   19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
gcaucaugua gcugaacaa                                                   19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gucagaugua gcugaacaa                                                   19

<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
aucuggagua ucugaacaa                                                19

<210> SEQ ID NO 108
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
aucguguauc ugaac                                                    15

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gcaucaugua ccugaacaa                                                19

<210> SEQ ID NO 110
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
cugacgucau guaucugguc                                               20

<210> SEQ ID NO 111
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
ucagauacau g                                                        11

<210> SEQ ID NO 112
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
guucagauac augau                                                    15

```
<210> SEQ ID NO 113
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gucguuguuc agauacauga ugc                                               23

<210> SEQ ID NO 114
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gucguuguuc agauacauga ugccagg                                           27

<210> SEQ ID NO 115
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uugucuauuc agauacauga ugc                                               23

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
uuguucagau acaucauac                                                    19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
uuguucagau acauccaac                                                    19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
uuguucagau acauccagc                                                    19
```

```
<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uuguucagau acguccaac                                                       19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
uuguucagau acgucaugc                                                       19

<210> SEQ ID NO 121
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gcucagauac auggcac                                                         17

<210> SEQ ID NO 122
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
cauguaucug att                                                             13

<210> SEQ ID NO 123
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
ccuggcauca uguaucugaa caacgactt                                            29

<210> SEQ ID NO 124
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 124
guucguguau cugaacaa                                               18

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gucagaugua ucugaacaa                                              19

<210> SEQ ID NO 126
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
ucagauacau gtt                                                    13

<210> SEQ ID NO 127
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
gucguuguuc agauacauga ugccaggtt                                   29

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
uuguucaggu acaugaugc                                              19

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: misc_feature
```

```
<222> LOCATION: (17)..(20)
<223> OTHER INFORMATION: Phosphorothioate linkage between nucleotides

<400> SEQUENCE: 129
gcaucaugua ucgaacaat t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: misc_feature
<222> LOCATION: (17)..(20)
<223> OTHER INFORMATION: Phosphorothioate linkage between nucleotides

<400> SEQUENCE: 130
uuguucagau acaugaugct t                                             21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Chol modified

<400> SEQUENCE: 131
gcaucaugua ucgaacaat t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
uuguucagau acaugaugct t                                             21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
```

<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 133
gcaucaugua ucgaacaat t                                                    21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 134
uuguucagau acaugaugct t                                                   21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-F modified nucleotide
<220> FEATURE:
<221> NAME/KEY: modified_base
<222> LOCATION: (17)..(19)
<223> OTHER INFORMATION: 2'-F modified nucleotide

<400> SEQUENCE: 135
gcaucaugua ucugaacaat t                                                   21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-F modified nucleotide
<220> FEATURE:
<221> NAME/KEY: modified_base
<222> LOCATION: (17)..(19)
<223> OTHER INFORMATION: 2'-F modified nucleotide

<400> SEQUENCE: 136
uuguucagau acaugaugct t                    21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
gcaucaugua ucgaacaat t                     21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: LNA modified
<220> FEATURE:
<221> NAME/KEY: modified_base
<222> LOCATION: (17)..(19)
<223> OTHER INFORMATION: LNA modified

<400> SEQUENCE: 138
uuguucagau acaugaugct t                    21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 139
gcaucaugua ucgaacaat t                     21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: UNA modified

<400> SEQUENCE: 140
uuguucagau acaugaugct t                    21

```
<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: Indole modified nucleotide
<220> FEATURE:
<221> NAME/KEY: modified_base
<222> LOCATION: (17)..(19)
<223> OTHER INFORMATION: Indole modified nucleotide

<400> SEQUENCE: 141
gcaucaugua ucgaacaat t                                                  21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: Indole modified nucleotide
<220> FEATURE:
<221> NAME/KEY: modified_base
<222> LOCATION: (17)..(19)
<223> OTHER INFORMATION: Indole modified nucleotide

<400> SEQUENCE: 142
uuguucagau acaugaugct t                                                 21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 5-methylcytosine
<220> FEATURE:
<221> NAME/KEY: modified_base
<222> LOCATION: (5)..(5)
<223> OTHER INFORMATION: 5-methylcytosine
<220> FEATURE:
<221> NAME/KEY: modified_base
<222> LOCATION: (17)..(17)
<223> OTHER INFORMATION: 5-methylcytosine

<400> SEQUENCE: 143
gcaucaugua ucgaacaat t                                                  21

<210> SEQ ID NO 144
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 5-methylcytosine
<220> FEATURE:
<221> NAME/KEY: modified_base
<222> LOCATION: (19)..(19)
<223> OTHER INFORMATION: 5-methylcytosine

<400> SEQUENCE: 144
uuguucagau acaugaugct t                                            21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 5-ethynyluracil

<400> SEQUENCE: 145
gcaucaugua ucugaacaat t                                            21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 5-ethynyluracil
<220> FEATURE:
<221> NAME/KEY: modified_base
<222> LOCATION: (4)..(5)
<223> OTHER INFORMATION: 5-ethynyluracil
<220> FEATURE:
<221> NAME/KEY: modified_base
<222> LOCATION: (14)..(14)
<223> OTHER INFORMATION: 5-ethynyluracil
<220> FEATURE:
<221> NAME/KEY: modified_base
<222> LOCATION: (17)..(17)
<223> OTHER INFORMATION: 5-ethynyluracil

<400> SEQUENCE: 146
uuguucagau acaugaugct t                                            21

<210> SEQ ID NO 147
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide
<220> FEATURE:
<223> OTHER INFORMATION: 3'-galactose

<400> SEQUENCE: 147
gcaucaugua ucgaacaat t                                              21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 148
uuguucagau acaugaugct t                                             21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 149
gcaucaugua ucgaacaat t                                              21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<220> FEATURE:
<223> OTHER INFORMATION: 5'-phosphorylated
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 150
uuguucagau acaugaugct t                                              21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' may be modified by a polypeptide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 151
gcaucaugua ucgaacaat t                                               21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 152
uuguucagau acaugaugct t                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Cy modified
<220> FEATURE:
```

```
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 153
gcaucaugua ucugaacaat t                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 154
uuguucagau acaugaugct t                                              21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: modified_base
<222> LOCATION: (17)..(19)
<223> OTHER INFORMATION: 2'-OMe modified nucleotide
<220> FEATURE:
<221> NAME/KEY: misc_feature
<222> LOCATION: (17)..(20)
<223> OTHER INFORMATION: Phosphorothioate linkage between nucleotides

<400> SEQUENCE: 155
gcaucaugua ucugaacaat t                                              21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: modified_base
<222> LOCATION: (17)..(19)
<223> OTHER INFORMATION: 2'-OMe modified nucleotide
<220> FEATURE:
<221> NAME/KEY: misc_feature
<222> LOCATION: (17)..(20)
<223> OTHER INFORMATION: Phosphorothioate linkage between nucleotides

<400> SEQUENCE: 156
uuguucagau acaugaugct t                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Chol modified
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 157
gcaucaugua ucugaacaat t                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 158
uuguucagau acaugaugct t                                              21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<223> OTHER INFORMATION: 5'-Chol modified
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 159
gcaucaugua ucugaacaat t                                              21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-phosphorylated
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 160
uuguucagau acaugaugct t                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Chol modified
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: modified_base
<222> LOCATION: (17)..(19)
<223> OTHER INFORMATION: 2'-OMe modified nucleotide
<220> FEATURE:
<221> NAME/KEY: misc_feature
<222> LOCATION: (17)..(20)
<223> OTHER INFORMATION: Phosphorothioate linkage between nucleotides

<400> SEQUENCE: 161
gcaucaugua ucugaacaat t                                              21
```

```
<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-phosphorylated
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: misc_feature
<222> LOCATION: (1)..(4)
<223> OTHER INFORMATION: Phosphorothioate linkage between nucleotides
<220> FEATURE:
<221> NAME/KEY: modified_base
<222> LOCATION: (17)..(19)
<223> OTHER INFORMATION: 2'-OMe modified nucleotide
<220> FEATURE:
<221> NAME/KEY: misc_feature
<222> LOCATION: (17)..(20)
<223> OTHER INFORMATION: Phosphorothioate linkage between nucleotides

<400> SEQUENCE: 162
uuguucagau acaugaugct t                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe modified nucleotide
<220> FEATURE:
<221> NAME/KEY: modified_base
<222> LOCATION: (2)..(2)
<223> OTHER INFORMATION: 5-methylcytosine
<220> FEATURE:
<221> NAME/KEY: modified_base
<222> LOCATION: (3)..(3)
<223> OTHER INFORMATION: 2'-OMe modified nucleotide
<220> FEATURE:
<221> NAME/KEY: modified_base
<222> LOCATION: (5)..(5)
<223> OTHER INFORMATION: 5-methylcytosine
<220> FEATURE:
<221> NAME/KEY: modified_base
<222> LOCATION: (17)..(17)
<223> OTHER INFORMATION: 5-methylcytosine
<220> FEATURE:
<221> NAME/KEY: modified_base
<222> LOCATION: (18)..(18)
<223> OTHER INFORMATION: 2'-OMe modified nucleotide

<400> SEQUENCE: 163
gcaucaugua ucugaacaat t                                              21

<210> SEQ ID NO 164
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe modified nucleotide
<220> FEATURE:
<221> NAME/KEY: modified_base
<222> LOCATION: (3)..(3)
<223> OTHER INFORMATION: 2'-OMe modified nucleotide
<220> FEATURE:
<221> NAME/KEY: modified_base
<222> LOCATION: (6)..(6)
<223> OTHER INFORMATION: 5-methylcytosine
<220> FEATURE:
<221> NAME/KEY: modified_base
<222> LOCATION: (17)..(18)
<223> OTHER INFORMATION: 2'-OMe modified nucleotide
<220> FEATURE:
<221> NAME/KEY: modified_base
<222> LOCATION: (19)..(19)
<223> OTHER INFORMATION: 5-methylcytosine

<400> SEQUENCE: 164
uuguucagau acaugaugct t                                              21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-biotin modified
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (17)..(17)
<223> OTHER INFORMATION: 2'-OMe modified nucleotide
<220> FEATURE:
<221> NAME/KEY: modified_base
<222> LOCATION: (19)..(19)
<223> OTHER INFORMATION: 2'-OMe modified nucleotide

<400> SEQUENCE: 165
gcaucaugua ucugaacaat t                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe modified nucleotide
<220> FEATURE:
<221> NAME/KEY: modified_base
<222> LOCATION: (3)..(3)
<223> OTHER INFORMATION: 2'-OMe modified nucleotide
```

```
<220> FEATURE:
<221> NAME/KEY: modified_base
<222> LOCATION: (17)..(19)
<223> OTHER INFORMATION: 2'-OMe modified nucleotide

<400> SEQUENCE: 166
uuguucagau acaugaugct t                                           21

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
gcaucaugua ucugaacaa                                              19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-F modified nucleotide
<220> FEATURE:
<221> NAME/KEY: modified_base
<222> LOCATION: (17)..(19)
<223> OTHER INFORMATION: 2'-OMe modified nucleotide

<400> SEQUENCE: 168
uuguucagau acaugaugc                                              19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-F modified nucleotide
<220> FEATURE:
<221> NAME/KEY: modified_base
<222> LOCATION: (2)..(2)
<223> OTHER INFORMATION: 2'-OMe modified nucleotide
<220> FEATURE:
<221> NAME/KEY: modified_base
<222> LOCATION: (3)..(3)
<223> OTHER INFORMATION: 2'-F modified nucleotide
<220> FEATURE:
<221> NAME/KEY: modified_base
<222> LOCATION: (4)..(4)
<223> OTHER INFORMATION: 2'-OMe modified nucleotide
<220> FEATURE:
<221> NAME/KEY: modified_base
<222> LOCATION: (17)..(17)
<223> OTHER INFORMATION: 2'-F modified nucleotide
<220> FEATURE:
<221> NAME/KEY: modified_base
<222> LOCATION: (19)..(19)
<223> OTHER INFORMATION: 2'-F modified nucleotide

<400> SEQUENCE: 169
gcaucaugua ucugaacaa                                              19
```

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-F modified nucleotide
<220> FEATURE:
<221> NAME/KEY: modified_base
<222> LOCATION: (8)..(8)
<223> OTHER INFORMATION: 2'-F modified nucleotide
<220> FEATURE:
<221> NAME/KEY: modified_base
<222> LOCATION: (16)..(16)
<223> OTHER INFORMATION: 2'-F modified nucleotide
<220> FEATURE:
<221> NAME/KEY: modified_base
<222> LOCATION: (18)..(18)
<223> OTHER INFORMATION: 2'-F modified nucleotide

<400> SEQUENCE: 170
uuguucagau acaugaugc                                                  19

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe modified nucleotide
<220> FEATURE:
<221> NAME/KEY: modified_base
<222> LOCATION: (4)..(4)
<223> OTHER INFORMATION: 2'-OMe modified nucleotide
<220> FEATURE:
<221> NAME/KEY: modified_base
<222> LOCATION: (7)..(7)
<223> OTHER INFORMATION: 2'-OMe modified nucleotide
<220> FEATURE:
<221> NAME/KEY: modified_base
<222> LOCATION: (9)..(9)
<223> OTHER INFORMATION: 2'-OMe modified nucleotide
<220> FEATURE:
<221> NAME/KEY: modified_base
<222> LOCATION: (11)..(11)
<223> OTHER INFORMATION: 2'-OMe modified nucleotide
<220> FEATURE:
<221> NAME/KEY: modified_base
<222> LOCATION: (13)..(13)
<223> OTHER INFORMATION: 2'-OMe modified nucleotide
<220> FEATURE:
<221> NAME/KEY: modified_base
<222> LOCATION: (17)..(17)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage between nucleotides

<400> SEQUENCE: 171
gcaucaugua ucugaacaat t                                               21

```
<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe modified nucleotide
<220> FEATURE:
<221> NAME/KEY: modified_base
<222> LOCATION: (4)..(4)
<223> OTHER INFORMATION: 2'-OMe modified nucleotide
<220> FEATURE:
<221> NAME/KEY: modified_base
<222> LOCATION: (6)..(6)
<223> OTHER INFORMATION: 2'-OMe modified nucleotide
<220> FEATURE:
<221> NAME/KEY: modified_base
<222> LOCATION: (14)..(14)
<223> OTHER INFORMATION: 2'-OMe modified nucleotide
<220> FEATURE:
<221> NAME/KEY: modified_base
<222> LOCATION: (17)..(17)
<223> OTHER INFORMATION: 2'-OMe modified nucleotide
<220> FEATURE:
<221> NAME/KEY: modified_base
<222> LOCATION: (19)..(19)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage between nucleotides

<400> SEQUENCE: 172
uuguucagau acaugaugct t                                                   21

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-OMe modified nucleotide
<220> FEATURE:
<221> NAME/KEY: modified_base
<222> LOCATION: (17)..(17)
<223> OTHER INFORMATION: 2'-OMe modified nucleotide
<220> FEATURE:
<221> NAME/KEY: misc_feature
<222> LOCATION: (18)..(19)
<223> OTHER INFORMATION: Phosphorothioate linkage between nucleotides

<400> SEQUENCE: 173
gcaucaugua ucugaacaa                                                      19

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
```

```
<223> OTHER INFORMATION: 2'-OMe modified nucleotide
<220> FEATURE:
<221> NAME/KEY: modified_base
<222> LOCATION: (20)..(20)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage between nucleotides

<400> SEQUENCE: 174
uuguucagau acaugaugcc a                                              21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 175
agaucguuag uuagguugct t                                              21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 176
gcaaccuaac uaacgaucut t                                              21

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ctgctcccag aaacaacg                                                  18

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
attcagtgcc atcggtca                                                  18

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 179
cgagtgacaa gcctgtagcc                                                    20

<210> SEQ ID NO 180
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
tgaagaggac ctgggagtag at                                                 22

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
cagggttgct ggtggtagga                                                    20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gcataaagcg tttgcggtac                                                    20

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
acgaatctcc gaccacca                                                      18

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ggaccagaca tcaccaagc                                                     19

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 185
aguaugccac auaagcauct t                                              21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 186
gaugcuuaug uggcauacut t                                              21

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ggaccaggga gggaaata                                                  18

<210> SEQ ID NO 188
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gttgcagcag gtgtcgtt                                                  18

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 189
uucuccgaac gugucacgut t                                              21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 190
```
acgugacacg uucggagaau t                                              21

<210> SEQ ID NO 191
<211> LENGTH: 9663
<212> TYPE: DNA
<213> ORGANISM: Homo sapiens

<400> SEQUENCE: 191

```
ataaattcat tgttccacct cctcgcatct tcacagcgct cgcgctgctc tcggcgctcg      60
cagctgccga ctggggatga cggcgggcag gaggagaccg cagccgaagg gacacagaca     120
cgccgcttca ccagctcgcc tcaggctgcc cccctgcatt tttgttttaa tttttacggc     180
ttttccccct ctctttcttc ccttcctcct ggtcccagca gagccaagga aacccacaaa     240
ataagaaagg aagtgggccc cggagcttgg aacctccaca gccggcttgt ccagcgcagc     300 gcggggggcgg gaggctgcgc gcaccagttg ccagcccggt gcgcggtacc tttccttact     360
tttcttgaaa cagcgatcgt gcctgcattt ggtggttttt tggttttttgt ttttttcctt     420 ttcccgtatt tgctgaatct ccactatccg acttttttttt tttaatcttt tctttccccc     480 ccccccacc ccacctctttt ctggagcacg aatccaaaca ttttcccaag caacaaagaa      540
aagttcgcac gctggcaccg cagcccggac aggctggcgc tgctgccggg cccccctccc     600
tccgacactt gactcaatcc tgcaagcaag tgtgtgtgtg tccccatccc ccgccccgtt     660
aacttcatag caaataacaa atacccataa agtcccagtc gcgcagcccc tccccgcggg     720
cagcgcacta tgctgctcgg gtgggcgtcc ctgctgctgt gcgcgttccg cctgcccctg     780
gccgcggtcg gccccgccgc gacacctgcc caggataaag ccgggcagcc tccgactgct     840
gcagcagccg cccagccccg ccggcggcag ggggaggagg tgcaggagcg agccgagcct     900
cccggccacc cgcaccccct ggcgcagcgg cgcaggagca aggggctggt gcagaacatc     960
gaccaactct actccggcgg cggcaaggtg ggctacctcg tctacgcggg cggccggagg    1020
ttcctcttgg acctggagcg agatggttcg gtgggcattg ctggcttcgt gcccgcagga    1080
ggcgggacga gtgcgccctg cgccaccgg agccactgct tctatcgggg cacagtggac     1140
ggtagtcccc gctctctggc tgtctttgac ctctgtgggg gtctcgacgg cttcttcgcg    1200
gtcaagcacg cgcgctacac cctaaagcca ctgctgcgcg gaccctgggc ggaggaagaa    1260
aaggggcgcg tgtacgggga tgggtccgca cggatcctgc acgtctacac ccgcgagggc    1320
ttcagcttcg aggccctgcc gccgcgcgcc agctgcgaaa ccccccgcgtc cacaccggag    1380 gcccacgagc atgctccggc gcacagcaac ccgagcggac gcgcagcact ggcctcgcag    1440
ctcttggacc agtccgctct ctcgcccgct ggggctcag gaccgcagac gtggtggcgg    1500
cggcggcgcc gctccatctc ccgggcccgc caggtggagc tgcttctggt ggctgacgcg    1560
tccatggcgc ggttgtatgg ccggggcctg cagcattacc tgctgaccct ggcctccatc    1620
gccaataggc tgtacagcca tgctagcatc gagaaccaca tccgcctggc cgtggtgaag    1680
gtggtggtgc taggcgacaa ggacaagagc ctggaagtga gcaagaacgc tgccaccaca    1740
ctcaagaact tttgcaagtg gcagcaccaa cacaaccagc tgggagatga ccatgaggag    1800
cactacgatg cagctatcct gtttactcgg gaggatttat gtgggcatca ttcatgtgac    1860
accctgggaa tggcagacgt tgggaccata tgttctccag agcgcagctg tgctgtgatt    1920
gaagacgatg gcctccacgc agccttcact gtggctcacg aaatcggaca tttacttggc    1980
ctctcccatg acgattccaa attctgtgaa gagacctttg gttccacaga agataagcgc    2040
```

```
ttaatgtctt ccatccttac cagcattgat gcatctaagc cctggtccaa atgcacttca    2100
gccaccatca cagaattcct ggatgatggc catggtaact gtttgctgga cctaccacga    2160
aagcagatcc tgggccccga agaactccca ggacagacct acgatgccac ccagcagtgc    2220
aacctgacat tcgggcctga gtactccgtg tgtccggca tggatgtctg tgctcgcctg     2280
tggtgtgctg tggtacgcca gggccagatg gtctgtctga ccaagaagct gcctgcggtg    2340
gaagggacgc cttgtggaaa ggggagaatc tgcctgcagg gcaaatgtgt ggacaaaacc    2400
aagaaaaaat attattcaac gtcaagccat ggcaactggg gatcttgggg atcctggggc    2460
cagtgttctc gctcatgtgg aggaggagtg cagtttgcct atcgtcactg taataaccct    2520
gctcccagaa acaacggacg ctactgcaca gggaagaggg ccatctaccg ctcctgcagt    2580
ctcatgccct gcccacccaa tggtaaatca tttcgtcatg aacagtgtga ggccaaaaat    2640
ggctatcagt ctgatgcaaa aggagtcaaa acttttgtgg aatgggttcc caaatatgca    2700
ggtgtcctgc cagcggatgt gtgcaagctg acctgcagag ccaagggcac tggctactat    2760
gtggtatttt ctccaaaggt gaccgatggc actgaatgta ggctgtacag taattccgtc    2820
tgcgtccggg ggaagtgtgt gagaactggc tgtgacggca tcattggctc aaagctgcag    2880
tatgacaagt gcggagtatg tggaggagac aactccagct gtacaaagat tgttggaacc    2940
tttaataaga aaagtaaggg ttacactgac gtggtgagga ttcctgaagg ggcaacccac    3000
ataaaagttc gacagttcaa agccaaagac cagactagat tcactgccta tttagccctg    3060
aaaaagaaaa acgtgagta ccttatcaat ggaaagtaca tgatctccac ttcagagact     3120
atcattgaca tcaatggaac agtcatgaac tatagcggtt ggagccacag ggatgacttc    3180
ctgcatggca tgggctactc tgccacgaag gaaattctaa tagtgcagat tcttgcaaca    3240 gacccccacta aaccattaga tgtccgttat agcttttttg ttcccaagaa gtccactcca    3300
aaagtaaact ctgtcactag tcatggcagc aataaagtgg gatcacacac ttcgcagccg    3360
cagtgggtca cgggcccatg gctcgcctgc tctaggacct gtgacacagg ttggcacacc    3420
agaacggtgc agtgccagga tggaaaccgg aagttagcaa aaggatgtcc tctctcccaa    3480
aggccttctg cgtttaagca atgcttgttg aagaaatgtt agcctgtggt tatgatctta    3540
tgcacaaaga taactggagg attcagcact gatgcagtcg tggtgaacag gaggtctacc    3600
taacgcacag aaagtcatgc ttcagtgaca ttgtcaacag gagtccaatt atgggcagaa    3660
tctgctctct gtgaccaaaa gaggatgtgc actgcttcac gtgacagtgg tgaccttgca    3720
atatagaaaa acttgggagt tattgaacat cccctgggct acaagaaaac actgatgaat    3780
gtaaaatcag gggacatttg aagatggcag aactgtctcc cccttgtcac ctacctctga    3840
tagaatgtct ttaatggtat cataatcatt ttcacccata atacacagta gcttcttctt    3900
actgtttgta aatacattct cccttggtat gtcactttat atcccctggt tctattaaaa    3960
tatccatata tatttctata aaaaagtgt ttgaccaaag taggtctgca gctatttcaa     4020
cttccttccg tttccagaaa gagctgtgga tattttactg gaaattaaga acttgctgct    4080
gttttaataa gatgtagtat atttctgac tacaggagat aaaatttcag tcaaaaaacc      4140
attttgacag caagtatctt ctgagaaatt ttgaaaagta aatagatctc agtgtatcta    4200
gtcacttaaa tacatacacg ggttcattta cttaaaccttt tgactgcctg tatttttttc    4260
aggtagctag ccaaattaat gcataatttc agatgtagaa gtagggtttg cgtgtgtgtg    4320
tgtgatcata ctcaagagtc taaaaactag tttccttgtg ttggaaattt aaaaggaaaa    4380
aaatcgtatt tcactgtgtt ttcaatttat attttcacaa ctactttctc tctccagagc    4440
```

```
tttcatctga tatctcacaa tgtatgatat acgtacaaaa cacacagcaa gttttctatc    4500
atgtccaaca cattcaacac tggtatacct cctaccagca agcctttaaa atgcatttgt    4560
gtttgcttat ttgttttgtt caagggttca gtaagaccta caatgttttg tatttcttga    4620
cttattttat tagaaacatt aaagatcact tggtagttag ccacattgag aagtggttat    4680
cattgttaat gtggttaatg ccaaaaagtg gttaatatta ataagactgt ttccacacca    4740
taggcaataa tttcttaatt taaaaaatct aagtatattc ctattgtact aaatattttt    4800
cccaactgga aagcacttga ttgtacccgt aagtgtttga gtgatgacat gtgatgattt    4860
tcagaaagtt gttgttttg tttccatagc ctgtttaagt aggttgtaag tttgaatagt    4920
tagacatgga aattatttta taagcacaca cctaaagata tctttttaga tgataaaatg    4980
tacacccccc catcaccaac ctcacaactt agaaaatcta agttgtttga tttctttggg    5040
atttcttttg ttgtgaaaca ctgcaaagcc aattttctt tataaaaatt catagtaatc    5100
ctgccaaatg tgcctattgt taaagatttg catgtgaaga tcttagggaa ccactgtttg    5160
agttctacaa gctcatgaga gtttattttt attataagat gttttaata taaaagaatt    5220 atgtaactga tcactatatt acatcatttc agtgggccag gaaaatagat gtcttgctgt    5280
tttcagtatt ttcttaagaa attgctttta aaacaaataa ttgttttaca aaaccaataa    5340
ttatcctttg aattttcata gactgactt gcttttgacg tagaaattt ttttctcaat    5400 aaattatcac tttgagaaat gaggcctgta caaggctgat aacctatatg tgatggagat    5460
cacccaatgc caagggcaga aagcaaacct agttaaatag gtgagaaaaa aaataataat    5520
cccagtgcca tttgtctgtg caaagagaat taggagagag gttaatgtta cttttttcca    5580
ttttggaaat aatttaatc aagtaactca atgtgacaa aatttattt tattttttgt    5640 ggttatattc ccaacaacat taaaaaatac tcgaggcata aatgtagttg tctcctactc    5700
tgcttctctt actatactca tacatttta atatggttta tcaatgattc atgtttccct    5760
caaatagtga tggtttacac ctgtcatgga aacaatccta gagagctcag agcaattaaa    5820
ccactattcc atgcttttaa gtagttttct ccaccttttt cttatgagtc tcactagatt    5880
gactgaggaa tgtatgtcta aattcctgga gaagatgata tggattggaa actgaaattc    5940
agagaaatgg agtgttcaat agataccacg aattgtgaac aaagggaaaa ttctatacaa    6000
ctcaatctaa gtcagtccac tttgacttcg tactgtcttt cacctttcca ttgttgcatc    6060
ttgaattttt taaaatgtct agaattcagg atgctagggg ctacttcttt aaaaaaaaaa    6120
aaaaaaaaga attcgtctga aaatgctcag gtttgtaaga atctaatctc acttacataa    6180
ctaagcactc cataataagt tttattaagt acaagggag ccagaaaaaa tgacatttat    6240
ttcttctaga tcagaaaaat ttaaattaag ccctgccttg ctgtttagaa atatgtgggc    6300
attgttataa tttattcaat aaatttatgt tcctttgcct tcctgtggaa acagttttat    6360
cccactaaac taggaattag gggataaatc acaaacaaaa aaaagttgc agcactgaaa    6420 aaaagtaatt tattgttttt gcaactggta tgtgaatttg tgtgataaaa ttatttattc    6480
ttatttaaca aaaatatgtt caaatttttc tatatttaaa atgttttgct gttgtcctac    6540
tttttaattt atgcttcatg tttgtgtata aagtacactt ttcactttg tgagtttaca    6600 taatatacag cactggttgc ttttgtattt ttttacagaa agctttctgt gtgaagcagg    6660
tgtatatgta tatattcctc atgtattctt attctgatac tatcattttt ctttccaagg    6720 aaatttttaat ctgtcatgac caatagtgtt cattacttgt gcctatgata ataggttttt    6780
```

```
tacatcacat taacactatt ttttccaagt cacaaataag aaaaacactt attcaatgaa    6840
acaaggtgca agttttaaat ttgggtacac aaatagccta gaagcttcct acagacgcta    6900
agacacagcc aataatcaga tcctttcact tcatcgagaa acttggacaa gtcgatattg    6960
atgtattaga tgaaagttgt ctacacacaa cttctgaggg atacaaacga taataaaacc    7020
aaatgttgtc tgtttctcct ttagaaacac ctcctaaaat taatatcatt tagtctctag    7080
tgtctgtagg attctacaga tgagcacaaa tagattgggt ttgtataaca aatgctaata    7140
gtcataactg tttctacaaa tatggggtgt ccattaagag aatgtgatgt tttcctactg    7200
ctgttgaatc ccatggggtg attataggac ttgaaatagg cagagtcacc tctgatgaca    7260
tcagcttgcc tctgtgattt cacagtctga tcctggcaac aagacaaagc acccttggac    7320
acacagccaa tctctggttg tgatatttcc ccattgattc cttccttgtt aacaaggtca    7380
ttttaatggt tcaggtgagg acagcagcca gattcaaagt ccagaatttg tgctgttaca    7440
tagagttcac actgtcaaat aacattgaat ttaataatga tcaaattttt ctagtagtct    7500
ttggcagagt gtataatctc attggcatga ttggtgaata ttactaatct ctttataatg    7560
aaagatgctt tacaaatacc ttatatttgc taacatttca aaactactaa ataaatgaaa    7620
tagccatgtg tacagaaatg gtcatttaaa gctttaatag aaccaaattc aagacaatgt    7680
atcatttaga cacacagaaa aggaacttgt atgttttccc tattattttt ctcatttgcc    7740
aacaatctat agttttaggt tatcaaacag atagatcaac ttaactggct agtacattga    7800
aaaatcttcc taagaatcct ttgttagcat aatctataga gataatttct caaattatat    7860
catcatgatg catataaact ctataatgta taattgtgtt tcatttattt aatgtatgag    7920
aacatattga aatacaaaac catgcattag ccaaaaaatt ggaatacagg tagtgttcag    7980
atcagcaaaa cattcagtct ggtaaatgcc tgcctgggc  tatgatatca ttctcaatgc    8040
aggttttatg gaaaaactaa aagaatatgt tgttagatga tgttggtttt gaaaaaaaaa    8100
agacattaac atacacatta gttagcccag ttaattgcat tctactaata tagttgcaca    8160
ttagcaataa ttttgctgtc tctggtcttt attttgtggc ttcaactaac tggaccatgt    8220
ggactgtaaa ggtcaaatgg aaaaaacgag cagtggcccc tcatcctgta aggtactgct    8280
acatcagagt gacctaaaag tctaacactg tgaggaaaac tgtgatttgt aggaaaaaaa    8340
aaaaaaacaa ataaaaaaca gggcatgctt tttaattttt ttccactttc ctttggcaca    8400
cccaatgaac aattctaatt tttattgagg tgctaacatc tttcgtgacc gactgtcaaa    8460
tgtggtattt ttgagttact atttttctac atgattttac agtttgcaag aaagacctct    8520
aagctttgtg tcacggtagg gcacaacttg atactcaaaa tttgaaaaat aagcacatcc    8580
aatgattgtt ttgaccaaca gtggtcagtg acgtaaactg catgtgcatc tgaggacatt    8640 taagggtca  ttaaaatttg aggagcatca ggccggagta gcagactttt agatgagtca    8700
tatttcagca ttcactaagt cctcagcatt ccattcaaac tgtcgtgtat atttggcctg    8760
attttttttc aagctttgca ataatttatg ttattggtaa acacttggtg actatatctc    8820
agccttttct ttaacaactc acaatatatt agaaacacgt ctacctatac tgagagtata    8880
tttacaatag aagaacatac tgtatgtgac tttgtaaagc tagacttttg attaagaaat    8940
atataatctc tggatgctat ttttgcatta tacactcagg cacaacgtaa accttgatgg    9000
ctcatcttgc tacaattacg agttgaaaaa cactacttac gtatttgtat gacctattag    9060
tcagaggaaa tcatacatat gctttgtaaa tagactttgc agataactaa atagactgaa    9120
gaaatatgtt gcatttgata gaagcaattg cataaatatt tggtttctat attagagtct    9180
```

-continued

```
gtgagtaaag tcaagtaata aacctaagta ggtataacag atttttaaac cttgaaactt    9240
gctttgatgg tagagaaaat cattgaagat ttacatactg tatataagat gtaaaatgta    9300
cgctgcttat taccctcaat tttccagaag caatggtata taatgcagtt gaaaaaccaa    9360
aaatcttgga aaactaagac gggtcttgtt taaaatgtct ctcagctttg caaccttca     9420 aatcttaatc aactatttaa agcattactg tgtcttgtag cctgcattcc acaacagctc    9480
tgttattcag gtaaaagact tgaactgagc cgtttgggac ctatactgta atattttcat    9540
tgaggaacaa tatcctattt tgtaaagcat ttccctatgt gtgactttaa actgtaaaat    9600
taaacactgc ttttgtgggt tcagtgggca taataaatat aaattgtaaa ctaggttaaa    9660
gta                                                                 9663
```

<210> SEQ ID NO 192
<211> LENGTH: 2787
<212> TYPE: DNA
<213> ORGANISM: Rattus norvegicus

<400> SEQUENCE: 192

```
atgctactcg agtgggcgtc cttgctgctg ctactgctgc tgctgtgcgc gtcctgcctg      60
gccctggcgg ctgacaaccc tgccgcggca cctgcccagg ataaaaccag gcagcctcgg     120
gctgctgcag cggccgccca gcccgaccag cggcagtggg aggaaacaca ggagcggggc     180
catccgcaac ccttggccag gcagcgcagg agcagcgggc tggtgcagaa tatagaccaa     240
ctctactctg gcggtggcaa agtgggctac cttgtctacg cggcggccg gaggttcctg     300 ctggacctgg agagggatga cacagtgggt gctgctggtg catcgttac tgcaggagga     360 gggctgagcg catcctctgg ccacagggt cactgcttct acagaggcac tgtggacggc     420
agccctcgat ccctagctgt ctttgacctc tgtggggtc tcgatggctt cttcgcagtc     480
aagcatgcgc gctacactct gaagccgctc ttgcgtgggt cctgggcaga gtccgaacga    540
gtttacgggg atgggtcttc acgcatcctg catgtctaca cccgcgaggg cttcagcttc     600
gaggccctgc cgccacgcac cagttgcgag actccagcgt ccccgtctgg gccccaagag    660
agcccctcgg tgcacagtag ttctaggcga cgcacagaac tggcaccgca gctgctggac    720
cattcagctt tctcgccagc tgggaacgcg ggacctcaga cgtggtggag gcggaggcgc    780
cgttccatct ccagggcccg ccaggtggag ctcctcttgg tggctgactc ttccatggcc    840
aagatgtatg ggcggggcct gcagcattac ctgctgaccc tggcctctat tgccaaccgg    900
ctgtacagtc atgcaagcat cgagaaccac atccgcctgg ccgtagtgaa agtggtggtg    960
ctgaccgaca agagtctgga ggtgagcaag aacgcggcca cgaccctcaa gaacttttgc   1020
aaatggcagc accaacacaa ccagctaggt gatgaccatg aggagcacta cgatgcagcc   1080
atcctgttca ccagagagga tttatgtggg catcattcat gtgacaccct gggaatggca   1140
gacgttggga ccatatgttc tccggagcgc agctgcgctg tgattgaaga tgatggcctc   1200
catgcagctt tcactgtggc tcacgaaatt ggacatctac ttggcctctc tcacgacgat   1260
tccaaattct gtgaagagaa ttttggttct acagaagaca agcgtttaat gtcttcaatc   1320
cttaccagca ttgatgcatc caagcccctgg tccaaatgca cttcagccac gatcacagaa   1380
tttctggatg acgtcatgg taactgtttta ctagatgtac cacggaagca gattctgggc   1440
cccgaggaac tcccaggaca gacctatgat gccacccagc agtgcaactt gacatttggg   1500
cctgaatatt ctgtgtgccc tggcatggat gtctgtgcac ggctgtggtg tgctgtggtg   1560
```

```
cgccaaggcc aaatggtgtg tctgaccaag aagttgcctg ccgtggaggg cactccctgt    1620
ggtaaaggaa gaatctgcct gcaagggaaa tgtgtggaca aaactaagaa aaaatattac    1680
tcgacatcaa gccatggaaa ttgggggtcc tggggcccct ggggtcagtg ttctcgctct    1740
tgcgggggag gagtacagtt tgcctaccgc cattgcaata accccgcacc tcgaaacagt    1800
ggccgctact gcacagggaa gagggccata taccgttcct gcagtgtcat accctgccca    1860
cctaacggca aatctttccg ccacgagcag tgtgaagcca aaatggcta tcagtccgat     1920 gcaaaaggag tcaaaacatt tgtagaatgg gttcccaaat acgcaggtgt cctgccggca    1980
gacgtgtgca agcttacgtg cagagctaag ggcactggct attacgtggt cttttctcca    2040
aaggttacag atgggacaga atgtagaccc tacagcaact ccgtgtgtgt ccgaggaagg    2100
tgcgtgagaa cggggtgtga cggcatcatc ggctcaaagc tacagtatga caagtgtgga    2160
gtgtgtggag gggataactc cagttgtaca aagattatcg gaaccttcaa taaaaaaagc    2220
aagggttata ctgacgttgt gaggatccct gaaggagcaa cccacataaa agtccgacag    2280
ttcaaagcca aagaccagac tagattcact gcttacttag ccctaaagaa gaaaactggc    2340
gagtacctta tcaacggcaa gtacatgatc tccacttcag agaccatcat cgacatcaat    2400
ggtaccgtca tgaactacag tgggtggagt cacagagatg atttttttaca tgggatgggc    2460 tattcagcca caaaggaaat tctgattgtg cagatccttg caacagaccc aactaaagca    2520
ttagacgtcc gttacagctt ttttgttccc aagaagacca ctcaaaaagt gaattccgtc    2580
attagccaca gcagcaacaa agtgggacta cactccccgc agctacagtg ggtgacaggc    2640
ccctggctgg cctgctctag gacctgtgac acaggctggc acaccaggac cgtgcagtgc    2700
caggatggaa acaggaaatt agctaaggga tgcattctct ctcagaggcc ttctgcgttt    2760
aagcaatgtt tgctcaagaa atgttag                                       2787
```

<210> SEQ ID NO 193
<211> LENGTH: 8104
<212> TYPE: DNA
<213> ORGANISM: Mus musculus

<400> SEQUENCE: 193

```
gaaattgcca ttgcaggatg gcacgccgct ataaattcat tgtcccacct cctcgcatct      60
tcacagcgcc tgagccgctc tccgcgcccg tagcagccga ctggggatga tcccgggcgg     120
gaggacgcgg caacggaagg gaccgggacg cgccgcctcg ctggctctcc gcaggccgcc    180
tcctagcttt tgattttaaa catttttagg tgtttccttt gcttgctttc tttccttttc     240
ttttctcccg tctcatttct ccctgccttc gggttccagc ggagccgagg aagccctgag    300
aataagaaag gaagtgggtc ggagcttgga agctttgcag cccgccagcc ccgggcttcg    360
agggggcggg agcggacgcg caccagttgc gggccagcgc ggtcgccctt cttactctct    420
tagctcgttt gttttgatct gtttgtgcaa agatcttgtc tgcgttgggc ctctctcctt    480
ttttgtattt ggttgctctc cacctcttgg cttttactcc caccaacacc acccctttatt   540 taatttttttt tcttttattt tatttaaaat ttttcttcct ccgtctcttg gacctccatt   600
ccaaacattt tccaaaccaa caaagaaaaa gttctcacag tggcaccggt gccaggccag    660
gctggctctc tgctgcggat tccccctacc ctttcctgga cacttgactc aaccttgcac    720
gccagtgtgt agagtgtgcg gctgtggggtg ggtgggtggg agggcgagcc cccaccccc    780 gccccctgaaa cttctatagc aaaatagcaag catccagcta gactcagtcg cgcagcccct    840
cccggcgggc agcgcactat gcggctcgag tgggcgccct tgttgctgct actgctgctg    900
```

```
ctgagcgcgt cctgcctgtc cctggccgct gacagccccg ccgcggcacc tgcccaggat    960
aaaaccaggc agcctcaggc tgcagcagcg gccgccgagc cggaccagcc gcaggggggag  1020 gaaacacggg agcgaggcca tttacaaccc ttggccgggc agcgcaggag cggcgggctg  1080
gtccagaata tagaccaact ctactctggc ggtggcaaag tgggctacct tgtctacgcg  1140
ggcggccgga ggttcctgct ggacctggag agagatgaca cagtgggtgc tgctggtagc  1200
atcgttactg caggaggagg gctgagcgca tcctctggcc accggggtca ctgtttctac  1260
agaggcaccg tggacggcag ccctcgatcc ctagctgtct ttgacctctg cgggggtctc  1320
gatggcttct ttgcagtcaa gcatgcgcgc tacactctaa agccactcct gcgtgggtcc  1380
tgggcagagt atgaacgaat ttatggggat ggatcttccc gcatcctgca tgtctacaac  1440
cgcgagggct ttagcttcga ggccctgccg ccacgcgcca gttgcgagac tcctgcatcc  1500
ccatctgggc cccaagagag cccctcggtg cacagtagat ctaggagacg ctcagcgctg  1560
gccccgcagc tgctggacca ctcagctttc tcgccatctg gaacgcggg acctcagact  1620 tggtggaggc gtaggcgccg ttccatctcc agggcccgcc aggtggagct cctcttggtg  1680
gctgactcgt ccatggccag gatgtatggg cggggcctgc agcattacct gctgaccctg  1740
gcctccatcg ccaacaggct gtacagtcat gcaagcattg agaaccacat ccgcctggcg  1800
gtggtgaagg tggtggtgct gacggacaag gacacgagtc tggaggtgag caagaatgcg  1860
gccacgaccc tcaagaactt tgcaaatgg cagcaccaac ataaccagct aggggatgat  1920
cacgaagagc actacgatgc agccatcctg ttcacccgag aggatttatg tgggcatcat  1980
tcatgtgaca ccctgggaat ggcagacgtt gggaccatat gttctccgga gcgcagctgt  2040
gcagtgattg aagatgatgg cctccatgca gccttcactg tggctcatga aattgggcat  2100
ctacttggcc tttctcatga cgattccaaa ttctgtgaag agaacttcgg tactacagaa  2160
gacaagcgtt taatgtcttc aatccttacc agcatcgatg catccaagcc ctggtccaaa  2220
tgcacgtcag ccaccatcac agaattcctg gatgatggtc atggtaattg tttgctagac  2280
ctaccacgga agcagatttt gggtcccgag gaactcccag acagaccta cgatgccacc  2340 cagcagtgca acttgacatt tgggcctgag tactcggtgt gccctggcat ggatgtctgt  2400
gcgcggctgt ggtgtgctgt ggtgcgccaa ggccaaatgg tgtgtctgac caagaagctg  2460
ccggctgtga agggcactcc ctgtgggaag ggaagagtct gccttcaagg caaatgtgtg  2520
gacaaaacta agaaaaaata ttactcgaca tcaagccatg gaaattgggg gtcctggggc  2580
ccctggggtc agtgttctcg ctcatgcggg ggaggagtgc agtttgccta ccgccattgt  2640
aataaccctg cacctcgaaa cagtggccgc tactgcacag ggaagagggc catataccgt  2700
tcctgcagtg ttacaccctg cccacccaat ggtaaatctt ttcgccatga gcagtgtgaa  2760
gccaaaaatg gctatcagtc tgatgcaaaa ggagtcaaaa catttgtaga atgggttccc  2820
aaatatgcag gtgtcctgcc ggcagatgtg tgcaagctta cctgcagagc taagggcaca  2880
ggctactatg tggtctttc tccaaaggtt acggatggga ctgaatgcag gccgtacagc  2940
aactctgtgt gtgtccgagg acggtgtgtg agaactggat gtgacggcat tattggctca  3000
aagctacaat atgacaagtg tggagtgtgc ggagggggata actccagttg tacaaagatt  3060
atcggaacct tcaataaaaa aagcaagggt tatactgacg ttgtgaggat ccctgaagga  3120
gcaacccaca taaagtccg acagttcaaa gccaagacc agactagatt cactgcctac  3180
ttagccctga agaagaaaac tggcgagtac cttatcaatg gcaagtacat gatttccact  3240
```

```
tcagagacca tcatcgacat caatggtacc gtcatgaact acagtggatg gagccacaga      3300
gatgattttt tacatgggat gggctattca gccacaaaag aaatcctgat cgtgcagatc      3360
cttgccacag acccaactaa agcgctagac gtccgttaca gcttttttgt tcccaagaag      3420
accactcaaa aagtaaactc tgtcatcagc catggcagca acaaggtggg accacactct      3480
acacagctgc agtgggtgac aggtccatgg ctggcctgct ccaggacctg tgacacaggc      3540
tggcacacta ggaccgtgca gtgccaggat ggaaacagga aattagctaa aggatgcctt      3600
ctctctcaga ggccttctgc atttaagcaa tgtctgctga agaaatgtta gcctgtggtt      3660
tactctaatg cacaaaaaaa caacaggagg atcatcgcag atacagctgt ggtgaagaca      3720
aggcctaccc aaagcacaga aagtcatgcc ttcatgtcat tgtcaccacg agtcgaatta      3780
tgggcagaat ctgctctctg cgaccaaaag gtttactcta cttggtgtaa tgatggtgac      3840
cttggaataa agaaaacgtg agggtcatgg aacatccctg ggcctacaca aaggagacac      3900
acaatgatga atgtagaatc ggggacattt gaagatggca gagaagtctt gtcacctacc      3960
tcttatagaa tgtcttcaaa gacatcgtga tcatgttcag ccatgacaca cagcttattt      4020
ttactgtttg taaatgcatc cgcccttagt atgtcacttt ataaacttgg tcctattaat      4080
atatacacat gtgtaaatac aatatatata tttgaccaaa gtaggtctgc agctatttca      4140
actactattt tccagaaaga gctgaagaag atttactgga aattaagaac ttgctgctgt      4200
taaataaaac tttgtatatt gtcagcctgc aggagataac attttagtca aaaaaaaaaa      4260 aaaagaaaa aaaagaaaaa gaaaagaaaa agaaagaaac cattttgaca gcaagcacct      4320
tctgtgaagt tctaaaaagg gaaaggatct gcgtgtgtct ggtcatttaa acacatattc      4380
agttctgtgt actctagagt ttgacggtct gtatatttt caggcagcca agccaagtta      4440
ttgtatcatt tgggtgtaga aactgtgttt tcctgtgtat atgtgatcaa tatccaaggg      4500
tctaaaagtt agcttgcttg tattggaatt taaaacaaca acaacaaaaa gaaatatgtc      4560
actgtgtttt caatttgtat tttcacaact gcttcctttt ctatggctcc tggttcatat      4620
ctcacagtgt gtagggatca tagagaacac gcagagccgc aagctgtctg tcacatccag      4680
cttccgcagt aatggctcac ctctgctcag ccagggttta aaatgtgttt gtggttgctt      4740
gtttgttttt cctgagggtg ggaagatgta tgttctgtat tggctgggtc taacagtaat      4800
attaaaatca tttcgtattt agcctcatct tgaacgagca atcggatcag ttcaactaat      4860
tcaagaaacc aaactagtta gcacttaaaa gactgtttcc acaccatagg caattatctc      4920
ataatttaca aaatataagc atatgtctgc tgtattagag aatttctgct ctcagaaggc      4980
gtttgtctct accagtgagt atgtaagtga tggaatataa gtggtttcag gaagtctttt      5040
acctgcacaa gaaggtcgca cacgcttaat gataatcata atctccttta actactcact      5100
gaaaggcccc cctccgataa ttcaaataat atgacgtggt tttattccac tggcatttct      5160
tttttcttcg taaaaatctg caaagtaaat tgttttacac aaattctata gtgaccatac      5220
caaatgtgcc tactgtgaaa gatttgcata gaaggatttt gagaaatcct ctctggaatt      5280
ccactaaatg tatgagagtt tatttttatt ataggatatt ttaatataaa taactatgta      5340
attgatgact ccatatcaca ttgatttcag tgggacagaa aaagaatgca atcctactta      5400
ggtttgtttg tttgtttgtt tgttttaaga gattattttg tgaaacagac caatgccctc      5460
ccaaaccagt catcatccat tggcttctca cagcctggtc tttttacatc aagaaatgca      5520
gactatacag aacttgtagc ctatattggg tgcaggtctc caaatataga gcagggagtt      5580
catttagtca aattggtcat aagacaaaaa attaaatctc acgttgctta tttaactgta      5640
```

```
cagagagaat aaatagtata atgcaacttt ctccaatttc taaaaacaat ataagccaag    5700
tagttccaat ttgacaaaat tcttattttg ttttttgttg tggttatatt aaaaaaaata    5760
aatgaagagt aaatgtgatt atctcctact ctgcttccct ctatgatcat catagttttt    5820
tttaataata ttttcactgg gttacttttcc ctataataat cgagttttat acttcacact    5880
gaaatcatcc taaggagggt aaacggataa accactaatc tatgtctaga gggattttct    5940
ttatgtttta aaaagactat tcctacattg acagggaat gtatataaat ctcctgagga    6000
aagaaacaca gcaaactgag agtcagaaat ctgaagtgtc acagagggaa agagaaattg    6060
agtgtgggag gagaaaccga tattaaattc caattcattc agttagattc tgtgctgtgt    6120
ttgccatctt cccggttgtg tatcttgaat cgttaaagac cttggattta agatggtgaa    6180
taaaggtggg gaaacagaac aaggcagtgc tctggttaca aaatgtctaa ccttgcttgc    6240
ataaaaaaat tattccagag tgagtgtcag tgcaaaagag cccagagtga acagtacct    6300 tgatctatca gaacagcaaa tgccacctta aaacccctt attgcttgaa agtataagga    6360
catggttata gtgtatttaa cagactcaac atctattgcc ttcctgtgga aacagtttta    6420
aactaacagt tgagggatga atcacaaaca aacagaataa gaagttgcag cactgaaaac    6480
taagtaattt attgtttttg caactgccat gtgaatttct gtgatgaaat tattattct    6540 tatttaacaa aaattatgtg caaaatctta tatttgaaat gttttgctgt tgtccttttt    6600
ttaatttatg cttcttgttt gtgtataaag tgcactttgt gagtttatat aatatacagc    6660
actggtggct ttgtatttct tttttacaga aggctttctg tgtggaacag gtgtatgtgt    6720
gtatattccg catgtatttt cagtctgcca ctctcttaaa ttttaaagga acattgatca    6780
ctatgttaat aggtcattta aataccaata acattggctt tttcagatca tgagttttaa    6840
aaatgtgtat tcaatccagc aagttgcaac tggtttttaa ctagaggaca tatatacctt    6900
aggaacatct caacagaagc taagacacaa tggagaacag ggtttgaaac aggcatagca    6960
cacaggaggc tgaaggagga agattatgaa cttaagagtt gtctgggagc catagcaggc    7020
ccctagtttg gtggaagaaa tagaatcagt ttcagtcaca tcactgataa ttatatacaa    7080
ggagacttaa atttattata tgcatgttat agacacataa cttctaagtg attaaagaat    7140
gataaataca aactcttaca gctttagaaa cagcttccca caaaaacagt gtctgagcct    7200
ctgctgtctg tagagattct agagatgatc tcaaatgaaa gtggatttgt gtatttctaa    7260
taccagtcat aaccttgtct atgggtgtaa gtgcacataa caaagtaaga cttttttacta    7320 ctactatcag accagagtgg taggacatgg gacaagcagg aacaactctg gtaacaacag    7380
ctcatttgtg agtgagactg tgcggtccag gtctagaaat aaagtcaagc actcttggcc    7440
ccactgtata agtcattggg tcaagccctg gctccgatgt tcctccatta ataacttcct    7500
tgttagcaaa ttaacaaggt cagtcagtgc aaccagcagg gaacataggc aggttcagaa    7560
atccagggtg tgcactatga ctgcagctca ttgttagaaa tatgatgaat acaatgctta    7620
attctactct gagttgagaa ccctgcaaaa cagccatact gtgctaatac cactcatcta    7680 tttcacactga aacatgggac cgtacaaatg cattacattt tttattattt catggctaca    7740
aaataaaaga aataaccaca agagcaaaat aggtcaaagc agatgcaaaa tcatattaag    7800
gaagttttat cattaaaaca cagagaaaag gcacttgtat ggtttctgta ttattatttt    7860
ctttggccaa cagtctacag ttgcaaagaa tcaaacaaat agatcagcct aaccgaatag    7920
tttggtaaaa atgtggtaat aaacccttat taatgtgaaa tataggcatg gcttattgaa    7980
```

```
tcatatcacc acaaaacata gcaatctata atcaacccat taattctatt caatcaaaca    8040
atgaggacac attgcaatac aggtccattc attattaagc taatgcacag gaataaaaat    8100
cagt                                                                 8104

<210> SEQ ID NO 194
<211> LENGTH: 3572
<212> TYPE: DNA
<213> ORGANISM: Homo sapiens

<400> SEQUENCE: 194
acctgcactt ctgggggcgt cgagcctggc ggtagaatct tcccagtagg cggcgcggga      60
gggaaaagag gattgagggg ctaggccggg cggatcccgt cctcccccga tgtgagcagt    120
tttccgaaac cccgtcaggc gaaggctgcc cagagaggtg gagtcggtag cggggccggg    180
aacatgaggc agtctctcct attcctgacc agcgtggttc ctttcgtgct ggcgccgcga    240
cctccggatg acccgggctt cggcccccac cagagactcg agaagcttga ttctttgctc    300
tcagactacg atattctctc tttatctaat atccagcagc attcggtaag aaaaagagat    360
ctacagactt caacacatgt agaaacacta ctaactttt cagctttgaa aaggcatttt    420
aaattatacc tgacatcaag tactgaacgt ttttcacaaa atttcaaggt cgtggtggtg    480
gatggtaaaa acgaaagcga gtacactgta aaatggcagg acttcttcac tggacacgtg    540
gttggtgagc ctgactctag ggttctagcc cacataagag atgatgatgt tataatcaga    600
atcaacacag atggggccga atataacata gagccacttt ggagatttgt taatgatacc    660
aaagacaaaa gaatgttagt ttataaatct gaagatatca agaatgtttc acgtttgcag    720
tctccaaaag tgtgtggtta tttaaaagtg gataatgaag agttgctccc aaaagggtta    780
gtagacagag aaccacctga agagcttgtt catcgagtga aaagaagagc tgacccagat    840
cccatgaaga acacgtgtaa attattggtg gtagcagatc atcgcttcta cagatacatg    900
ggcagagggg aagagagtac aactacaaat tacttaatag agctaattga cagagttgat    960
gacatctatc ggaacacttc atgggataat gcaggttta aaggctatgg aatacagata   1020
gagcagattc gcattctcaa gtctccacaa gaggtaaaac ctggtgaaaa gcactacaac   1080
atggcaaaaa gttacccaaa tgaagaaaag gatgcttggg atgtgaagat gttgctagag   1140
caatttagct ttgatatagc tgaggaagca tctaaagttt gcttggcaca ccttttcaca   1200
taccaagatt ttgatatggg aactcttgga ttagcttatg ttggctctcc cagagcaaac   1260
agccatggag gtgtttgtcc aaaggcttat tatagcccag ttgggaagaa aaatatctat   1320
ttgaatagtg gtttgacgag cacaaagaat tatggtaaaa ccatccttac aaaggaagct   1380
gacctggtta caactcatga attgggacat aattttggag cagaacatga tccggatggt   1440
ctagcagaat gtgccccgaa tgaggaccag ggagggaaat atgtcatgta tccatagct   1500 gtgagtggcg atcacgagaa caataagatg ttttcaaact gcagtaaaca atcaatctat   1560
aagaccattg aaagtaaggc ccaggagtgt tttcaagaac gcagcaataa agtttgtggg   1620
aactcgaggg tggatgaagg agaagagtgt gatcctggca tcatgtatct gaacaacgac   1680
acctgctgca cagcgactg cacgttgaag aaggtgtcc agtgcagtga caggaacagt   1740
ccttgctgta aaaactgtca gtttgagact gcccagaaga agtgccagga ggcgattaat   1800
gctacttgca aggcgtgtc ctactgcaca ggtaatagca gtgagtgccc gcctccagga   1860
aatgctgaag atgacactgt ttgcttggat cttggcaagt gtaaggatgg gaaatgcatc   1920
cctttctgcg agagggaaca gcagctggag tcctgtgcat gtaatgaaac tgacaactcc   1980
```

```
tgcaaggtgt gctgcaggga cctttctggc cgctgtgtgc cctatgtcga tgctgaacaa    2040
aagaacttat ttttgaggaa aggaaagccc tgtacagtag gattttgtga catgaatggc    2100
aaatgtgaga aacgagtaca ggatgtaatt gaacgatttt gggatttcat tgaccagctg    2160
agcatcaata cttttggaaa gttttttagca gacaacatcg ttgggtctgt cctggttttc    2220
tccttgatat tttggattcc tttcagcatt cttgtccatt gtgtggataa gaaattggat    2280
aaacagtatg aatctctgtc tctgtttcac cccagtaacg tcgaaatgct gagcagcatg    2340
gattctgcat cggttcgcat tatcaaaccc tttcctgcgc cccagactcc aggccgcctg    2400
cagcctgccc ctgtgatccc ttcggcgcca gcagctccaa aactggacca ccagagaatg    2460
gacaccatcc aggaagaccc cagcacagac tcacatatgg acgaggatgg gtttgagaag    2520 gacccccttcc caaatagcag cacagctgcc aagtcatttg aggatctcac ggaccatccg    2580
gtcaccagaa gtgaaaaggc tgcctccttt aaactgcagc gtcagaatcg tgttgacagc    2640
aaagaaacag agtgctaatt tagttctcag ctcttctgac ttaagtgtgc aaaatatttt    2700
tatagatttg acctacaaat caatcacagc ttgtattttg tgaagactgg gaagtgactt    2760
agcagatgct ggtcatgtgt ttgaacttcc tgcaggtaaa cagttcttgt gtggtttggc    2820
ccttctcctt ttgaaaaggt aaggtgaagg tgaatctagc ttattttgag gctttcaggt    2880
tttagttttt aaaatatctt ttgacctgtg gtgcaaaagc agaaaataca gctggattgg    2940
gttatgaata tttacgtttt tgtaaattaa tcttttatat tgataacagc actgactagg    3000
gaaatgatca gttttttttt atacactgta atgaaccgct gaatatgagg catttggcat    3060
ttatttgtga tgacaactgg aatagttttt tttttttttt ttttttttg ccttcaacta    3120 aaaacaaagg agataaatct agtatacatt gtctctaaat tgtgggtcta tttctagtta    3180
ttacccagag ttttttatgta gcagggaaaa tatatatcta aatttagaaa tcatttgggt    3240
taatatggct cttcataatt ctaagactaa tgctctctag aaacctaacc acctaccttta    3300 cagtgagggc tatacatggt agccagttga atttatggaa tctaccaact gtttagggcc    3360
ctgatttgct gggcagtttt tctgtatttt ataagtatct tcatgtatcc ctgttactga    3420
tagggataca tgctcttaga aaattcacta ttggctggga gtggtggctc atgcctgtaa    3480
tcccagcact tggagaggct gaggttgcgc cactcactc cagcctgggt gacagagtga    3540
gactctgcct caaaaaaaaa aaaaaaaaaa aa                                  3572
```

<210> SEQ ID NO 195
<211> LENGTH: 4126
<212> TYPE: DNA
<213> ORGANISM: Rattus norvegicus

<400> SEQUENCE: 195

```
ttccggctgt gggcagcagg gtggtccgcg actgcggccg gaagcaggct gagcggctct     60
cggcgagcgc cgcctgtact tccggggact tcagcctagc tcttgagttt tccctgtagg    120
cggcgcggga gggaaaagtt tgcagggccg tgctgggaag atcacctccg cttcccaatg    180
tgagcagttt ctcgaacgct ctctctagaa ggttgcccag agaggtggtg gacgggaaca    240
tgaggcagcg tctcctcttc ctgaccactt tggtgccttt cgtcctggca ccccgacctc    300
cggaggaacc aggctctggc tcccacctgc gacttgagaa gcttgattct ttgctctcag    360
actacgatat cctctctttta tctaaatatcc agcagcactc cataaggaaa agggatctac    420
agtctgcgac acacttagaa acactactaa ctttttcagc tttgaaaagg cattttaaat    480
```

```
tatacttgac atcaagtaca gaacgctttt cacagaactt gcgagtcgtg gtggtggatg    540
ggaaagagga aagcgagtac agtgtgaagt ggcaggactt cttcagcgga catgtggttg    600
gtgagcctga ctctagggtt ctagcgcaca taggagatga tgatgtcaca gtaagaatca    660
acacagatgg ggcagaatat aacatagagc cactttggag gtttgttaat gatactaaag    720
ataaaaggat gctggtgtat aagtctgaag atatcaagga ttttttcacgt ttgcagtctc    780
caaaagtatg tggttattta aatgcagata gtgaagagtt gcttccaaaa gggctcatag    840
acagagagcc atctgaagag tttgtccgtc gagtgaagag gcgagctgaa cctaacccat    900
tgaagaatac ttgtaaatta ctggtggtgg cagatcatcg attttataag tacatgggcc    960
gaggagaaga gagcactact acaaattact aatagagtt aattgaccga gttgatgaca    1020
tataccggaa cacctcgtgg gacaatgcag gatttaaagg ttatggagta cagatagaac    1080
agattcgaat tctcaagtct ccacaagagg taaaacctgg tgaaagacac ttcaatatgg    1140
caaaaagttt tccaaatgaa gaaaaggatg cttgggatgt gaagatgctg ctggagcaat    1200
ttagccttga tatagctgaa gaggcctcta agtctgcct ggctcatctt ttcacctacc    1260
aagattttga tatgggaact cttggattag cttacgttgg ttctcccaga gcaaacagtc    1320
atggaggggt ttgtccaaaa gcttattaca acccaggtgt gaagaagaac atctatttga    1380
atagtggtct gacaagtaca aaaaattatg gtaaaaccat ccttacaaag gaggctgacc    1440
tggttacaac tcatgaattg ggacacaatt ttggagcaga acatgatcct gatgggctgg    1500
cagagtgtgc cccaaatgag gaccaaggag gaaagtatgt tatgtacccc atagctgtga    1560
gtggtgacca tgagaataat aagatgtttt caaactgcag taaacagtcc atctacaaga    1620
ccatagaaag caaggctcaa gagtgcttcc aggagcgcag caacaaggtg tgcggcaact    1680
ccagggtgga cgaaggagaa gagtgtgacc cgggcatcat gtacctgaac aacgacacct    1740
gctgcaatag tgactgcaca ctgaagccag gtgtgcagtg cagtgatagg aatagtcctt    1800
gctgtaaaaa ttgtcagttt gagacggccc agaagaagtg ccaggaggct atcaatgcta    1860
cttgcaaagg agtgtcttac tgcacaggga atagcagtga gtgcccccca ccaggagatg    1920
ctgaagatga cactgtgtgc ttggacctgg gcaagtgcaa ggctgggaaa tgcatccctt    1980
tctgcaagag ggagcaggag ctggagtcct gcgcatgtgc tgacaccgac aactcgtgca    2040
aggtatgctg caggaaccct tctggcccat gtgtgcctta cgtcgatgca gagcaaagaa    2100
acttattttt gaggaaaggg aagccctgta cagtagggtt ttgtgacatg aatggcaaat    2160
gtgagaaacg ggtacaggac gtaattgagc ggttttggga tttcattgac cagctgagca    2220
tcaacacttt tgggaagttt ctggcagaca acatcgttgg gtctgttctg gtttctcct    2280
tgatattttg gattcctttc agcattcttg tccactgtgt ggataagaaa ctggacaagc    2340
agtatgagtc cctgtctctg tttcatcaca gtaacattga gatgttgagc agcatggact    2400
cagcatctgt tcgcattatc aagccgttcc ctgcaccca gactccaggt cgtctgcagg    2460
ccctgcagcc ggctgcaatg atgccgccag tgtctgcggc tccaaaactg gatcaccaga    2520
ggatggacac catccaggaa gaccccagca cagattcaca tgtggatgat gatggctttg    2580
agaaggaccc cttccccaac agcagtgcag ccgccaagtc ctttgaggac ctcacagacc    2640
acccagtcac caggagtgag aaggccgcct ccttcaagct gcagcgtcag agccgagttg    2700
atagcaaaga gacagagtgt tagtgggagc ctgggcctgc tctgggggac acagacctac    2760
agatgttcca cagagctgac ctgaatcaaa atagactgta atgatctgag aaacgggagc    2820
agcttagcag atgctggtca tgtgacagga ccttcacatg acatcctgtg tatgtaggcc    2880
```

```
ctttgaagag gtgaggtaaa tctggcttat ttaaggcttt caggttttgg ggttttcttt    2940
tgtaatctaa aaatctcctt tgacctgtgg tgcagaagca gaaaataagg ctggatcaag    3000
ttcctggtga cagcactgat taagccttca gtctgttttt ctgtatgctg taaggtcctc    3060
tcactacggt gaagcactta gcagtgagga taactggaac acagacttt tggggg tttt    3120 ggccttcaca tgtgcgttgt ctccaaatgc cgtctgtctt ggcactgaac tttgtggata    3180
cagtcctttc caagatgaag actagctctg aacagtcta tacaaacagc cacatgaact     3240
tcaagatggc ctattaactg cttagcccca ggttccctgg acagttttc cgttttgcaa     3300 aaagtgtctt cacgggtctc taaacattgt ttgtcttaaa aaatactggg ctggagagtt    3360
ggccccacag ttaagagcac ttggtttcat tcccagtacc cacacggtgg ctcttaactc    3420
caatcccagg ggagatgaca tcttctgaac tctagaacac aaggcatgca ttggtgcagt    3480
caaacatgca ggcaacacac acaaatttag aaagccaagt gctgtaagaa gttgcacatc    3540
ccccaaccta cagtgcttcg cggtctgagc tggagtggag ctctctcctg aacactctgg    3600
aaggctggca ggtgctgagc tggctaggga gacgggtggg gcccagccct ggaagaaccg    3660
tcttcagcct cagcaagcag acactcgcgt tacctcaggc tttggggctt caggacccag    3720
gatgttttgt acttattgtg tgaggataaa taccattagc ctgaattctc atttctgtaa    3780
gttttagtta taaagctttt ttttcttcta agaattgcaa tgtgctcacc agcaaacacg    3840
tcttaaccag aataacttgt aactctgagg acagttaacc aaacctgtgc cttgtctctc    3900
ctgagggtgt ctgttacact aatacttgaa catgtacctt gtggtattgg ctcctttac    3960 tagtcatgac agccttatat gttagttaca cttt gaggat ttgctctaag gtgagtgggg    4020
tgtgtgggtg tatgtatgaa tgaaacagtt ggcagaatat aagaaaacca tttttataaa   4080
attgtgactt tttaaaacaa aaaaaaaaaa aaaaaaaaaa aaaaaa                    4126

<210> SEQ ID NO 196
<211> LENGTH: 4508
<212> TYPE: DNA
<213> ORGANISM: Mus musculus

<400> SEQUENCE: 196
gctgcggccg gaaacgagtt aagccgctct cagcgagcgc cgcctgcact tccggggacg      60
tgagcctagc ttccctgtag gcggcgcggg agggagaagt ttgcagggcc gtgctgggaa     120
gatcacctcc gctcccaatg tgagcagttt cccgaacgct ctttcggaga aggtttccca    180
gagaggtggt ggacgggaac atgaggcggc gtcctcctcat cctgaccact ttggtgcctt    240
tcgtcctggc accccgacct ccggaggaag caggctctgg ctcccatccg cgacttgaga    300
agcttgattc tttgctctca gactacgaca tcctctcctt agctaatatt cagcagcact    360
ccataaggaa aagggatcta cagtctgcga cacacttaga aacattacta acttttttcag   420 ctttgaaaag acatttttaaa ttatacttga catcaagtac cgaacgcttt tcacaaaact    480
tgagagtcgt ggtggtggac gggaagaag aaagcgagta cagcgtgaag tggcagaact     540
tcttcagtgg tcacgtggtt ggtgagcctg actctagggt tctagcccac ataggagatg    600
atgatgttac agtgagaatc aacacagatg gggcagaata taacgtagag ccactttgga    660
ggtttgtcaa tgatactaaa gataaacgaa tgctggtgta taagtctgaa gatatcaagg    720
atttttcacg tttgcagtct ccaaaagtat gtggttattt aaatgcagat agtgaagagc    780
tgcttccaaa agggctcata gacagagagc catctgaaga gtttgttcgt cgagtgaaga    840
```

```
gacgagctga acctaacccc ttgaagaata cttgtaaatt actggtggta gcagatcatc    900
gattttataa atacatgggc cgtggagaag agagcaccac tacaaattac ttaggctaca    960
tttcaggcac tcgggacaga gtgacgaccg actgcttttt agagttttg  atagagctaa   1020 ttgaccgagt tgatgacata taccggaaca cgtcgtggga taatgcaggg tttaaagggt   1080
atggagtgca gatagagcag attcgaattc tcaagtctcc acaagaggta aaacctggtg   1140
aaagacactt caatatggca aaagtttcc  caaacgaaga aaggatgct  tgggatgtga   1200 agatgctatt agagcaattt agctttgata tagctgaaga agcatctaaa gtctgcctgg   1260
ctcatctttt cacgtaccag gattttgata tgggaactct tggattagct tacgttggtt   1320
ctcccagagc aaacagtcat ggaggggttt gtccaaaagc ttattacaac ccaactgtga   1380
agaaaaacat ctatttaaat agtggtctga ctagtactaa aaattatggc aaaactattc   1440
tcacaaagga agctgacctg gttacaactc atgaattggg acataatttt ggagcagaac   1500
atgaccctga tgggctagca gaatgtgccc caaatgagga ccaaggagga aagtatgtca   1560
tgtatcccat agctgtgagc ggtgaccacg agaataataa gatgttttca aactgcagta   1620
aacagtccat ctacaagacc atagaaagta aggctcaaga gtgcttccag gagcgcagca   1680
acaaggtgtg tggcaactcc agggtggatg aaggagagga gtgtgacccg ggtattatgt   1740
acctgaacaa cgacacctgc tgcaatagtg actgcacact gaagccgggt gtgcagtgca   1800
gtgataggaa cagtccttgc tgtaaaaact gtcagtttga cggcgcag   aagaagtgcc   1860 aggaggctat taatgctaca tgcaaggag  tgtcttactg cacagggaat agcagtgagt   1920
gccccccacc cggagatgct gaagatgaca ctgtgtgctt ggaccttggc aagtgcaagg   1980
ctgggaaatg catcccttc  tgcaagaggg agcaggagct ggagtcctgc gcatgcgttg   2040
acactgacaa ctcgtgcaag gtgtgctgca ggaacctttc tggcccgtgt gtgccgtacg   2100
tcgatgcaga gcaaaagaac ttgttttga  ggaaagggaa gccatgtaca gtagggtttt   2160
gcgacatgaa tggcaaatgt gagaaacgag tacaggacga aattgagcga ttttgggatt   2220
tcattgacca gctgagcatc aacacttttg ggaagtttct ggcagataac atcgttgggt   2280
ctgttctggt tttctccttg atattttgga ttcctttcag cattcttgtc cactgtgtgg   2340
ataagaaact ggacaagcag tatgaatccc tgtctctgtt tcatcacagt aacattgaga   2400
tgctgagcag catggactca gcatctgttc gcatcatcaa gcccttcct  gcaccccaga   2460 ctccaggtcg tctgcaggcc ctgcagccag ctgccatgat gccgccagta cctgcagctc   2520
caaaactgga ccaccagagg atggacacca tccaggaaga ccccagcaca gactcacatg   2580
cagatgatga cggttttgag aaggacccct tccccaacag cagcacagct gccaagtcct   2640
ttgaggatct cacagaccac ccagtcacca ggagcgaaaa ggcggcctca ttcaagctgc   2700
agcgtcagag ccgagttgac agcaaagaga cagagtgcta gtggggaacc ttggcctgct   2760
ctaggacata tacctgcaga tgttccatag agctgacctg aatcaaaaca tagattataa   2820
tgatctgaga aacggggaag caacttagca gatgctggtc atgtgctatg accttcacat   2880
gacatcctat gtatgtaggc cctttgaaga ggtgaggtaa atctggctta tgtaaggctt   2940
tcaggttttg ggttttctt  ttataatcta aaatctcctt tgacctgtgg tgcagaagca   3000
gaaagtaagg ctggacccccg ttcctggtga cagtgctgtt aagtcttcag tctgttttc   3060 tgtaccctct gactacagtg aagcacttaa cagtgaggat aactggaaca cagacatact   3120
tgtttgtttg ttttgttttt gttttgtttt tttttttt   gaccctcaac taaaagagga   3180
gcaagagaaa cctgcttgta tgttgtctcc aaatgcggcc tgtcttggca ctgaattctt   3240
```

```
tgtagatgga gagacctgcc tacacttagg gccatctaca ttaagagcag tcctttccaa    3300
gaggaacagt ttatagaaac agccacatga acttcgagat ggcctattaa ctgttcagcc    3360
ccagattcac tgggcagttt ttccatttta caaatgtgtc gtctttaaac tgtttgcctt    3420
aaaaaaaaaa atcaatattg ggctggagag ttggccccac agttaagagc agttggtctc    3480
attctcagca cccacatggt ggctctcaac tctgtaactc caatcccaga ggagatgaca    3540
tcttctgaac tctaggacac gaggcataca ttggtgcagg caaaacaaag ccaagtgctg    3600
taaaatgtgg caataaccac aaaacctata gtgcctcaca gtatggactg agtggtgaat    3660
agacactctt cccagaacca cttctggaca ggccgggatg tgctggctgg ctaggaagag    3720
ggggtgggag tgggagagtg gtgctgccat cggggcccag ccctagaaga actgaccttc    3780
agtctcggca gtagacacc cacgtgacct ctggctctgg tgcttcaaga tgttctgtac    3840
ttactgtgtg aggaataaat gccattagcc tgaattctga tttctataaa ttctagttat    3900
aaatgctctt tcttctaag aattgcagtg tgctcacaag ccaacacatt ttaaccaaga    3960
taatttgtaa actctgagga cagttaacca agcctgtgcc ttgtctctcc tgaggacgcc    4020
tgttacacta atacttgaat atataccttg tggtatttgc tcttttact agtcatgata    4080 gtcttgtatt ttaattacac tttgatgatt tgctataggg agagtggggt gtgtgggtat    4140
atgtatgaat gaaacagttg gcagaatata agaaaaccat ttttataaaa ttgtgacttt    4200
ttaaaccaaa attgtcttaa ttgtattact ttttttttct ttggcatgta cagaattaat    4260
aagatgctca gggcatattc tatagctgtg gcattgatga tacctgcctc agtcaataaa    4320
tactgaatat caaagcagtg gattgcgtat ataacatttc cctgaaaaat aagttagtag    4380
gttttttgat caataatcat gaacagaagt taagcttgga aaagacattt aatcaatctc    4440
ttgatgtctg tgaattacta ataaagctac gcacatgttc acagaatgtt tgtggctacc    4500
aacatgaa                                                            4508

<210> SEQ ID NO 197
<211> LENGTH: 4470
<212> TYPE: DNA
<213> ORGANISM: Mus musculus

<400> SEQUENCE: 197
gctgcggccg gaaacgagtt aagccgctct cagcgagcgc cgcctgcact tccggggacg      60
tgagcctagc ttccctgtag gcggcgcggg agggagaagt ttgcagggcc gtgctgggaa     120
gatcacctcc gctcccaatg tgagcagttt cccgaacgct ctttcggaga aggtttccca     180
gagaggtggt ggacgggaac atgaggcggc gtctcctcat cctgaccact ttggtgcctt     240
tcgtcctggc accccgacct ccggaggaag caggctctgg ctcccatccg cgacttgaga     300
agcttgattc tttgctctca gactacgaca tcctctcctt agctaatatt cagcagcact     360
ccataaggaa aagggatcta cagtctgcga cacacttaga acattacta acttttttcag    420 ctttgaaaag acattttaaa ttatacttga catcaagtac cgaacgcttt tcacaaaact     480
tgagagtcgt ggtggtggac gggaaagaag aaagcgagta cagcgtgaag tggcagaact     540
tcttcagtgg tcacgtggtt ggtgagcctg actctagggt tctagcccac ataggagatg     600
atgatgttac agtgagaatc aacacagatg gggcagaata taacgtagag ccactttgga     660
ggtttgtcaa tgatactaaa gataaacgaa tgctggtgta taagtctgaa gatatcaagg     720 attttttcacg tttgcagtct ccaaaagtat gtggttattt aaatgcagat agtgaagagc     780
```

```
tgcttccaaa agggctcata gacagagagc catctgaagt gcatacaaat tcatatagag    840
tttgttcgtc gagtgaagag acgagctgaa cctaacccct tgaagaatac ttgtaaatta    900
ctggtggtag cagatcatcg attttataaa tacatgggcc gtggagaaga gagcaccact    960
acaaattact taatagagct aattgaccga gttgatgaca tataccggaa cacgtcgtgg   1020
gataatgcag ggtttaaagg gtatggagtg cagatagagc agattcgaat tctcaagtct   1080
ccacaagagg taaaacctgg tgaaagacac ttcaatatgg caaaaagttt cccaaacgaa   1140
gagaaggatg cttgggatgt gaagatgcta ttagagcaat ttagctttga tatagctgaa   1200
gaagcatcta aagtctgcct ggctcatctt ttcacgtacc aggattttga tatgggaact   1260
cttggattag cttacgttgg ttctcccaga gcaaacagtc atggagtggt ttgtccaaaa   1320
gcttattaca acccaactgt gaagaaaaac atctatttaa atagtggtct gactagtact   1380
aaaaattatg gcaaaactat tctcacaaag gaagctgacc tggttacaac tcatgaattg   1440
ggacataatt ttggagcaga acatgaccct gatgggctag cagaatgtgc cccaaatgag   1500
gaccaaggag gaaagtatgt catgtatccc atagctgtga gcggtgacca cgagaataat   1560
aagatgtttt caaactgcag taaacagtcc atctacaaga ccatagaaag taaggctcaa   1620
gagtgcttcc aggagcgcag caacaaggtg tgtggcaact ccagggtgga tgaaggagag   1680
gagtgtgacc cgggtattat gtacctgaac aacgacacct gctgcaatag tgactgcaca   1740
ctgaagccgg gtgtgcagtg cagtgatagg aacagtcctt gctgtaaaaa ctgtcagttt   1800
gagacggcgc agaagaagtg ccaggaggct attaatgcta catgcaaagg agtgtcttac   1860
tgcacaggga atagcagtga gtgcccccca cccggagatg ctgaagatga cactgtgtgc   1920
ttggaccttg gcaagtgcaa ggctgggaaa tgcatccctt tctgcaagag ggagcaggag   1980
ctggagtcct gcgcatgcgt tgacactgac aactcgtgca aggtgtgctg caggaacctt   2040
tctggcccgt gtgtgccgta cgtcgatgca gagcaaaaga acttgttttt gaggaaaggg   2100
aagccatgta cagtagggtt ttgcgacatg aatggcaaat gtgagaaacg agtacaggac   2160
gtaattgagc gattttggga tttcattgac cagctgagca tcaacacttt tgggaagttt   2220
ctggcagata acatcgttgg gtctgttctg gttttctcct tgatattttg gattcctttc   2280
agcattcttg tccactgtgt ggataagaaa ctggacaagc agtatgaatc cctgtctctg   2340
tttcatcaca gtaacattga gatgctgagc agcatggact cagcatctgt tcgcatcatc   2400
aagcccttc ctgcaccca gactccaggt cgtctgcagg ccctgcagcc agctgccatg   2460
atgccgccag tacctgcagc tccaaaactg gaccaccaga ggatggacac catccaggaa   2520
gaccccagca cagactcaca tgcagatgat gacggttttg agaaggaccc cttccccaac   2580
agcagcacac tgccaagtc ctttgaggat ctcacagacc acccagtcac caggagcgaa   2640
aaggcggcct cattcaagct gcagcgtcag agccgagttg acagcaaaga gacagagtgc   2700
tagtggggaa ccttggcctg ctctaggaca tatacctgca gatgttccat agagctgacc   2760
tgaatcaaaa catagattat aatgatctga gaaacgggga agcaacttag cagatgctgg   2820
tcatgtgcta tgaccttcac atgacatcct atgtatgtag ccctttgaa gaggtgaggt   2880
aaatctggct tatgtaaggc tttcaggttt tgggttttc tttataatc taaaatctcc   2940
tttgacctgt ggtgcagaag cagaaagtaa ggctggaccc cgttcctggt gacagtgctg   3000
ttaagtcttc agtctgtttt tctgtaccct ctgactacag tgaagcactt aacagtgagg   3060
ataactggaa cacagacata cttgtttgtt tgttttgttt ttgttttgt ttttttttt   3120
ttgacccca actaaaagag gagcaagaga aacctgcttg tatgttgtct ccaaatgcgg   3180
```

```
cctgtcttgg cactgaattc tttgtagatg gagagacctg cctacactta gggccatcta    3240
cattaagagc agtcctttcc aagaggaaca gtttatagaa acagccacat gaacttcgag    3300
atggcctatt aactgttcag ccccagattc actgggcagt ttttccattt tacaaatgtg    3360
tcgtctttaa actgtttgcc ttaaaaaaaa aaatcaatat tgggctggag agttggcccc    3420
acagttaaga gcagttggtc tcattctcag cacccacatg gtggctctca actctgtaac    3480
tccaatccca gaggagatga catcttctga actctaggac acgaggcata cattggtgca    3540
ggcaaaacaa agccaagtgc tgtaaaatgt ggcaataacc acaaaaccta tagtgcctca    3600
cagtatggac tgagtggtga atagacactc ttcccagaac cacttctgga caggccggga    3660
tgtgctggct ggctaggaag agggggtggg agtgggagag tggtgctgcc atcggggccc    3720
agccctagaa gaactgacct tcagtctcgg caagtagaca cccacgtgac ctctggctct    3780
ggtgcttcaa gatgttctgt acttactgtg tgaggaataa atgccattag cctgaattct    3840
gatttctata aattctagtt ataaatgctc ttttcttcta agaattgcag tgtgctcaca    3900
agccaacaca ttttaaccaa gataatttgt aaactctgag gacagttaac caagcctgtg    3960
ccttgtctct cctgaggacg cctgttacac taatacttga atatatacct tgtggtattt    4020
gctcttttta ctagtcatga tagtcttgta ttttaattac actttgatga tttgctatag    4080
ggagagtggg gtgtgtgggt atatgtatga atgaaacagt tggcagaata taagaaaacc    4140 attttttataa aattgtgact ttttaaacca aaattgtctt aattgtatta cttttttttt    4200
ctttggcatg tacagaatta ataagatgct cagggcatat tctatagctg tggcattgat    4260 gataccctgcc tcagtcaata aatactgaat atcaaagcag tggattgcgt atataacatt    4320
tccctgaaaa ataagttagt aggttttttg atcaataatc atgaacagaa gttaagcttg    4380
gaaaagacat ttaatcaatc tcttgatgtc tgtgaattac taataaagct acgcacatgt    4440
tcacagaatg tttgtggcta ccaacatgaa                                      4470
```

<210> SEQ ID NO 198
<211> LENGTH: 4451
<212> TYPE: DNA
<213> ORGANISM: Mus musculus

<400> SEQUENCE: 198

```
gctgcggccg gaaacgagtt aagccgctct cagcgagcgc cgcctgcact tccggggacg      60
tgagcctagc ttccctgtag gcggcgcggg agggagaagt ttgcagggcc gtgctgggaa     120
gatcacctcc gctcccaatg tgagcagttt cccgaacgct cttcggagaa aggtttccca     180
gagaggtggt ggacgggaac atgaggcggc gtctcctcat cctgaccact ttggtgcctt     240
tcgtcctggc accccgacct ccggaggaag caggctctgg ctcccatccg cgacttgaga     300
agcttgattc tttgctctca gactacgaca tcctctcctt agctaatatt cagcagcact     360
ccataaggaa aagggatcta cagtctgcga cacacttaga acattactac acttttttcag    420 cttttgaaaag acatttttaaa ttatacttga catcaagtac cgaacgcttt tcacaaaact    480
tgagagtcgt ggtggtggac gggaaagaag aaagcgagta cagcgtgaag tggcagaact    540
tcttcagtgg tcacgtggtt ggtgagcctg actctagggt tctagcccac ataggagatg     600
atgatgttac agtgagaatc aacacagatg gggcagaata taacgtagag ccactttgga    660
ggtttgtcaa tgatactaaa gataaacgaa tgctggtgta taagtctgaa gatatcaagg    720 attttttcacg tttgcagtct ccaaaagtat gtggttattt aaatgcagat agtgaagagc    780
```

```
tgcttccaaa agggctcata gacagagagc catctgaaga gtttgttcgt cgagtgaaga      840
gacgagctga acctaacccc ttgaagaata cttgtaaatt actggtggta gcagatcatc      900
gattttataa atacatgggc cgtggagaag agagcaccac tacaaattac ttaatagagc      960
taattgaccg agttgatgac atataccgga acacgtcgtg ggataatgca gggtttaaag     1020
ggtatggagt gcagatagag cagattcgaa ttctcaagtc tccacaagag gtaaaacctg     1080
gtgaaagaca cttcaatatg gcaaaaagtt tcccaaacga agagaaggat gcttgggatg     1140
tgaagatgct attagagcaa tttagctttg atatagctga agaagcatct aaagtctgcc     1200
tggctcatct tttcacgtac caggattttg atatgggaac tcttggatta gcttacgttg     1260
gttctcccag agcaaacagt catggagggg tttgtccaaa agcttattac aacccaactg     1320
tgaagaaaaa catctattta aatagtggtc tgactagtac taaaaattat ggcaaaacta     1380
ttctcacaaa ggaagctgac ctggttacaa ctcatgaatt gggacataat tttggagcag     1440
aacatgaccc tgatgggcta gcagaatgtg ccccaaatga ggaccaagga ggaaagtatg     1500
tcatgtatcc catagctgtg agcggtgacc acgagaataa taagatgttt tcaaactgca     1560
gtaaacagtc catctacaag accatagaaa gtaaggctca agagtgcttc caggagcgca     1620
gcaacaaggt gtgtggcaac tccagggtgg atgaaggaga ggagtgtgac ccgggtatta     1680
tgtacctgaa caacgacacc tgctgcaata gtgactgcac actgaagccg ggtgtgcagt     1740
gcagtgatag gaacagtcct tgctgtaaaa actgtcagtt tgagacggcg cagaagaagt     1800
gccaggaggc tattaatgct acatgcaaag gagtgtctta ctgcacaggg aatagcagtg     1860 agtgccccc acccggagat gctgaagatg acactgtgtg cttggacctt ggcaagtgca     1920
aggctgggaa atgcatccct ttctgcaaga gggagcagga gctggagtcc tgcgcatgcg     1980
ttgacactga caactcgtgc aaggtgtgct gcaggaaacct ttctggcccg tgtgtgccgt     2040
acgtcgatgc agagcaaaag aacttgtttt tgaggaaagg gaagccatgt acagtagggt     2100
tttgcgacat gaatggcaaa tgtgagaaac gagtacagga cgtaattgag cgattttggg     2160
atttcattga ccagctgagc atcaacactt tgggaagtt tctggcagat aacatcgttg     2220
ggtctgttct ggttttctcc ttgatatttt ggattccttt cagcattctt gtccactgtg     2280
tggataagaa actggacaag cagtatgaat ccctgtctct gtttcatcac agtaacattg     2340
agatgctgag cagcatggac tcagcatctg ttcgcatcat caagccccttt cctgcacccc     2400 agactccagg tcgtctgcag gccctgcagc cagctgccat gatgccgcca gtacctgcag     2460
ctccaaaact ggaccaccag aggatggaca ccatccagga agaccccagc acagactcac     2520
atgcagatga tgacggtttt gagaaggacc ccttccccaa cagcagcaca gctgccaagt     2580
cctttgagga tctcacagac cacccagtca ccaggagcga aaaggcggcc tcattcaagc     2640
tgcagcgtca gagccgagtt gacagcaaag agacagagtg ctagtgggga accttggcct     2700
gctctaggac atatacctgc agatgttcca tagagctgac ctgaatcaaa acatagatta     2760
taatgatctg agaaacgggg aagcaactta gcagatgctg gtcatgtgct atgaccttca     2820
catgacatcc tatgtatgta ggccctttga agaggtgagg taaatctggc ttatgtaagg     2880
ctttcaggtt tgggttttt cttttataat ctaaaatctc ctttgacctg tggtgcagaa     2940
gcagaaagta aggctggacc ccgttcctgg tgacagtgct gttaagtctt cagtctgttt     3000
ttctgtaccc tctgactaca gtgaagcact taacagtgag gataactgga acacagacat     3060
acttgtttgt ttgttttgtt tttgtttttg tttttttttt tttgaccctc aactaaaaga     3120
ggagcaagag aaacctgctt gtatgttgtc tccaaatgcg gcctgtcttg gcactgaatt     3180
```

```
ctttgtagat ggagagacct gcctacactt agggccatct acattaagag cagtcctttc    3240
caagaggaac agtttataga aacagccaca tgaacttcga gatggcctat taactgttca    3300
gccccagatt cactgggcag tttttccatt ttacaaatgt gtcgtcttta aactgtttgc    3360
cttaaaaaaa aaaatcaata ttgggctgga gagttggccc cacagttaag agcagttggt    3420
ctcattctca gcacccacat ggtggctctc aactctgtaa ctccaatccc agaggagatg    3480
acatcttctg aactctagga cacgaggcat acattggtgc aggcaaaaca aagccaagtg    3540
ctgtaaaatg tggcaataac cacaaaacct atagtgcctc acagtatgga ctgagtggtg    3600
aatagacact cttcccagaa ccacttctgg acaggccggg atgtgctggc tggctaggaa    3660 gaggggggtgg gagtgggaga gtggtgctgc catcggggcc cagccctaga agaactgacc    3720
ttcagtctcg gcaagtagac acccacgtga cctctggctc tggtgcttca agatgttctg    3780
tacttactgt gtgaggaata aatgccatta gcctgaattc tgatttctat aaattctagt    3840
tataaatgct cttttcttct aagaattgca gtgtgctcac aagccaacac attttaacca    3900
agataatttg taaactctga ggacagttaa ccaagcctgt gccttgtctc tcctgaggac    3960
gcctgttaca ctaatacttg aatatatacc ttgtggtatt tgctcttttt actagtcatg    4020
atagtcttgt attttaatta cactttgatg atttgctata gggagagtgg ggtgtgtggg    4080
tatatgtatg aatgaaacag ttggcagaat ataagaaaac catttttata aaattgtgac    4140
tttttaaacc aaaattgtct taattgtatt actttttttt tctttggcat gtacagaatt    4200
aataagatgc tcagggcata ttctatagct gtggcattga tgatacctgc ctcagtcaat    4260
aaatactgaa tatcaaagca gtggattgcg tatataacat ttccctgaaa aataagttag    4320
taggtttttt gatcaataat catgaacaga agttaagctt ggaaaagaca tttaatcaat    4380
ctcttgatgt ctgtgaatta ctaataaagc tacgcacatg ttcacagaat gtttgtggct    4440
accaacatga a                                                          4451
```

COMPOSITIONS AND METHODS FOR INHIBITING EXPRESSION OF ADAMTS-5 AND ADAM17

CROSS REFERENCE TO RELATED APPLICATIONS

This application is the U.S. National Phase Application under 35 U.S.C. § 371 of International Application No. PCT/IB2015/002574, filed Dec. 23, 2015, designating the U.S. and published as WO 2016/103042 A1 on Jun. 30, 2016, which claims the benefits of Chinese Patent Application Nos. 201410828587.5 and 201410827650.3, both filed on Dec. 25, 2014, the contents of which are incorporated herein by reference in their entirety.

ELECTRONIC SEQUENCE LISTING

The instant application contains a Sequence Listing that has been submitted electronically in ASCII format and is hereby incorporated by reference in its entirety. Said ASCII copy, created on Dec. 18, 2015, is named 13091.0001-00304_SL.txt and is 131,638 bytes in size, and updated by a file entitled JEEK034001APCSEQLIST.txt, which is 131,681 bytes in size, created and last modified on Jun. 23, 2017.

FIELD

The invention relates to small interfering RNA (siRNA), use of siRNA in RNA interference (RNAi) to inhibit the expression of ADAMTS-5 or ADAM17, and use of siRNA to treat pathological conditions by down-regulating ADAMTS-5 or ADAM17. The pathological conditions may include arthritis, such as, e.g., osteoarthritis (OA) and rheumatoid arthritis (RA).

BACKGROUND

OA is a chronic disease featured with bone and joint degeneration. Imposing serious hazards to human health, OA currently lacks effective treatment. Therefore, a need exists for new methods of effectively preventing and/or treating OA. Clinical and pathological features of arthritis include cartilage damage resulting from proteolysis of the extracellular matrix (ECM). Cartilage ECM degradation caused by increased proteolytic activity acts as a direct cause for cartilage degeneration, ultimately leading to cartilage damage. Interleukin-1 (IL-1) and tumor necrosis factor-α (TNF-α) have significant functional involvement in hFLS cell catabolism and ECM degradation. Studies have shown the presence of IL-1 and TNF-α at high concentrations in arthritis patients' synovial fluid. These proteins are considered key pro-inflammatory cytokines, playing an important role in the pathogenesis of arthritis.

A Disintegrin And Metalloproteinase with Thrombospondin Motifs (ADAMTS) is a family of secreted, multi-domain matrix-associated zinc metalloendopeptidases that have diverse roles in embryonic development, angiogenesis, coagulation, and inflammation. With 19 members, the family uses a variety of ECM components as substrates. The ADAMTS family shares a high degree of protein structural similarity. For example, the members contain a proprotein domain following an N-terminal signal peptide sequence and undergo a post-translational cleavage to become active proteases. In addition, the proteases include at the C-terminal at least one conservative TSPI-like repeat motif, which mediates binding of the proteases with the ECM.

ADAMTS-5 catalyzes aggrecan degradation as a type of aggrecanases or proteoglycanases. Two major cleavage sites exist in aggrecan: a matrix metalloproteinase (MMP) cleavage site located at Asn341 and Phe342, and an aggrecanase cleavage site located at Glu373 and Ala374. Abundant aggrecan present in the articular cartilage helps to improve the tension and anti-pressure force at the joints. Severe aggrecan damage has been discovered in OA and RA patients. Thus, aggrecanases have become a new target for treating arthritis and other diseases. For example, in malignant glioma, the expression level of ADAMTS-5 significantly increases, leading to glioma invasion and metastasis as a result of aggrecan degradation. In addition, extracellular protein degradation or damage may cause diseases such as cancer, asthma, chronic obstructive pulmonary disease, atherosclerosis, age-related macular degeneration, myocardial infarction, hepatitis, tendonitis, angiogenesis, multiple sclerosis, glomerulonephritis, osteopenia, and periodontal diseases.

ADAM17 belongs to the A Disintegrin And Metalloprotease (ADAM) family. As a class of cell surface glycoproteins, the ADAM family plays a role in a variety of physiological and pathological processes, such as cell-cell and cell-matrix adhesion, cell fusion, ECM degradation, signal transduction, and tumor formation, growth, and metastasis. ADAM17 is also known as TNF-α converting enzyme (TACE), which produces free TNF-α by releasing membrane-bound TNF-α. Free TNF-α in turn causes excessive secretion of inflammatory cytokines, cell apoptosis, and intracellular signaling disorders, leading to a variety of diseases, including RA, systemic Lupus erythematosus (SLE), multiple sclerosis, acute infectious diseases, asthma, atopic dermatitis, and psoriasis. Besides TNF-α, ADAM17 also regulates a macrophage colony stimulating factor or chemokine, fractalkine (FKN). As a result, ADAM17 inhibitors are viewed as potential candidates for treating inflammation-related diseases. Unfortunately, previous studies have shown that broad-spectrum ADAM inhibitors possess tissue toxicity. Thus, there remains a challenge to develop highly selective small molecule inhibitors of the conserved ADAMs family.

In 1998, Craig Mello and Andrew Farr discovered gene silencing. Thereafter Tuschl and his colleagues found that chemically synthesized siRNAs of 19 to 25 bp can specifically and efficiently silence target mRNAs in mammalian cells. Since then, siRNA has been widely used for gene function study and disease treatment.

SUMMARY

In certain aspects, the present disclosure provides a double-stranded siRNA targeted against ADAMTS-5 comprising a sense strand and a complementary antisense strand. In some embodiments, the antisense strand may hybridize with an ADAMTS-5 mRNA, and the sense strand may hybridize with the antisense strand.

In some embodiments, the sense strand may comprise a nucleotide sequence having at least 60% identity to 5'-GGAUUUAUGUGGGCAUCAU-3' (SEQ ID NO: 1), and the antisense strand may comprise a nucleotide sequence having at least 60% identity to 5'-AUGAUGC-CCACAUAAAUCC-3' (SEQ ID NO: 2). In some embodiments, the sense strand may comprise a nucleotide sequence having at least 65%, 70%, 75%, 80%, 85%, 90%, 95%, 96%, 97%, 98%, or 99% identity to SEQ ID NO: 1, and the antisense strand may comprise a nucleotide sequence having at least 65%, 70%, 75%, 80%, 85%, 90%, 95%, 96%, 97%, 98%, or 99% identity to SEQ ID NO: 2. In some embodiments, the sense strand may comprise a nucleotide sequence having at least 60% (such as, e.g., 65%, 70%, 75%, 80%, 85%, 90%, 95%, 96%, 97%, 98%, or 99%) identity to SEQ ID NO: 1, and the antisense strand may comprise the nucleotide sequence of SEQ ID NO: 2. In some embodiments, the sense strand may comprise the nucleotide sequence of SEQ ID NO: 1, and the antisense strand may comprise a nucleotide sequence having at least 60% (such as, e.g., 65%, 70%, 75%, 80%, 85%, 90%, 95%, 96%, 97%, 98%, or 99%) identity to SEQ ID NO: 2.

In various embodiments, the sense strand may comprise at least 11 contiguous nucleotides differing by no more than 8 nucleotides from SEQ ID NO: 1, and the antisense strand may comprise at least 11 contiguous nucleotides differing by no more than 8 nucleotides from SEQ ID NO: 2. In some embodiments, the sense strand may comprise at least 15 contiguous nucleotides differing by no more than 4 nucleotides from SEQ ID NO: 1; wherein the antisense strand may comprise at least 15 contiguous nucleotides differing by no more than 4 nucleotides from SEQ ID NO: 2.

In some embodiments, the sense strand may comprise the nucleotide sequence of SEQ ID NO: 1 or a sense sequence chosen from Tables 1 and 3. In some embodiments, the antisense strand may comprise the nucleotide sequence of SEQ ID NO: 2 or an antisense sequence chosen from Tables 2 and 3. In some embodiments, the sense strand may comprise the nucleotide sequence of SEQ ID NO: 1, and the antisense strand may comprise the nucleotide of SEQ ID NO: 2.

In some embodiments, at least one of the sense and antisense strands further may comprise at least one nucleotide overhangs at at least one end of the strand. In some embodiments, at least one of the sense and antisense strands further may comprise two nucleotide overhangs at 3'-end of the strand. In some embodiments, the sense strand may comprise the nucleotide sequence of 5'-GGAUUUAU-GUGGGCAUCAUdTdT-3' (SEQ ID NO: 3); and the antisense strand molecule may comprise the nucleotide sequence of 5'-AUGAUGCCCACAUAAAUCCdTdT-3' (SEQ ID NO: 4).

In additional embodiments, at least one strand of the siRNA may comprise at least one chemical modification chosen from end modifications, base modifications, sugar modifications, and backbone modifications. In some embodiments, at least one strand of the siRNA may comprise at least one chemical modification chosen from:
  (a) a phosphorothioate modification in the phosphate backbone;
  (b) 2'-O-methyl modification in a ribose or deoxyribose;
  (c) 2'-deoxy-2'-fluoro modification in a ribose or deoxyribose;
  (d) a locked nucleic acid (LNA) modification;
  (e) an open-loop nucleic acid modification;
  (f) an indole modification;
  (g) a 5-methylcytosine modification in a base;
  (h) a 5-ethynyluracil modification in a base;
  (i) a terminal nucleotide linked to a cholesteryl derivative;
  (j) a terminal nucleotide linked to a galactose;
  (k) a terminal nucleotide linked to a polypeptide;
  (l) a phosphorylation modification;
  (m) a terminal nucleotide linked to a fluorescent marker; and
  (n) a terminal nucleotide linked to a biotin molecule.

In some embodiments, the sense strand may comprise the nucleotide sequence 5'-K-LLMUUUAUGUGGGCAUP-MQdTdT-3' (SEQ ID NO: 13), and the antisense strand may comprise the nucleotide sequence 5'-R-MQLAUGCCCA-CAUAAAQPPdTdT-3' (SEQ ID NO: 14), wherein
  K is an optional cholesterol group linked to a 5'-end nucleotide;
  R is an optional phosphorylation modification on a 5'-end nucleotide;
  dT is a thymine deoxyribonucleotide;
  L is an unmodified or 2'-O-methyl modified guanine deoxyribonucleotide;
  M is an unmodified or 2'-O-methyl modified adenine deoxyribonucleotides;
  P is an unmodified or 2'-O-methyl modified cytosine deoxyribonucleotide;
  Q is an unmodified or 2'-O-methyl modified uracil ribonucleotide; and
  optionally, at least one of L, M, P, and Q has a phosphorothioate backbone.

In some embodiments, at least one of L, M, P, and Q may have a phosphorothioate backbone. In some embodiments, all of L, M, P, and Q may have a phosphorothioate backbone. In some embodiments, the sense strand may comprise a sense sequence chosen from Table 7, and the antisense strand may comprise an antisense sequence chosen from Table 7.

Further aspects of the disclosure provide a double-stranded siRNA targeted against ADAM17 comprising a sense strand and a complementary antisense strand. In some embodiments, the antisense strand may hybridize with an ADAM17 mRNA, and the sense strand may hybridize with the antisense strand.

In some embodiments, the sense strand may comprise a nucleotide sequence having at least 60% identity to 5'-GCAUCAUGUAUCUGAACAA-3' (SEQ ID NO: 7), and the antisense strand may comprise a nucleotide sequence having at least 60% identity to 5'-UUGUUCA-GAUACAUGAUGC-3' (SEQ ID NO: 8). In some embodiments, the sense strand may comprise a nucleotide sequence having at least 65%, 70%, 75%, 80%, 85%, 90%, 95%, 96%, 97%, 98%, or 99% identity to SEQ ID NO: 7, and the antisense strand may comprise a nucleotide sequence having at least 65%, 70%, 75%, 80%, 85%, 90%, 95%, 96%, 97%, 98%, or 99% identity to SEQ ID NO: 8. In some embodiments, wherein the sense strand may comprise a nucleotide sequence having at least 60% (such as, e.g., 65%, 70%, 75%, 80%, 85%, 90%, 95%, 96%, 97%, 98%, or 99%) identity to SEQ ID NO: 7, and the antisense strand may comprise the nucleotide sequence of SEQ ID NO: 8. In some embodiments, the sense strand may comprise the nucleotide sequence of SEQ ID NO: 7, and the antisense strand may comprise a nucleotide sequence having at least 60% (such as, e.g., 65%, 70%, 75%, 80%, 85%, 90%, 95%, 96%, 97%, 98%, or 99%) identity to SEQ ID NO: 8.

In various embodiments, the sense strand comprising at least 11 contiguous nucleotides differing by no more than 8 nucleotides from SEQ ID NO: 7, and the antisense strand comprising at least 11 contiguous nucleotides differing by no more than 8 nucleotides from SEQ ID NO: 8. In some embodiments, the sense strand may comprise at least 15 contiguous nucleotides differing by no more than 4 nucleotides from SEQ ID NO: 7; wherein the antisense strand may comprise at least 15 contiguous nucleotides differing by no more than 4 nucleotides from SEQ ID NO: 8. In some embodiments, the sense strand may comprise the nucleotide sequence of SEQ ID NO: 7 or a sense sequence chosen from Tables 8 and 10. In some embodiments, the antisense strand may comprise the nucleotide sequence of SEQ ID NO: 8 or the antisense sequence chosen from Tables 9 and 10. In some embodiments, the sense strand may comprise the nucleotide sequence of SEQ ID NO: 7, and the antisense strand may comprise the nucleotide of SEQ ID NO: 8.

In some embodiments, at least one of the sense and antisense strands further may comprise at least one nucleotide overhangs at at least one end of the strand. In some embodiments, at least one of the sense and antisense strands further may comprise two nucleotide overhangs at 3'-end of the strand. In some embodiments, the sense strand may comprise the nucleotide sequence of 5'-GCAUCAU-GUAUCUGAACAAdTdT-3' (SEQ ID NO: 9); and the antisense strand molecule may comprise the nucleotide sequence of 5'-UUGUUCAGAUACAUGAUGCdTdT-3' (SEQ ID NO: 10).

In additional embodiments, at least one strand of the siRNA may comprise at least one chemical modification chosen from end modifications, base modifications, sugar modifications, and backbone modifications. In some embodiments, at least one strand of the siRNA may comprise at least one chemical modification chosen from:
(a) a phosphorothioate modification in the phosphate backbone;
(b) 2'-O-methyl modification in a ribose or deoxyribose;
(c) 2'-deoxy-2'-fluoro modification in a ribose or deoxyribose;
(d) a locked nucleic acid (LNA) modification;
(e) an open-loop nucleic acid modification;
(f) an indole modification;
(g) a 5-methylcytosine modification in a base;
(h) a 5-ethynyluracil modification in a base;
(i) a terminal nucleotide linked to a cholesteryl derivative;
(j) a terminal nucleotide linked to a galactose;
(k) a terminal nucleotide linked to a polypeptide;
(l) a phosphorylation modification;
(m) a terminal nucleotide linked to a fluorescent marker; and
(n) a terminal nucleotide linked to a biotin molecule.

In some embodiments, the sense strand may comprise the nucleotide sequence 5'-K'-L'P'M'UCAU-GUAUCUGAAP'M'M'dTdT-3' (SEQ ID NO: 15), and the antisense strand may comprise the nucleotide sequence 5'-R'-Q'Q'L'UUCAGAUACAUGAQ'L'P'dTdT-3' (SEQ ID NO: 16), wherein
K' is an optional cholesterol group linked to a 5'-end nucleotide;
R' is an optional phosphorylation modification on a 5'-end nucleotide;
dT is a thymine deoxyribonucleotide;
L' is an unmodified or 2'-O-methyl modified guanine deoxyribonucleotide;
M' is an unmodified or 2'-O-methyl modified adenine deoxyribonucleotides;
P' is an unmodified or 2'-O-methyl modified cytosine deoxyribonucleotide; and
Q' is an unmodified or 2'-O-methyl modified uracil ribonucleotide; and
optionally, at least one of L', M', P', and Q' has a phosphorothioate backbone.

In some embodiments, at least one of L', M', P', and Q' may have a phosphorothioate backbone. In some embodiments, all of L', M', P', and Q' may have a phosphorothioate backbone. In some embodiments, the sense strand may comprise a sense sequence chosen from Table 13, and the antisense strand may comprise an antisense sequence chosen from Table 13.

Additional embodiments of the disclosure include a nucleic acid encoding the siRNA described herein. In some embodiments, the nucleic acid may be a DNA molecule. In some embodiments, the DNA molecule may comprise a nucleotide sequence having nucleotides 36-54 of 5'-GATC-CCCATGATGCCCACATAAATCCTTCAAGAGAG-GATTT ATGTGGGCATCATTTTTT' (SEQ ID NO: 6). In some embodiments, the DNA molecule comprise the nucleotide sequence of SEQ ID NO: 6. In some embodiments, the DNA molecule may comprise a nucleotide sequence having nucleotides 38-56 of 5'-AGCTAAAAAT-TGTTC AGATACATGATGCTCTCTTGAAGCATCATG-TATCTGAACAAGGG-3' (SEQ ID NO: 11). In some embodiments, the DNA molecule may comprise the nucleotide sequence of SEQ ID NO: 11.

Additional aspects of the disclosure include a pharmaceutical composition comprising the siRNAsdescribed herein, or the nucleic acid described herein, and optionally a pharmaceutically acceptable carrier, diluent, or excipient. In some embodiments, the pharmaceutical composition may comprise at least one siRNA targeted against ADAMTS-5, and at least one siRNA targeted against ADAM17.

Additional aspects of the disclosure also include a kit comprising the siRNA of described herein, the nucleic acid described herein, or the pharmaceutical composition described herein.

Further aspects of the disclosure provide use of the siRNA described herein, the nucleic acid described herein, or the pharmaceutical composition described herein in the preparation of a medicament for preventing and/or treating an ADAMTS-5 or ADAM17-associated disease. In various embodiments, the use may also include preparation of a medicament for inhibiting articular fibrosis, inhibiting cartilage erosion, preventing and/or treating synovitis, or protecting cartilage and/or synovium. In some embodiments, the ADAMTS-5 or ADAM17-associated disease may be an inflammation-related disease. In some embodiments, the inflammation-related disease may be arthritis. In some embodiments, the arthritis is osteoarthritis. In some embodiments, the arthritis may be rheumatoid arthritis.

Further aspects of the disclosure provide method of preventing and/or treating an ADAMTS-5 or ADAM17-associated disease in a subject, the method comprising administrating a therapeutically effective amount of the siRNA described herein, the nucleic acid described herein, or the pharmaceutical composition described herein to the subject. In various embodiments, the method may also include inhibiting articular fibrosis, inhibiting cartilage erosion, preventing and/or treating synovitis, or protecting cartilage and/or synovium in a subject. In some embodiments, the subject suffers from or has a risk of developing an ADAMTS-5 or ADAM17-associated disease. In some embodiments, the administration may comprise the administration comprising joint or intra-articular injection. In some embodiments, the administration may comprise injection into an articular cavity of the subject. In some embodiments, the ADAMTS-5 or ADAM17-associated disease may be an inflammation-related disease. In some embodiments, the inflammation-related disease may be arthritis. In some embodiments, the arthritis may be osteoarthritis. In some embodiments, the arthritis may be rheumatoid arthritis. In some embodiments, the subject may be a human.

Additional aspects of the disclosure also include a method of inhibiting the expression of ADAMTS-5 or ADAM17 in a cell, comprising contacting a cell with the siRNAs described herein in an effective amount to inhibit the expression of ADAMTS-5 or ADAM17 in the cell. Certain aspects of the disclosure further include a method of inhibiting the expression of an inflammatory cytokine in a cell, comprising contacting a cell with the siRNAs described herein in an effective amount to inhibit the expression of the inflammatory cytokine in the cell. In some embodiments, the inflammatory cytokine may be chosen from TNF, COX-2, and IL-1β. In some embodiments, the contacting may be practiced ex vivo or in vivo. In some embodiments, the cell may be a mammalian cell. In some embodiments, the cell may be a human cell.

DETAILED DESCRIPTION

I. Definitions

Figure 1:
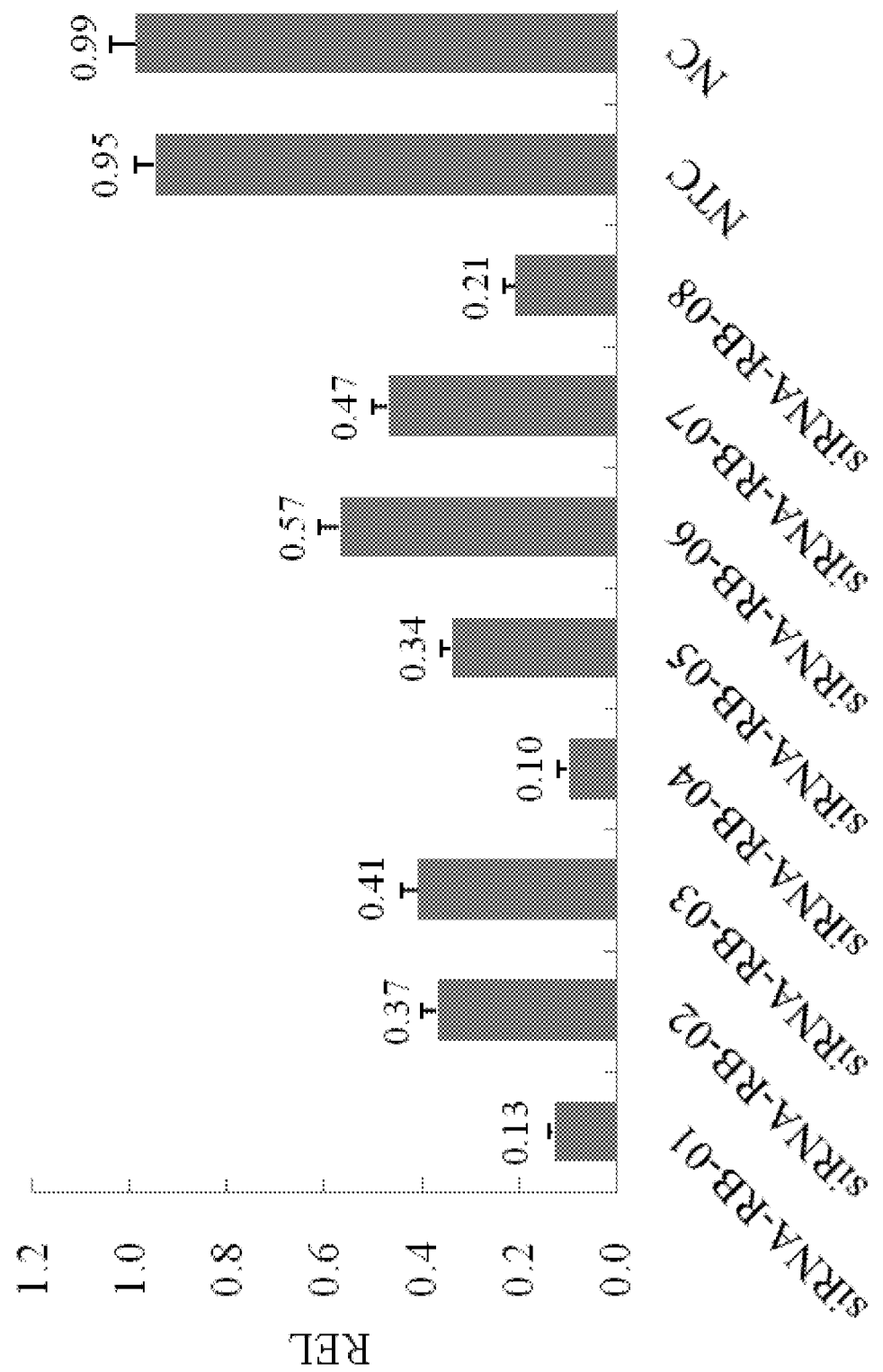
FIG. 1 shows the results of siRNA screening for inhibiting the expression of ADAMTS-5.

Unless defined otherwise, all technical and scientific terms used herein have the same meaning as commonly understood by those of ordinary skill in the art to which the disclosure belongs. For the purposes of the present disclosure, the following terms are defined below.

The articles "a" and "an" refer to one or to more than one (i.e., to at least one) of the grammatical object of the article. For example, "an element" means one element or more than one element.

The term "or" means, and is used interchangeably with, the term "and/or," unless context clearly indicates otherwise.

To the extent that the term "contain," "include," "have," or grammatical variants of such term are used in either the disclosure or the claims, such term can be inclusive in a manner similar to the term "comprising" as "comprising" is interpreted when employed as a transitional word in a claim. The term "including" or its grammatical variants mean, and are used interchangeably with, the phrase "including but not limited to."

The term "about" means a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight or length. When the term "about" is used in conjunction with a numerical range, it modifies that range by extending the boundaries above and below the numerical values set forth. In general, the term "about" is intended to modify a numerical value above and below the stated value by a variance of ≤10%.

As used herein, "ADAMTS-5" refers to a disintegrin and metalloproteinase with thrombospondin motifs 5. The term "ADAMTS-5" includes human ADAMTS-5, the mRNA sequence of which may be found in, e.g., GenBank Accession No. NM_007038.3 (SEQ ID NO: 191); rat ADAMTS-5, the mRNA sequence of which may be found in, e.g., GenBank Accession No. NM_198761.1 (SEQ ID NO: 192); mouse ADAMTS-5, the mRNA sequence of which may be found in, e.g., GenBank Accession No. NM_011782 (SEQ ID NO: 193). Additional examples of ADAMTS-5 mRNA sequences are readily available using, e.g., GenBank.

As used herein, "ADAM17" refers to a disintegrin and metalloproteinase domain-containing protein 17, also known as tumor necrosis factor-α-converting enzyme (TACE). The term "ADAM17" includes human ADAM17, the mRNA sequence of which may be found in, e.g., GenBank Accession No. NM_003183 (SEQ ID NO: 194); rat ADAM17, the mRNA sequence of which may be found in, e.g., GenBank Accession No. NM_020306 (SEQ ID NO: 195); mouse ADAM17, the mRNA sequence of which may be found in, e.g., GenBank Accession No. NM_001277266 (SEQ ID NO: 196), NM_001291871 (SEQ ID NO: 197), or NM_009615 (SEQ ID NO: 198). Additional examples of ADAM17 mRNA sequences are readily available using, e.g., GenBank.

The term "target sequence" refers to a contiguous portion of the nucleotide sequence of an RNA molecule formed during the transcription of a target gene, e.g., an ADAMTS-5 or ADAM17 gene, including mRNA produced by RNA processing of a primary transcription product. In various embodiments, the target sequence may comprise 10-30 contiguous nucleotides of an ADAMTS-5 or ADAM17 mRNA, such as, e.g., 10-25 or 15-20 contiguous nucleotides of the mRNA. In some embodiments, the target sequence may comprise 11, 13, 15, 17, 19, 21, 23, 25, or 27 contiguous nucleotides of the mRNA. In some embodiments, the target sequence may comprise 19 contiguous nucleotides of the mRNA.

The term "complementary" means that a nucleic acid can hybridize via hydrogen bond and form a duplex structure with another nucleic acid sequence under certain conditions. Such conditions may include, e.g., stringent conditions. The term "stringent conditions" for hybridization refer to conditions under which a nucleic acid having complementarity to a target sequence predominantly hybridizes with the target sequence, and substantially does not hybridize to non-target sequences. Stringent conditions are sequence-dependent and vary depending on a number of factors. For example, the longer the sequence, the higher the temperature at which the sequence may hybridize to its target sequence. Non-limiting examples of stringent conditions may include: 400 mM NaCl, 40 mM PIPES, pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides. The hybridization may be mediated by Watson-Crick base pairing or non-Watson-Crick base pairing, or base pairing formed with non-natural or modified nucleotides, as long as the above requirements with respect to their ability to hybridize are fulfilled. Examples of non-Watson-Crick base pairing include G:U wobble or Hoogstein base pairing. In certain embodiments, the hybridization between a nucleic acid molecule and its complementary sequence is sufficient to allow the relevant function of the nucleic acid to proceed, e.g., RNAi activity.

In some embodiments, the two nucleotide sequences are "fully complementary" with each other when all the contiguous nucleotides of the first nucleotide sequence base pairs with the same number of contiguous nucleotides of the second nucleotide sequence. "Substantially complementary" means that the two sequences may be fully complementary, or they may form one or more mismatched base pairs upon hybridization, while retaining the ability to hybridize under the conditions most relevant to their ultimate application. In some embodiments, the two sequences form no more than 6 mismatches upon hybridization. For example, the two sequences may form no more than 4, 3, 2, or 1 mismatch. Where two sequences are designed to form one or more single-stranded nucleotide overhangs upon hybridization, such overhangs shall not be regarded as mismatches for determining complementarity. For example, one oligonucleotide having 19 nucleotides in length and another oligonucleotide having 23 nucleotides in length, wherein the longer oligonucleotide comprises a sequence of 19 nucleotides that is fully complementary to the shorter oligonucleotide, may yet be referred to as "fully complementary" for the purposes of this disclosure.

The term "sequence identity" (e.g. a "sequence having 50% identity to") refers to the extent that a sequence is identical on a nucleotide-by-nucleotide basis over a window of comparison (i.e., the entire sequence of a reference sequence). A "percentage identity" (or "% identity") may be calculated by comparing two optimally aligned sequences over the window of comparison, determining the number of positions at which the identical nucleic acid base (e.g., A, T, C, G, U) occurs in both sequences to yield the number of matched positions, dividing the number of matched positions by the total number of positions in the window of comparison (i.e., the full length of the reference sequence), and multiplying the result by 100 to yield the percentage of sequence identity. Optimal alignment of sequences for aligning a comparison window may be conducted by computerized implementations of algorithms available in the art, such as, e.g., the BLAST® family of programs, or by inspection and the best alignment (i.e., resulting in the highest percentage homology over the comparison window) generated by any of the various methods selected. Thus, the term "sequence identity" refers to the ratio of the number of identical nucleotides to the reference sequence when those identical sequences are compared with the entire sequence of the reference sequence. Sequence identity between chemically-modified siRNA sequences is calculated by comparing the corresponding unmodified nucleotide sequences. For example, if a single-stranded RNA has 15 nucleotides in length, including 14 contiguous or non-contiguous nucleotides identical to a reference RNA sequence having 19 nucleotides, the identity between the two RNA sequences is 74% (14nt/19nt). By way of another example, if a single-stranded RNA has 23 nucleotides in length and the reference RNA sequence has 19 nucleotides in length, and the longer RNA comprises 19 contiguous or non-contiguous nucleotides identical to the shorter reference RNA sequence, the longer RNA sequence may be said to "contain" the short reference RNA sequence. In other words, a reference sequence may be interrupted by insertions or deletions as well as with substitutions in calculating percentage identity.

"G," "C," "A," and "U" each stand for guanine, cytosine, adenine, and uracil nucleotide bases, respectively. "T" and "dT" are used interchangeably and refer to a deoxyribonucleotide of which the nucleobase contains thymine, such as, e.g., deoxyribothymine, 2'-deoxythymidine, or thymidine. The term "nucleotide" or "ribonucleotide" or "deoxyribonucleotide" refers to a natural nucleotide comprising a nucleobase, a sugar and at least one phosphate group (e.g., a phosphodiester linking group). These terms can also refer to a modified nucleotide, e.g., a chemically-modified nucleotide, or a surrogate replacement moiety. Guanine, cytosine, adenine, and uracil may be replaced by other moieties without substantially altering the base pairing properties of an oligonucleotide comprising a nucleotide bearing such replacement moiety. For example, a nucleotide comprising inosine as its base may base pair with nucleotides containing adenine, cytosine, or uracil. Hence, nucleotides containing uracil, guanine, or adenine in the nucleotide sequences described herein may be replaced by a nucleotide containing, e.g., inosine. And cytosine anywhere in the nucleotide sequences described herein may be replaced with guanine or uracil.

The term "nucleobase" or "base" are used interchangeably to refer to a purine or pyrimidine base found in natural DNA or RNA (e.g., uracil, thymine, adenine, cytosine, and guanine). The terms also include analogs or modified counterparts of these natural purines and pyrimidines, which may confer improved properties to the nucleic acid molecule.

The term "short interfering RNA" or "siRNA" refers to any nucleic acid molecule capable of inhibiting or down-regulating gene expression, e.g., by mediating sequence-specific degradation of an RNA transcript, e.g., an mRNA, through RNAi or gene silencing. In some embodiments, the siRNA can be a double-stranded polynucleotide molecule comprising self-complementary sense and antisense regions. The antisense region comprises a nucleotide sequence that is complementary to the nucleotide sequence in a target nucleic acid molecule (e.g., an ADAMTS-5 or ADAM17 mRNA) or a portion thereof (e.g., a target sequence or a portion thereof), and the sense region comprises a nucleotide sequence corresponding to the target sequence or a portion thereof. In some embodiments, the siRNA can be assembled from two separate oligonucleotides and comprise a sense strand and an antisense strand, wherein the antisense and sense strands are complementary, i.e. each strand comprises a nucleotide sequence that is complementary to a nucleotide sequence in the other strand such that the antisense strand and sense strand form a duplex or double-stranded structure. The antisense strand comprises a nucleotide sequence that is complementary to a nucleotide sequence in a target nucleic acid molecule (e.g., an ADAMTS-5 or ADAM17 mRNA) or a portion thereof (e.g., a target sequence or a portion thereof), and the sense strand comprises a nucleotide sequence corresponding to the target sequence or a portion thereof. In some embodiments, the siRNA can also be assembled from a single oligonucleotide, wherein the self-complementary sense and antisense regions of the siRNA are linked by a nucleotide based or non-nucleotide based linker(s). In some embodiments, the siRNA can be a polynucleotide having a duplex, asymmetric duplex, hairpin, or asymmetric hairpin secondary structure. In some embodiments, the siRNA can be a circular single-stranded polynucleotide having two or more loop structures and a stem comprising self-complementary sense and antisense regions. The circular polynucleotide can be processed either in vivo or in vitro to generate an active siRNA molecule capable of mediating RNAi. In some embodiments, the siRNA can also comprise a single-stranded polynucleotide having nucleotide sequence complementary to a nucleotide sequence in a target nucleic acid molecule or a portion thereof (e.g., an ADAMTS-5 or ADAM17 mRNA), where such siRNA molecule does not require the presence within the siRNA molecule of a nucleotide sequence corresponding to the target sequence or a portion thereof.

In certain embodiments, the siRNA molecules need not be limited to those molecules containing only natural nucleotides, but further encompasses modified nucleotides and non-nucleotides. For example, the majority of nucleotides of each strand of an siRNA molecule are ribonucleotides, but as described in detail below, each or both strands can also include one or more non-ribonucleotides, e.g., a deoxyribonucleotide, and/or a modified nucleotide, e.g., a chemically-modified nucleotide. In some embodiments, the siRNA molecules may include chemical modifications at multiple nucleotides or multiple chemical modifications on a single nucleotide. Such modifications may include all types of modifications disclosed herein or known in the art.

The term "siRNA" can also include other terms used to describe nucleic acid molecules capable of mediating sequence-specific RNAi, e.g., double-stranded RNA (dsRNA), micro-RNA (miRNA), short hairpin RNA (shRNA), short interfering oligonucleotide, short interfering nucleic acid, short interfering modified oligonucleotide, chemically-modified siRNA, and post-transcriptional gene silencing RNA (ptgsRNA). In addition, the term "RNAi" can include other terms used to describe sequence-specific RNAi, such as post-transcriptional gene silencing, gene silencing, translational inhibition, or epigenetics. In some embodiments, the siRNA may modulate, e.g., inhibit, the expression of ADAMTS-5 or ADAM17 in a cell, e.g., a cell in a culture or a cell within a subject, such as, e.g., a mammalian subject, e.g., a human.

A "nucleotide overhang" refers to the unpaired nucleotide or nucleotides that protrude from the duplex structure of a double-stranded siRNA molecule when a 3'-end of one strand of the siRNA extends beyond the 5'-end of the other strand, or vice versa. "Blunt" or "blunt end" means that no unpaired nucleotides exist at that end of a double-stranded siRNA molecule, i.e., no nucleotide overhang. The siRNAs described herein include double-stranded siRNAs with nucleotide overhangs at one end, i.e., siRNAs with one overhang and one blunt end, or with nucleotide overhangs at both ends. The siRNAs described herein also include siRNA that is double-stranded over its entire length, i.e., no nucleotide overhang at either end of the molecule.

The term "modulate" means that the expression of the gene, or level of the mRNA molecule or equivalent RNA molecules encoding one or more proteins or protein subunits, or level or activity of one or more proteins or protein subunits is up-regulated or down-regulated, such that the expression, level, or activity is greater than or less than that observed in the absence of the modulator. For example, the term "modulate" can mean "inhibit," but the use of the word "modulate" is not limited to this definition.

The term "inhibit," "down-regulate," "reduce," "silence," "block," or "suppress," all used interchangeably, means that the expression of the gene, or level of the mRNA molecules or equivalent RNA molecules encoding one or more proteins or protein subunits, or level or activity of one or more proteins or protein subunits, is reduced below that observed in the presence of the nucleic acid molecules (e.g., siRNA) described herein. In certain embodiments, inhibition, down-regulation, reduction, silencing, blocking, or suppression with an siRNA molecule is below that level observed in the presence of an inactive or attenuated molecule. In another embodiment, inhibition, down-regulation, reduction, silencing, blocking, or suppression with an siRNA molecule is below that level observed in the presence of, for example, an siRNA molecule with a scrambled sequence or with mismatches (e.g., an siRNA molecule with a random non-specific sequence).

The phrase "inhibiting expression of ADAMTS-5" or "inhibiting expression of ADAM17" includes inhibition of expression of any ADAMTS-5 or ADAM17 gene (such as, e.g., a mouse gene, a rat gene, a monkey gene, or a human gene) as well as gene variants, (e.g., naturally-occurring variants), or mutants of an ADAMTS-5 or ADAM17 gene. Thus, the ADAMTS-5 or ADAM17 gene may be a wild-type gene, a variant gene, a mutant gene, or a transgenic gene in the context of a genetically manipulated cell, group of cells, or organism.

"Inhibiting expression of ADAMTS-5" or "inhibiting expression of ADAM17" includes any level of inhibition of the target gene, e.g., at least partial suppression of the expression of an ADAMTS-5 or ADAM17 gene. The expression of a target gene may be assessed based on the level of any variable associated with target gene expression, e.g., the mRNA level of ADAMTS-5 or ADAM17, protein level ADAMTS-5 or ADAM17, or levels of other immune factors including inflammatory cytokines functionally involved in ADAMTS-5- or ADAM17-associated disorders, such as, e.g., tumor necrosis factor (TNF, such as, e.g., TNF-α), cyclooxygenase (COX, such as, e.g., COX-2), and interleukin (IL, such as, e.g., IL-1β). Inhibition may be assessed by a decrease in an absolute of one or more of these variables or in a relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

The terms "contacting a cell," "introducing," or "delivering" include delivery of the oligomers of the disclosure into a cell by methods known in the art, e.g., transfection (e.g., via liposome, calcium-phosphate, polyethyleneimine), electroporation (e.g., nucleofection), or microinjection. The contacting includes contacting a cell in vitro or in vivo. Contacting a cell in vitro may be done, e.g., by incubating the cell with the siRNA. Contacting a cell in vivo may be done, e.g., by injecting the siRNA into or near the tissue where the cell is located, or by injecting the siRNA into another area, e.g., the bloodstream or the subcutaneous space, such that the siRNA will subsequently reach the tissue where the cell to be contacted is located.

The term a "subject" or a "subject in need thereof" includes a mammalian subject such as a human subject. Exemplary mammalian subjects suffer from or have a risk of developing an ADAMTS-5- or ADAM17-associated disease, such as, e.g., arthritis, including osteoarthritis and rheumatoid arthritis.

An "ADAMTS-5-associated disease" or "ADAM17-associated disease" includes any disorder, disease, or condition associated with the ADAMTS-5 or ADAM17 gene or the ADAMTS-5 or ADAM17 protein. Such a disease may be caused, for example, by ADAMTS-5 or ADAM17 gene variants or mutations, by misfolding of the ADAMTS-5 or ADAM17 protein, intracellular accumulation of the protein (e.g., misfolded protein), excess production of the protein, abnormal cleavage of the protein, abnormal interactions between ADAMTS-5 or ADAM17 and other proteins or other endogenous or exogenous substances. In some embodiments, the ADAMTS-5- or ADAM17-associated disease may be an inflammation-related disease. In some embodiments, the ADAMTS-5- or ADAM17-associated disease may be arthritis, such as, e.g., osteoarthritis, rheumatoid arthritis, chronic infectious arthritis, spondylitis, psoriatic arthritis, and gout. Exemplary conditions or symptoms of the ADAMTS-5- or ADAM17-associated disease include articular fibrosis, cartilage erosion, loss of cartilage collagen, damage of articular cartilage surfaces, synovitis, inflammation in joint capsules, join pain, thickening of joint ligaments, meniscus ossification, and disorganization of cartilage cells.

The term a "therapeutically effective amount" or "effective amount" of a compound or composition refers to an amount effective in the prevention or treatment of a disorder for the treatment of which the compound or composition is effective. The term includes the amount of an siRNA molecule that, when administered to a subject for treating an ADAMTS-5- or ADAM17-associated disease, is sufficient to effect treatment of the disease, e.g., by diminishing, ameliorating, or maintaining the existing disease or one or more symptoms of the disease, or by inhibiting the progression of the disease. The "therapeutically effective amount" or "effective amount" may vary depending on the siRNA molecule, the route of administration, the disease and its severity, and the health, age, weight, family history, genetic makeup, stage of pathological processes mediated by ADAMTS-5 or ADAM17 expression, the types of preceding or concomitant treatments, if any, and other individual characteristics of the subject to be treated.

In various embodiments, the term "treatment" includes treatment of a subject (e.g. a mammal, such as a human) or a cell to alter the current course of the subject or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition or the associated symptoms. In various embodiments, the term "treatment" may include relieving, slowing, or reversing the pathological processes or symptoms mediated by ADAMTS-5 or ADAM17 expression, such as, e.g., slowing the progression of arthritis, such as, e.g., osteoarthritis, rheumatoid arthritis, chronic infectious arthritis, spondylitis, psoriatic arthritis, and gout, or relieving symptoms, such as, e.g., articular fibrosis, cartilage erosion, loss of cartilage collagen, damage of articular cartilage surfaces, synovitis, inflammation in joint capsules, join pain, thickening of joint ligaments, meniscus ossification, and disorganization of cartilage cells.

The terms "administering," or "administer" include delivery of the siRNAs described herein to a subject either by local or systemic administration. Administration may be topical (including ophthalmic and to mucous membranes including vaginal and rectal delivery), pulmonary (e.g., by inhalation or insufflation of powders or aerosols, including by nebulizer, intratracheal, intranasal), epidermal, transdermal, oral, or parenteral. Parenteral administration includes intravenous, intraarterial, subcutaneous, intraperitoneal or intramuscular injection or infusion; intracranial, e.g., intrathecal or intraventricular, administration; or joint or intra-articular injection.

II. siRNA

Certain aspects of the disclosure provide siRNAs that inhibit the expression of an ADAMTS-5 or ADAM17 gene in vitro, such as e.g., in a solution or a cell-free system (e.g., a cell lysate or in a reconstituted system), or in a cell, such as, e.g., ex vivo in a cell in culture (e.g., a cell expressing ADAMTS-5 or ADAM17), or in vivo in a cell within a subject. The subject may be a mammal, such as, e.g., a rat, mouse, or human. In some embodiments, the subject may be a human. In some embodiments, the subject may suffer from an ADAMTS-5- or ADAM17-associated disease, such as, e.g., an inflammation-related disease, or have a risk of developing such disease. Exemplary inflammation-related diseases include, e.g., arthritis, including osteoarthritis, rheumatoid arthritis, chronic infectious arthritis, spondylitis, psoriatic arthritis, and gout. In some embodiments, the disease may be arthritis. In some embodiments, the disease may be osteoarthritis. In some embodiments, the disease may be rheumatoid arthritis.

The siRNAs may be said to be "directed to" or "targeted against" a target sequence with which it hybridizes. In various embodiments, the target sequence may comprise 10-30 contiguous nucleotides of an RNA transcript of an ADAMTS-5 or ADAM17 gene (e.g., a target mRNA), such as, e.g., 10-25 or 15-20 contiguous nucleotides of the target mRNA, including all integers in between these ranges. For example, the target sequence may comprise, 11, 13, 15, 17, 19, 21, 23, 25, or 27 contiguous nucleotides of the target mRNA. In some embodiments, the target sequence may comprise 19 contiguous nucleotides of the target mRNA. In various embodiments, the siRNAs described herein may comprise an antisense region having sufficient complementarity to a target mRNA sequence to carry out the RNAi activity. For example, the antisense region may comprise at least 11 contiguous or non-contiguous nucleotides complementary with the target mRNA sequence, such as, e.g., at least 15 contiguous or non-contiguous nucleotides complementary with the target mRNA sequence. In some embodiments, the antisense region may comprise 11, 13, 15, 17, 19, 21, 23, 25, or 27 contiguous or non-contiguous nucleotides complementary with the target mRNA sequence. In some embodiments, the antisense region may comprise 15 contiguous or non-contiguous nucleotides complementary with the target mRNA sequence. In some embodiments, the antisense region may comprise 17 contiguous or non-contiguous nucleotides complementary with the target mRNA sequence. In some embodiments, the antisense region may comprise 19 contiguous or non-contiguous nucleotides complementary with the target mRNA sequence. In some embodiments, the antisense region may be substantially complementary with at least part of an RNA transcript of an ADAMTS-5 or ADAM17 gene, such as e.g., an ADAMTS-5 or ADAM17 mRNA. In some embodiments, the antisense region may be fully complementary to at least part of the RNA transcript of the ADAMTS-5 or ADAM17 gene.

Various embodiments include single-stranded siRNAs, wherein the self-complementary sense and antisense regions of the siRNA may be linked by a nucleotide based or non-nucleotide-based linker(s). In some embodiments, the siRNA may be a single-stranded polynucleotide having a duplex, asymmetric duplex, hairpin, or asymmetric hairpin secondary structure. In some embodiments, the siRNA may be a circular single-stranded polynucleotide having two or more loop structures and a stem comprising self-complementary sense and antisense regions. In some embodiments, the circular polynucleotide can be processed either in vivo or in vitro to generate an active siRNA molecule capable of mediating RNAi. In some embodiments, the siRNA may comprise a single-stranded polynucleotide having an antisense region complementary to a target sequence (e.g., an ADAMTS-5 or ADAM17 mRNA or a portion thereof), where such siRNA molecule does not require the presence within the siRNA molecule of a sense region corresponding to the target sequence.

In some embodiments, the siRNA may be a double-stranded siRNA comprising a sense strand and an antisense strand. The antisense strand may comprise an antisense region of the siRNA. The sense strand and antisense strand of the siRNA may form a duplex structure. In some embodiments, the antisense strand may hybridize with an ADAMTS-5 mRNA, and the sense strand may hybridize with the antisense strand. In other embodiments, the antisense strand may hybridize with an ADAM17 mRNA, and the sense strand hybridizes with the antisense strand. In some embodiments, the duplex region of the RNAi may have at least 11 base pairs, such as, e.g., at least 15 base pairs, at least 17 base pairs, or at least 19 base pairs. For example, the duplex region of the RNAi may have 11, 13, 15, 17, 19, 21, 23, 25, or 27 base pairs. In some embodiments, the duplex region of the RNAi may have 15 base pairs. In some embodiments, the duplex region of the RNAi may have 17 base pairs. In some embodiments, the duplex region of the RNAi may have 19 base pairs.

Where the siRNA is a double-stranded molecule, each strand may have the same length or different lengths. In some embodiments, each strand of the siRNA, single-stranded or double stranded, may be 10-60 nucleotides in length. For example, each strand may be 10-50 nucleotides in length, 10-40 nucleotides in length, 10-30 nucleotides in length, 10-25 nucleotides in length, 10-20 nucleotides in length, 15-25 nucleotides in length, 15-27 nucleotides in length, or 15-20 nucleotides in length, including all integers in between these ranges. In some embodiments, each strand may be 15-27 nucleotides in length, including all integers in between these ranges. In some embodiments, each strand may be 11, 13, 15, 17, 19, 21, 23, 25, or 27 nucleotides in length. In some embodiments, each strand may be 15 nucleotides in length. In some embodiments, each strand may be 17 nucleotides in length. In some embodiments, each strand may be 19 nucleotides in length. When two or more different siRNA molecules are used in combination, the lengths of each strand of each siRNA can be identical or can be different. For the purpose of this disclosure, length calculation of any double-stranded siRNA strands shall exclude any nucleotide overhangs that may be present.

Nucleotide insertions, substitutions, deletions, or mismatches may be possible in the siRNAs described herein by methods known in the art. For example, nucleotides containing uracil, guanine, or adenine in the nucleotide sequences described herein may be replaced by a nucleotide containing, e.g., inosine. Cytosine anywhere in the nucleotide sequences described herein may be replaced with guanine or uracil. In some embodiments, the siRNA may comprise an antisense sequence comprising SEQ ID NO: 2, 4, 8, or 10 or chosen from Tables 2, 3, 9, and 10, having 1, 2, 3, 4, 5, 6, 7, or 8 nucleotide insertions, substitutions, deletions, or mismatches. In some embodiments, the siRNA may further comprise a sense sequence comprising SEQ ID NO: 1, 3, 7, or 9 or chosen from Tables 1, 3, 8, and 10, having 1, 2, 3, 4, 5, 6, 7, or 8 nucleotide insertions, substitutions, deletions, or mismatches. In some embodiments, the siRNA may comprise an antisense sequence comprising SEQ ID NO: 2, 4, 8, or 10 or chosen from Tables 2, 3, 9, and 10, having 1, 2, 3, or 4 nucleotide insertions, substitutions, deletions, or mismatches. In some embodiments, the siRNA may further comprise a sense sequence comprising SEQ ID NO: 1, 3, 7, or 9 or chosen from Tables 1, 3, 8, and 10, having 1, 2, 3, or 4 nucleotide insertions, substitutions, deletions, or mismatches. In some embodiments, the siRNA may comprise an antisense sequence comprising SEQ ID NO: 2 having 1, 2, 3, or 4 nucleotide insertions, substitutions, deletions, or mismatches. In some embodiments, the siRNA may further comprise a sense sequence comprising SEQ ID NO: 1 having 1, 2, 3, or 4 nucleotide insertions, substitutions, deletions, or mismatches. In some embodiments, the siRNA may comprise an antisense sequence comprising SEQ ID NO: 8 having 1, 2, 3, or 4 nucleotide insertions, substitutions, deletions, or mismatches. In some embodiments, the siRNA may further comprise a sense sequence comprising SEQ ID NO: 7 having 1, 2, 3, or 4 nucleotide insertions, substitutions, deletions, or mismatches.

In some embodiments, the siRNA may comprise an antisense sequence comprising at least 11, such as, e.g., at least 15 or at least 19, contiguous nucleotides differing by no more than 8 nucleotides from an antisense sequence chosen from Tables 1, 3, 8, and 10. In some embodiments, the siRNA may comprise an antisense sequence comprising at least 11, such as, e.g., at least 15 or at least 19, contiguous nucleotides differing by no more than 4 nucleotides from an antisense sequence chosen from Tables 1, 3, 8, and 10. In some embodiments, the siRNA may further comprise a sense sequence comprising at least 11, such as, e.g., at least 15 or at least 19, contiguous nucleotides differing by no more than 8 nucleotides from a sense sequence chosen from Tables 2, 3, 9, and 10. In some embodiments, the siRNA may further comprise a sense sequence comprising at least 11, such as, e.g., at least 15 or at least 19, contiguous nucleotides differing by no more than 4 nucleotides from a sense sequence chosen from Tables 2, 3, 9, and 10.

Embodiments of the siRNAs may comprise a nucleotide sequence having certain sequence identity to the nucleotide sequences disclosed herein, such as, e.g., the nucleotide sequences of SEQ ID NOs: 1-4 and 7-10 and those disclosed in Tables 1-3 (SEQ ID NOs: 17-49) and 8-10 (SEQ ID NOs: 98-128). For example, the siRNA may comprise a nucleotide sequence having at least 60%, such as, e.g., at least 70%, at least 80%, at least 90%, at least 95%, or higher identity to any one of the disclosed sequences. In some embodiments, the siRNA may comprise a nucleotide sequence having at least 60%, 65%, 70%, 75%, 80%, 85%, 90%, 95%, 96%, 97%, 98%, or 99% identity to any one of the disclosed sequences.

Exemplary siRNAs targeted against ADAMTS-5 may comprise an antisense sequence having at least 60% (such as, e.g., 65%, 70%, 75%, 80%, 85%, 90%, 95%, 96%, 97%, 98%, or 99%) identity to SEQ ID NO: 2 or 4 or to an antisense sequence chosen from Tables 2 and 3. In some embodiments, the siRNA may further comprise a sense sequence having at least 60% (such as, e.g., 65%, 70%, 75%, 80%, 85%, 90%, 95%, 96%, 97%, 98%, or 99%) identity to SEQ ID NO: 1 or 3 or to a sense sequence chosen from Tables 1 and 3.

In some embodiments, the siRNA may comprise an antisense sequence having at least 60% (such as, e.g., 65%, 70%, 75%, 80%, 85%, 90%, 95%, 96%, 97%, 98%, or 99%) identity to SEQ ID NO: 2. In some embodiments, the siRNA may further comprise a sense sequence having at least 60% (such as, e.g., 65%, 70%, 75%, 80%, 85%, 90%, 95%, 96%, 97%, 98%, or 99%) identity to SEQ ID NO: 1. In some embodiments, the siRNA may comprise an antisense sequence comprising the nucleotide sequence of SEQ ID NO: 2. In some embodiments, the siRNA may further comprise a sense sequence comprising the nucleotide sequence of SEQ ID NO: 1. In some embodiments, the siRNA may comprise an antisense sequence having at least 60% (such as, e.g., 65%, 70%, 75%, 80%, 85%, 90%, 95%, 96%, 97%, 98%, or 99%) identity to SEQ ID NO: 2, and a sense sequence comprising the nucleotide sequence of SEQ ID NO: 1. In some embodiments, the siRNA may comprise an antisense sequence comprising the nucleotide sequence of SEQ ID NO: 2, and a sense sequence having at least 60% (such as, e.g., 65%, 70%, 75%, 80%, 85%, 90%, 95%, 96%, 97%, 98%, or 99%) identity to SEQ ID NO: 1.

In some embodiments, the siRNA may comprise an antisense sequence having at least 60% (such as, e.g., 65%, 70%, 75%, 80%, 85%, 90%, 95%, 96%, 97%, 98%, or 99%) identity to SEQ ID NO: 4. In some embodiments, the siRNA may further comprise a sense sequence having at least 60% (such as, e.g., 65%, 70%, 75%, 80%, 85%, 90%, 95%, 96%, 97%, 98%, or 99%) identity to SEQ ID NO: 3. In some embodiments, the siRNA may comprise an antisense sequence comprising the nucleotide sequence of SEQ ID NO: 4. In some embodiments, the siRNA may further comprise a sense sequence comprising the nucleotide sequence of SEQ ID NO: 3. In some embodiments, the siRNA may comprise an antisense sequence having at least 60% (such as, e.g., 65%, 70%, 75%, 80%, 85%, 90%, 95%, 96%, 97%, 98%, or 99%) identity to SEQ ID NO: 4, and a sense sequence comprising the nucleotide sequence of SEQ ID NO: 3. In some embodiments, the siRNA may comprise an antisense sequence comprising the nucleotide sequence of SEQ ID NO: 4, and a sense sequence having at least 60% (such as, e.g., 65%, 70%, 75%, 80%, 85%, 90%, 95%, 96%, 97%, 98%, or 99%) identity to SEQ ID NO: 3.

In some embodiments, the siRNA may comprise an antisense sequence having at least 60% (such as, e.g., 65%, 70%, 75%, 80%, 85%, 90%, 95%, 96%, 97%, 98%, or 99%) identity to an antisense sequence chosen from Tables 2 and 3. In some embodiments, the siRNA may further comprise a sense sequence having at least 60% (such as, e.g., 65%, 70%, 75%, 80%, 85%, 90%, 95%, 96%, 97%, 98%, or 99%) identity to a sense sequence chosen from Tables 1 and 3. In some embodiments, the siRNA may comprise an antisense sequence chosen from Tables 2 and 3. In some embodiments, the siRNA may further comprise a sense sequence chosen from Tables 1 and 3. In some embodiments, the siRNA may comprise an antisense sequence having at least 60% (such as, e.g., 65%, 70%, 75%, 80%, 85%, 90%, 95%, 96%, 97%, 98%, or 99%) identity to an antisense sequence chosen from Tables 2 and 3, and a sense sequence chosen from Tables 1 and 3. In some embodiments, the siRNA may comprise an antisense sequence chosen from Tables 2 and 3, and a sense sequence having at least 60% (such as, e.g., 65%, 70%, 75%, 80%, 85%, 90%, 95%, 96%, 97%, 98%, or 99%) identity to a sense sequence chosen from Tables 1 and 3.

Exemplary siRNAs targeted against ADAM17 may comprise an antisense sequence having at least 60% (such as, e.g., 65%, 70%, 75%, 80%, 85%, 90%, 95%, 96%, 97%, 98%, or 99%) identity to SEQ ID NO: 8 or 10 or to an antisense sequence chosen from Tables 9 and 10. In some embodiments, the siRNA may further comprise a sense sequence having at least 60% (such as, e.g., 65%, 70%, 75%, 80%, 85%, 90%, 95%, 96%, 97%, 98%, or 99%) identity to SEQ ID NO: 7 or 9 or to a sense sequence chosen from Tables 8 and 10.

In some embodiments, the siRNA may comprise an antisense sequence having at least 60% (such as, e.g., 65%, 70%, 75%, 80%, 85%, 90%, 95%, 96%, 97%, 98%, or 99%) identity to SEQ ID NO: 8. In some embodiments, the siRNA may further comprise a sense sequence having at least 60% (such as, e.g., 65%, 70%, 75%, 80%, 85%, 90%, 95%, 96%, 97%, 98%, or 99%) identity to SEQ ID NO: 7. In some embodiments, the siRNA may comprise an antisense sequence comprising the nucleotide sequence of SEQ ID NO: 8. In some embodiments, the siRNA may further comprise a sense sequence comprising the nucleotide sequence of SEQ ID NO: 7. In some embodiments, the siRNA may comprise an antisense sequence having at least 60% (such as, e.g., 65%, 70%, 75%, 80%, 85%, 90%, 95%, 96%, 97%, 98%, or 99%) identity to SEQ ID NO: 8, and a sense sequence comprising the nucleotide sequence of SEQ ID NO: 7. In some embodiments, the siRNA may comprise an antisense sequence comprising the nucleotide sequence of SEQ ID NO: 8, and a sense sequence having at least 60% (such as, e.g., 65%, 70%, 75%, 80%, 85%, 90%, 95%, 96%, 97%, 98%, or 99%) identity to SEQ ID NO: 7.

In some embodiments, the siRNA may comprise an antisense sequence having at least 60% (such as, e.g., 65%, 70%, 75%, 80%, 85%, 90%, 95%, 96%, 97%, 98%, or 99%) identity to SEQ ID NO: 10. In some embodiments, the siRNA may further comprise a sense sequence having at least 60% (such as, e.g., 65%, 70%, 75%, 80%, 85%, 90%, 95%, 96%, 97%, 98%, or 99%) identity to SEQ ID NO: 9. In some embodiments, the siRNA may comprise an antisense sequence comprising the nucleotide sequence of SEQ ID NO: 10. In some embodiments, the siRNA may further comprise a sense sequence comprising the nucleotide sequence of SEQ ID NO: 9. In some embodiments, the siRNA may comprise an antisense sequence having at least 60% (such as, e.g., 65%, 70%, 75%, 80%, 85%, 90%, 95%, 96%, 97%, 98%, or 99%) identity to SEQ ID NO: 10, and a sense sequence comprising the nucleotide sequence of SEQ ID NO: 9. In some embodiments, the siRNA may comprise an antisense sequence comprising the nucleotide sequence of SEQ ID NO: 10, and a sense sequence having at least 60% (such as, e.g., 65%, 70%, 75%, 80%, 85%, 90%, 95%, 96%, 97%, 98%, or 99%) identity to SEQ ID NO: 9.

In some embodiments, the siRNA may comprise an antisense sequence having at least 60% (such as, e.g., 65%, 70%, 75%, 80%, 85%, 90%, 95%, 96%, 97%, 98%, or 99%) identity to an antisense sequence chosen from Tables 9 and 10. In some embodiments, the siRNA may further comprise a sense sequence having at least 60% (such as, e.g., 65%, 70%, 75%, 80%, 85%, 90%, 95%, 96%, 97%, 98%, or 99%) identity to a sense sequence chosen from Tables 8 and 10. In some embodiments, the siRNA may comprise an antisense sequence chosen from Tables 9 and 10. In some embodiments, the siRNA may further comprise a sense sequence chosen from Tables 8 and 10. In some embodiments, the siRNA may comprise an antisense sequence having at least 60% (such as, e.g., 65%, 70%, 75%, 80%, 85%, 90%, 95%, 96%, 97%, 98%, or 99%) identity to an antisense sequence chosen from Tables 9 and 10, and a sense sequence chosen from Tables 8 and 10. In some embodiments, the siRNA may comprise an antisense sequence chosen from Tables 9 and 10, and a sense sequence having at least 60% (such as, e.g., 65%, 70%, 75%, 80%, 85%, 90%, 95%, 96%, 97%, 98%, or 99%) identity to a sense sequence chosen from Tables 8 and 10.

Certain embodiments of the double-stranded siRNA described herein may comprise one or more single-stranded nucleotide overhangs of one or more nucleotides at the 5'-end, 3'-end, or both ends of one or both strands. The nucleotide overhangs on each strand may be the same or different in terms of number, length, sequence, and location. For example, the nucleotide overhang may be located at the 3'-end of the sense strand, the antisense strand, or both strands. Accordingly, the siRNA may also have a blunt end, located at the 5'-end of the antisense strand (or the 3'-end of the sense strand) or vice versa. In some embodiments, the antisense strand of the siRNA may have a nucleotide overhang at the 3'-end and a blunt 5'-end. The overhang may form a mismatch with the target sequence or it may be complementary to the target sequence or may be another sequence. In some embodiments, at least one end of either strand of the siRNA may comprise a nucleotide overhang of 1-10 nucleotides in length, such as, e.g., 1-8, 2-8, 1-6, 2-6, 1-5, 2-5, 1-4, 2-4, 1-3, 2-3, or 1-2 nucleotides, including all integers in between these ranges. In some embodiments, the nucleotide overhang may have 1 or 2 nucleotides in length. In various embodiments, the nucleotides in the overhang may each independently be an unmodified nucleotide or a modified nucleotide as disclosed herein or known in the art. For example, the nucleotide overhang may comprise at least one deoxythemine (dT). In some embodiments, the nucleotide overhang may be dTdT. In some embodiments, the antisense strand of the siRNA may have dTdT at the 3'-end. In some embodiments, the sense strand of the siRNA may have dTdT at the 3'-end. In some embodiments, both strands of the siRNA may have dTdT at the 3'-end. When two or more different siRNA molecules are used in combination, each siRNA may have the same or different overhang architectures. For example, the number, length, sequence, and location of the nucleotide overhang on each strand may be independently selected.

III. Chemical Modifications

In various embodiments, the siRNA may be chemically modified to enhance activity (e.g., stability, efficacy, and specificity), cellular distribution or cellular uptake, or other properties of the siRNA. The siRNAs disclosed herein may be synthesized and/or modified by methods well established in the art. Various embodiments of the siRNA may comprise at least one modified nucleotide (such as, e.g., by chemically modification, conjugation, or substitution) with any suitable group for improving the properties of the siRNA. It is unnecessary for all positions in a given siRNA to be uniformly modified. In some embodiment, more than one modifications may be incorporated in a single siRNA or at a single nucleoside within a siRNA. Exemplary modifications include, e.g., end modifications, e.g., 5'-end modifications (e.g., phosphorylation, conjugation, inverted linkages, etc.) or 3'-end modifications (e.g., conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages.

Embodiments of siRNAs having modified backbones may include those that retain a phosphorus atom in the backbone and those do not. Exemplary modifications on the phosphate backbones of the siRNA include, e.g., phosphorothioates, phosphorodithioates, phosphotriesters, aminoalkylphosphotriesters, alkyl phosphonates, and those having inverted polarity wherein the adjacent pairs of nucleotides are linked 3'-5' to 5'-3' or 2'-5' to 5'-2'. In some embodiments, the sugar backbone of the siRNA may be replaced by, e.g., amide, morpholine, cyclobutyl, etc. In certain embodiments, at least one strand of the siRNA may comprise a phosphorothioate modified phosphate backbone. The phosphorothioate may comprise a P—S bond replacing a P—OH bond in the phosphate backbone.

In various embodiments, any of the modified siRNAs described herein may also comprise one or more modified sugar moieties. The modified sugar moiety may be a ribose or a deoxyribose. For example, the siRNA may comprise at least one modified nucleotide chosen from: e.g., a 2'-deoxy-2'-fluoro modified nucleotide, 2-O-methyl modified nucleotide, 2'-deoxy-modified nucleotide, 2-O-(2-methoxyethyl) nucleotide (2'-MOE-nucleotide), 2'-amino-modified nucleotide, 2'-alkyl-modified nucleotide, and 2-SH-modified nucleotide. Exemplary modified sugar moieties also include, e.g., a locked nucleic acid (LNA), an open-loop or unlocked nucleic acid (UNA), and a peptide nucleic acid (PNA). Similar modifications may also be made at other positions on the siRNA, such as, e.g., at the 3' position of the sugar on the 3'-terminal nucleotide, or at the 5' position of the sugar on the 5'-terminal nucleotide. In some embodiments, at least one strand of the siRNA may comprise a 2'-O-methyl modified nucleotide, i.e., a 2'-O-methyl modification on a ribose or a deoxyribose. In some embodiments, at least one strand of the siRNA may comprise a 2'-deoxy-2'-fluoro modified nucleotide, i.e., a 2'-deoxy-2'-fluoro modification on a ribose or a deoxyribose. In some embodiments, at least one strand of the siRNA may comprise an LNA. The LNA may comprise a cyclic structure formed between 2'-O and 4'-C in a ribose or deoxyribose. In some embodiments, at least one strand of the siRNA may comprise an open-loop nucleic acid or UNA. The open-loop nucleic acid or UNA may comprise a breakage between 2'-C and 3'-C of a ribose or deoxyribose. In some embodiments, at least one strand of the siRNA may comprise a PNA. The PNA may comprise an amide containing backbone replacing the sugar backbone of a nucleotide.

In various embodiments, siRNAs described herein may comprise a nucleobase (or base) modification. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as, e.g., 5-methylcytosine (5-me-C), 5-hydroxymethyl cytosine, 5-acetylenyl uracil, 5-ethynyluracil, 5-propynyl uracil, xanthine, hypoxanthine, 2-aminoadenine, 6-methyl and other alkyl derivatives of adenine and guanine, 2-thiouracil, 5-halouracil, 5-propynyl uracil, 6-azo cytosine, 5-uracil (pseudouracil), indole, 8-halo, 8-amino and other 8-modified adenines and guanines. In some embodiments, at least one strand of the siRNA may comprise an indole modification. In some embodiments, at least one strand of the siRNA may comprise a 5-methylcytosine modification. In some embodiments, at least one strand of the siRNA may comprise a 5-ethynyluracil modification.

Exemplary modifications of the siRNAs described herein also include linking the siRNA to one or more moieties or conjugates, which may enhance the activity of cellular uptake or targeting, or improve the half-life of the siRNA. Such moieties may include but are not limited to lipid moieties (such as, e.g., cholesteryl derivative, phospholipid, aliphatic chain), peptides, nanoparticle, markers (such as, e.g. cyanine fluorescent dye (e.g., Cy3 or Cy5)), polymers (such as, e.g., polyamine or polyethylene glycol chain), sugars (such as, e.g., galactosyl derivative), antibodies, biotin, cholic acid, ligand, thiol, vitamin (such as, e.g., vitamin E), phosphate, and folate. The conjugates may be linked to the siRNA at the 5'-end, 3'-end, or both ends, or internally. In some embodiments, at least one strand of the siRNA may comprise a terminal nucleotide linked to a cholesteryl derivative. In some embodiments, the cholesteryl derivative is cholesterol. In some embodiments, at least one strand of the siRNA may comprise a terminal nucleotide linked to a galactosyl derivative. In some embodiments, the galactosyl derivative is galactose. In some embodiments, at least one strand of the siRNA may comprise a terminal nucleotide linked to a peptide. In some embodiments, the peptide comprises the amino acid sequence N'-Arg-Gly-Asp-C', i.e., an RGD peptide. In some embodiments, at least one strand of the siRNA may comprise a terminal nucleotide linked to a fluorescent marker. In some embodiments, the fluorescent marker is cyanine marker. In some embodiments, at least one strand of the siRNA may comprise a terminal nucleotide linked to a biotin molecule. In some embodiments, at least one strand of the siRNA may comprise a phosphorylated terminal nucleotide.

Various embodiments of the siRNA may comprise any combination of one or more modifications disclosed herein or known in the art. In some embodiments, at least one strand of the siRNA may comprise at least one chemical modification chosen from: (a) a phosphorothioate modified phosphate backbone; (b) a 2'-O-methyl modification in a ribose or deoxyribose; (c) a 2'-deoxy-2'-fluoro modification in a ribose or deoxyribose; (d) an LNA; (e) an open-loop nucleic acid or (UNA); (f) an indole modification; (g) a 5-methylcytosine; (h) a 5'-ethynyluracil; (i) a terminal nucleotide linked to a cholesteryl derivative (such as, e.g., cholesterol); (j) a terminal nucleotide linked to a galactosyl derivative (such as, e.g., galactose); (k) a terminal nucleotide linked to a peptide (such as, e.g., an RGD peptide); (l) a phosphorylated terminal nucleotide (such as, e.g., 5'-phosphorylation); (m) a terminal nucleotide linked to a fluorescent marker (such as, e.g., a cyanine marker); and (n) a terminal nucleotide linked to a biotin molecule. For example, at least one strand of the siRNA may comprise a combination of one or more modifications chosen from those disclosed in Tables 7 and 13.

In some embodiments, the siRNA described herein may comprise a chemically-modified antisense strand chosen from Table 7. In some embodiments, the siRNA may further comprise a chemically-modified sense strand chosen from Table 7. In some embodiments, the siRNA may comprise a chemically-modified antisense strand chosen from Table 13. In some embodiments, the siRNA may further comprise a chemically-modified sense strand chosen from Table 13.

In some embodiments, the sense strand may comprise the nucleotide sequence 5'-K-LLMUUUAUGUGGGCAUP-MQdTdT-3' (SEQ ID NO: 13), and the antisense strand may comprise the nucleotide sequence 5'-R-MQLAUGCCCA-CAUAAAQPPdTdT-3' (SEQ ID NO: 14), wherein K is an optional cholesterol group linked to a 5'-end nucleotide;

R is an optional phosphorylation modification on a 5'-end nucleotide;

dT is a thymine deoxyribonucleotide;

L is an unmodified or 2'-O-methyl modified guanine deoxyribonucleotide;

M is an unmodified or 2'-O-methyl modified adenine deoxyribonucleotides;

P is an unmodified or 2'-O-methyl modified cytosine deoxyribonucleotide;

Q is an unmodified or 2'-O-methyl modified uracil ribonucleotide; and optionally, at least one of L, M, P, and Q has a phosphorothioate backbone.

In some embodiments, at least one of L, M, P, and Q may have a phosphorothioate backbone. In some embodiments, all of L, M, P, and Q may have a phosphorothioate backbone. In some embodiments, the sense strand may comprise a sense sequence chosen from Table 7, and the antisense strand may comprise an antisense sequence chosen from Table 7.

In some embodiments, the sense strand may comprise the nucleotide sequence 5'-K'-L'P'M'UCAU-GUAUCUGAAP'M'M'dTdT-3' (SEQ ID NO: 15), and the antisense strand may comprise the nucleotide sequence 5'-R'-Q'Q'L'UUCAGAUACAUGAQ'L'P' dTdT-3' (SEQ ID NO: 16), wherein K' is an optional cholesterol group linked to a 5'-end nucleotide;

R' is an optional phosphorylation modification on a 5'-end nucleotide;

dT is a thymine deoxyribonucleotide;

L' is an unmodified or 2'-O-methyl modified guanine deoxyribonucleotide;

M' is an unmodified or 2'-O-methyl modified adenine deoxyribonucleotides;

P' is an unmodified or 2'-O-methyl modified cytosine deoxyribonucleotide;

Q' is an unmodified or 2'-O-methyl modified uracil ribonucleotide; and optionally, at least one of L', M', P', and Q' has a phosphorothioate backbone.

In some embodiments, at least one of L', M', P', and Q' may have a phosphorothioate backbone. In some embodiments, all of L', M', P', and Q' may have a phosphorothioate backbone. In some embodiments, the sense strand may comprise a sense sequence chosen from Table 13, and the antisense strand may comprise an antisense sequence chosen from Table 13.

IV. siRNA-Encoding Nucleic Acids

Additional aspects of the disclosure include nucleic acids encoding the siRNAs described herein. For example, the nucleic acid may encode any siRNA comprising a nucleotide sequence having at least 60% (such as, e.g., 65%, 70%, 75%, 80%, 85%, 90%, 95%, 96%, 97%, 98%, or 99%) identity or 100% identity to any one of the nucleotide sequences disclosed herein, such as, e.g., the nucleotide sequences of SEQ ID NOs: 1-4 and 7-10 and those disclosed in Tables 1-3 (SEQ ID NOs: 17-49) and 8-10 (SEQ ID NOs: 98-128). In some embodiments, the nucleic acid may encode an siRNA comprising an antisense sequence having at least 60% (such as, e.g., 65%, 70%, 75%, 80%, 85%, 90%, 95%, 96%, 97%, 98%, or 99%) identity to SEQ ID NO: 2. In some embodiments, the nucleic acid may encode an siRNA comprising the nucleotide sequence of SEQ ID NO: 2. In some embodiments, the nucleic acid may comprise a nucleotide sequence having nucleotides 36-54 of SEQ ID NO: 6. In some embodiments, the nucleic acid may comprise the nucleotide sequence of SEQ ID NO: 6. In some embodiments, the nucleic acid may encode an siRNA comprising a sense sequence having at least 60% (such as, e.g., 65%, 70%, 75%, 80%, 85%, 90%, 95%, 96%, 97%, 98%, or 99%) identity to SEQ ID NO: 1. In some embodiments, the nucleic acid may encode an siRNA comprising the nucleotide sequence of SEQ ID NO: 1. In some embodiments, the nucleic acid may comprise a nucleotide sequence having nucleotides 10-28 of SEQ ID NO: 5. In some embodiments, the nucleic acid may comprise the nucleotide sequence of SEQ ID NO: 5.

In additional embodiments, the nucleic acid may encode an siRNA comprising an antisense sequence having at least 60% (such as, e.g., 65%, 70%, 75%, 80%, 85%, 90%, 95%, 96%, 97%, 98%, or 99%) identity to SEQ ID NO: 8. In some embodiments, the nucleic acid may encode an siRNA comprising the nucleotide sequence of SEQ ID NO: 8. In some embodiments, the nucleic acid may comprise a nucleotide sequence having nucleotides 38-56 of SEQ ID NO: 11. In some embodiments, the nucleic acid may comprise the nucleotide sequence of SEQ ID NO: 11. In some embodiments, the nucleic acid may encode an siRNA comprising a sense sequence having at least 60% (such as, e.g., 65%, 70%, 75%, 80%, 85%, 90%, 95%, 96%, 97%, 98%, or 99%) identity to SEQ ID NO: 7. In some embodiments, the nucleic acid may encode an siRNA comprising the nucleotide sequence of SEQ ID NO: 7. In some embodiments, the nucleic acid may comprise a nucleotide sequence having nucleotides 8-26 of SEQ ID NO: 12. In some embodiments, the nucleic acid may comprise the nucleotide sequence of SEQ ID NO: 12.

In some embodiments, nucleic acid may be a vector. As used herein, a "vector" allows or facilitates the transfer of an entity from one environment to another. It can be a replicon, such as a plasmid, phage, or cosmid, into which another nucleic acid segment may be inserted to bring about the replication of the inserted segment. In some embodiments, a vector may be capable of replication when associated with the proper control elements. In general, the term "vector" refers to a nucleic acid molecule capable of transporting another nucleic acid to which it has been linked. Exemplary vectors include nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double-stranded DNA loop into which additional DNA segments can be inserted, such as by standard molecular cloning techniques. Another type of vector is a viral vector, wherein virally-derived DNA or RNA sequences are present in the vector for packaging into a virus, such as e.g., retroviruses, replication defective retroviruses, adenoviruses, replication defective adenoviruses, and adeno-associated viruses. Viral vectors also include polynucleotides carried by a virus for transfection into a host cell. Certain vectors are capable of autonomous replication in a host cell into which they are introduced (such as, e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise an siRNA-encoding nucleic acid disclosed herein in a form suitable for expression of the nucleic acid in a host cell. For example, the recombinant expression vector may include one or more regulatory elements, which may be selected on the basis of the host cells to be used for expression, that are operatively-linked to the nucleic acid sequence to be expressed. Within a recombinant expression vector, "operably linked" means that the nucleotide sequence of interest is linked to the regulatory element(s) in a manner that allows for expression of the nucleotide sequence, such as, e.g. in an in vitro transcription/translation system or in a host cell when the vector is introduced into the host cell.

In some embodiments, the vector may be a linear construct, a circular plasmid, or a viral vector, which can be an integrating or non-integrating vector. In some embodiments, the individual strand or strands of an siRNA may be transcribed from a promoter on an expression vector. Where two separate strands are to be expressed to generate, for example, a double-stranded siRNA, two separate expression vectors may be co-introduced (e.g., by transfection or infection) into a target cell. Alternatively, each individual strand of a double-stranded siRNA may be transcribed by promoters both of which are located on the same expression vector. In some embodiments, a double-stranded siRNA may be expressed as inverted repeat polynucleotides joined by a linker polynucleotide sequence such that the double-stranded siRNA has a stem and loop structure.

In some embodiments, the siRNA expression vectors may be DNA plasmids or viral vectors. In some embodiments, vectors useful for the delivery of an siRNA may include regulatory elements (promoter, enhancer, etc.) sufficient for expression of the siRNA in the target cell or tissue. The regulatory elements may be chosen to provide either constitutive or regulated/inducible expression. Expression of the siRNA may be regulated, for example, by using an inducible regulatory sequence that is sensitive to certain physiological regulators, such as, e.g., circulating glucose levels, or hormones. Such inducible expression systems, suitable for the control of siRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the siRNA transgene.

Expression vectors compatible with eukaryotic cells, such as, e.g., those compatible with mammalian cells, may be used to produce recombinant constructs for the expression of an siRNA described herein. Eukaryotic cell expression vectors are well known in the art and are available from a number of commercial sources. For example, such vectors may be provided containing convenient restriction sites for insertion of the desired nucleic acid segment. In some embodiments, siRNA expression vector may comprise plasmid pGCsi-H1/Neo having a substituted nucleotide sequence between the restriction sites BamHI and HindIII. In some embodiments, the substituted nucleotide sequence may encode any of the siRNA described herein.

Delivery of siRNA expressing vectors can be systemic, such as, e.g., by intravenous, intramuscular, or joint or intra-articular administration, by administration to target cells ex-planted from a subject followed by reintroduction into the subject, or by any other means that allows for introduction into a desired target cell, e.g., a target cell in a subject. In some embodiments, siRNA expression vectors may be transfected into target cells as a complex with certain delivery carriers, such as, e.g., cationic lipid carriers (e.g., Oligofectamine) or non-cationic lipid-based carriers (e.g., Transit-TKO™). Multiple lipid transfections for siRNA-mediated knockdowns targeting different regions of a target RNA over a period of a week or more are also contemplated in the disclosure. Successful introduction of vectors into host cells may be monitored using various known methods. For example, transient transfection may be signaled with a reporter, such as a fluorescent marker, such as Green Fluorescent Protein (GFP). Stable transfection of cells ex vivo may be ensured using markers that provide the transfected cell with resistance to specific environmental factors (e.g., antibiotics and drugs), such as hygromycin B resistance.

Viral vector systems which may be utilized with the methods and compositions described herein include (a) adenovirus vectors; (b) retrovirus vectors, e.g., lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses may also be advantageous. Different vectors will or will not become incorporated into the genome of the target cell. The constructs may include viral sequences for transfection, if desired. Alternatively, the construct may be incorporated into vectors capable of episomal replication, e.g. EPV and EBV vectors. Constructs for the recombinant expression of an siRNA may further comprise regulatory elements, e.g., promoters, enhancers, etc., to ensure the expression of the siRNA in target cells.

Host cells comprising the siRNA-encoding nucleic acids are also contemplated in the disclosure. In some embodiments, a host cell may be transiently or non-transiently transfected with one or more nucleic acids, e.g., vectors, described herein. In some embodiments, a cell may be transfected as it naturally occurs in a subject. In some embodiments, a cell that is transfected may be taken from a subject. In some embodiments, the cell may be derived from cells taken from a subject, such as a cell line. A wide variety of cell lines for tissue culture are known in the art. Examples of cell lines include C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, 11856, T1B55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr−/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC)). In some embodiments, a cell transfected with one or more vectors described herein may be used to establish a new cell line which may comprise one or more vector-derived sequences.

V. Pharmaceutical Compositions

The present disclosure also includes pharmaceutical compositions comprising any one or more of the siRNAs described herein. In some embodiments, the pharmaceutical compositions may comprise an siRNA, and optionally a pharmaceutically acceptable carrier, diluent, or excipient. In some embodiments, the siRNA may inhibit the expression of ADAMTS-5. In other embodiments, the siRNA may inhibit the expression of ADAM17. In certain embodiments, the pharmaceutical composition may comprise one or more siRNA targeted against a first nucleic acid and one or more additional siRNA targeted against a second nucleic acid target. For example, the pharmaceutical composition may comprise an siRNA inhibiting the expression of ADAMTS-5 and an siRNA inhibiting the expression of ADAM17. In some embodiments, the pharmaceutical composition may comprise an siRNA inhibiting the expression of ADAMTS-5 or ADAM17, and an siRNA targeted against another gene. In other embodiments, the pharmaceutical composition may comprise two or more siRNAs targeted against different regions of the same nucleic acid target. For example, the pharmaceutical composition may comprise two or more siRNAs targeted against different regions of an ADAMTS-5 mRNA. In some embodiments, the pharmaceutical composition may comprise two or more siRNAs targeted against different regions of an ADAM17 mRNA. When two or more different siRNAs are used in combination, the siRNAs may be present, for example, in an equimolar ratio. Two or more combined siRNAs may be used together or sequentially.

The pharmaceutical compositions described herein may be useful for preventing or treating a disease or pathological processes associated with the expression or activity of ADAMTS-5 and/or ADAM17, such as. e.g., inflammation-related diseases, such as, e.g., arthritis, including osteoarthritis, rheumatoid arthritis, chronic infectious arthritis, spondylitis, psoriatic arthritis, and gout. In some embodiments, the disease may be arthritis. In some embodiments, the disease may be osteoarthritis. In some embodiments, the disease may be rheumatoid arthritis. The pharmaceutical compositions may be used for preventing or treating conditions or symptoms of ADAMTS-5- or ADAM17-associated diseases including, e.g., articular fibrosis, cartilage erosion, loss of cartilage collagen, damage of articular cartilage surfaces, synovitis, inflammation in joint capsules, join pain, thickening of joint ligaments, meniscus ossification, and disorganization of cartilage cells. The pharmaceutical compositions may also be used in treating a subject having arthritis associated with TNF-α or COX-2 or IL-1β. Exemplary uses of the pharmaceutical compositions also include, e.g., inhibiting degradation of extracellular matrix; regulating inflammatory cytokines expression, immune cells migration, and inflammatory signal transduction; and protecting cartilage, synovial, joints, and bones. The pharmaceutical compositions may also be used for the treatment or relief of pain, e.g. bone pain or joint pain. Various embodiments also include the use of the pharmaceutical compositions for preventing or treating the diseases, conditions, or symptoms described herein.

"Pharmaceutically acceptable carrier, diluent or excipient" refers to any of the standard pharmaceutical carriers, diluents, buffers, and excipients, such as, e.g., a phosphate buffered saline (PBS) solution, 5% aqueous solution of dextrose, and emulsions, such as an oil/water or water/oil emulsion, and various types of wetting agents and/or adjuvants. Suitable pharmaceutical carriers, diluents or excipients and formulations are known in the art. Proper pharmaceutical carriers, diluents, or excipients may be selected depending upon the intended mode of administration of the active agent.

The pharmaceutical compositions may be administered by methods known in the art or disclosed herein. For example, the pharmaceutical compositions may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer, intratracheal, intranasal), epidermal, and transdermal, spinal, oral, or parenteral. Parenteral administration includes intravenous, intraarterial, subcutaneous, intraperitoneal, or intramuscular injection or infusion; subdermal, e.g., via an implanted device; intracranial, e.g., intrathecal or intraventricular, administration; or joint or intra-articular injection. In some embodiments, the siRNA may be delivered in a manner to target a particular tissue, such as a joint (e.g., an articular cavity). For example, the pharmaceutical composition may be administered by joint or intra-articular injection. In some embodiments, the pharmaceutical composition may be injected into an articular cavity of the subject to be treated.

The pharmaceutical composition may be delivered to cells by a variety of delivery carriers, such as, e.g., liposomes, polymeric compounds, polypeptides, nanomaterials, chitosan, hyaluronic acid and the like. In some embodiments, the pharmaceutical composition may be delivered to cells by a carrier chosen from a cationic liposome, chitosan nanoparticle, peptide, and polymer.

In contrast to a delivery carrier compound, a "pharmaceutical acceptable carrier" or "excipient" refers to a pharmaceutically acceptable solvent, suspending agent, or any other pharmacologically inert vehicle for delivering one or more nucleic acids to a subject. The excipient can be liquid or solid and can be selected, according to the planned manner of administration, to provide for the desired bulk, consistency, etc., when combined with a nucleic acid and the other components of a given pharmaceutical composition. Exemplary pharmaceutical carriers include, e.g., binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.). Suitable pharmaceutically acceptable carriers include, e.g., water, salt solutions, alcohols, polyethylene glycols, gelatin, lactose, amylose, magnesium stearate, talc, silicic acid, viscous paraffin, hydroxymethylcellulose, polyvinylpyrrolidone and the like.

The pharmaceutical compositions may be formulated into any of many possible dosage forms, such as, e.g., tablets, capsules, gel capsules, powders, or granules. The pharmaceutical compositions may also be formulated as solutions, suspensions, emulsions, or mixed media.

In some embodiments, the pharmaceutical compositions may be formulated as a solution. For example, the siRNA may be administered in an unbuffered solution, such as, e.g., in saline or in water. In some embodiments, the siRNA may also be administered in a suitable buffer solution. For example, the buffer solution may comprise acetate, citrate, prolamine, carbonate, or phosphate, or any combination thereof. In some embodiments, the buffer solution may be phosphate buffered saline (PBS). The pH and osmolality of the buffer solution containing the siRNA can be adjusted to be suitable for administering to a subject.

In some embodiments, the pharmaceutical compositions may also be formulated as suspensions in aqueous, non-aqueous, or mixed media. Aqueous suspensions may further contain substances which increase the viscosity of the suspension including, for example, sodium carboxymethylcellulose, sorbitol and/or dextran. The suspension may also contain stabilizers.

In some embodiments, the pharmaceutical compositions may also be formulated as emulsions. Exemplary emulsions include heterogeneous systems of one liquid dispersed in another in the form of droplets usually exceeding 0.1 μm in diameter. Emulsions may contain additional components in addition to the dispersed phases, and the active drug which may be present as a solution in either the aqueous phase, the oily phase, or itself as a separate phase. Microemulsions are also included as an embodiment of the present disclosure.

In some embodiments, the pharmaceutical compositions may also be formulated as liposomal formulations. As used herein, the term "liposome" refers to a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged nucleic acid molecules, e.g., DNA molecules, to form a stable complex. Liposomes that are pH-sensitive or negatively-charged are believed to entrap DNA rather than complex with it. Both cationic and non-cationic liposomes can be used to deliver the nucleic acid molecules described herein to cells.

Liposomes also include "sterically stabilized" liposomes, which may one or more specialized lipids that, when incorporated into liposomes, result in enhanced circulation lifetimes relative to liposomes lacking such specialized lipids. Examples of sterically stabilized liposomes include those in which part of the vesicle-forming lipid portion of the liposome comprises one or more glycolipids or is derivatized with one or more hydrophilic oligomers, such as a polyethylene glycol (PEG) moiety.

The pharmaceutical compositions described herein may also include surfactants. In some embodiments, the pharmaceutical compositions may also employ various penetration enhancers to effect the efficient delivery of nucleic acids. In addition to aiding the diffusion of non-lipophilic drugs across cell membranes, penetration enhancers may also enhance the permeability of lipophilic drugs. Exemplary penetration enhancers include surfactants, fatty acids, bile salts, chelating agents, and non-chelating non-surfactants.

VI. Methods of Use

Certain aspects of the disclosure provide a method of modulating, e.g., inhibiting, the expression of ADAMTS-5 or ADAM17 in vitro, such as e.g., in a solution or a cell-free system (e.g., a cell lysate or in a reconstituted system), or in a cell, such as, e.g., ex vivo in a cell in culture (e.g., a cell expressing ADAMTS-5 or ADAM17), or in vivo in a cell within a subject. In some embodiments, the method may comprise contacting a cell with an siRNA, a nucleic acid encoding the siRNA, or a pharmaceutical composition comprising the siRNA, in an effective amount to inhibit the expression of ADAMTS-5 or ADAM17 in the cell. Additional aspects of the disclosure also provide a method of modulating, e.g., inhibiting, the expression of an inflammatory cytokine in vitro, such as e.g., in a solution or a cell-free system (e.g., a cell lysate or in a reconstituted system), or in a cell, such as, e.g., ex vivo in a cell in culture (e.g., a cell expressing ADAMTS-5 or ADAM17), or in vivo in a cell within a subject. In some embodiments, the method may comprise contacting a cell with an siRNA, a nucleic acid encoding the siRNA, or a pharmaceutical composition comprising the siRNA, in an effective amount to inhibit the expression of the inflammatory cytokine in the cell. In some embodiments, the inflammatory cytokine may be chosen from TNF, COX-2, and IL-1β.

In some embodiments, the cell may be a mammalian cell (such as, e.g., a rat cell, a mouse cell, or a human cell), a synoviocytes, or a recombinant cell. In some embodiments the cell may be a human cell. The subject may be a mammal, such as, e.g., a rat, mouse, or human. In some embodiments, the subject may be a human. In some embodiments, the subject may suffer from an ADAMTS-5- or ADAM17-associated disease, such as, e.g., an inflammation-related disease, or have a risk of developing such disease. Exemplary inflammation-related diseases include, e.g., arthritis, including osteoarthritis, rheumatoid arthritis, chronic infectious arthritis, spondylitis, psoriatic arthritis, and gout. In some embodiments, the disease may be arthritis. In some embodiments, the disease may be osteoarthritis. In some embodiments, the disease may be rheumatoid arthritis.

Additional aspects of this disclosure provide a method for modulating, e.g., inhibiting, the expression of the ADAMTS-5 and/or ADAM17 gene in a subject. In some embodiments, the method may comprise administering a therapeutically effective amount of an siRNA, a nucleic acid encoding the siRNA, or a pharmaceutical composition comprising the siRNA, to a subject such that the expression of the target ADAMTS-5 and/or ADAM17 gene is inhibited. In some embodiments, the method may comprise administering a therapeutically effective amount of a composition containing two or more different siRNA molecules, one targeted against the ADAMTS-5 gene and the other targeted against the ADAM17 gene of the subject to be treated. The subject may be a mammal, such as, e.g., a rat, mouse, or human. In some embodiments, the subject may be a human. In some embodiments, the subject may have an ADAMTS-5- or ADAM17-associated disease, such as, e.g., an inflammation-related disease, or have a risk of developing such disease. Exemplary inflammation-related diseases include, e.g., arthritis, including osteoarthritis, rheumatoid arthritis, chronic infectious arthritis, spondylitis, psoriatic arthritis, and gout. In some embodiments, the disease may be arthritis. In some embodiments, the disease may be osteoarthritis. In some embodiments, the disease may be rheumatoid arthritis.

Additional aspects of this disclosure also provide to the use of at least one siRNA (such as, e.g., ADAMTS-5-siRNA, ADAM17-siRNA, or a combination thereof), a nucleic acid encoding the siRNA, or a pharmaceutical composition comprising the siRNA, e.g., for preventing or treating inflammation-related diseases, such as, e.g., arthritis, including osteoarthritis, rheumatoid arthritis, chronic infectious arthritis, spondylitis, psoriatic arthritis, and gout. In some embodiments, the disease may be arthritis. In some embodiments, the disease may be osteoarthritis. In some embodiments, the disease may be rheumatoid arthritis. The siRNAs or encoding nucleic acids or pharmaceutical compositions may be used for preventing or treating conditions or symptoms of ADAMTS-5- or ADAM17-associated diseases including, e.g., articular fibrosis, cartilage erosion, loss of cartilage collagen, damage of articular cartilage surfaces, synovitis, inflammation in joint capsules, join pain, thickening of joint ligaments, meniscus ossification, and disorganization of cartilage cells. The siRNAs or encoding nucleic acids or pharmaceutical compositions may also be used in treating a subject having arthritis associated with TNF-α or COX-2 or IL-1β. Exemplary uses of the siRNAs or encoding nucleic acids or pharmaceutical compositions also include, e.g., inhibiting degradation of extracellular matrix; regulating inflammatory cytokines expression, immune cells migration, and inflammatory signal transduction; protecting cartilage, synovial, joints, and bones. The siRNAs or encoding nucleic acids or pharmaceutical compositions may also be used for the treatment or relief of pain, e.g. bone pain or joint pain. Various embodiments also include the use of the siRNAs in the preparation of a medicament for preventing or treating the diseases, conditions, or symptoms described herein. In some embodiments, the use or method described herein may comprise administering a therapeutically effective amount of an siRNA, a nucleic acid encoding the siRNA, or a pharmaceutical composition comprising the siRNA to a subject suffering from or having a risk of developing any of these diseases, conditions, or symptoms.

The pharmaceutical compositions may be administered by methods known in the art or disclosed herein. For example, the pharmaceutical compositions may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer, intratracheal, intranasal), epidermal, and transdermal, spinal, oral, or parenteral. Parenteral administration includes intravenous, intraarterial, subcutaneous, intraperitoneal, or intramuscular injection or infusion; subdermal, e.g., via an implanted device; intracranial, e.g., intrathecal or intraventricular, administration; or joint or intra-articular injection. In some embodiments, the siRNA may be delivered in a manner to target a particular tissue, such as a joint (e.g., an articular cavity). For example, the pharmaceutical composition may be administered by joint or intra-articular injection. In some embodiments, the pharmaceutical composition may be injected into an articular cavity of the subject to be treated.

In various embodiments, the siRNA be administered in doses sufficient to inhibit the expression of ADAMTS-5 or ADAM17. For example, a suitable dose of an siRNA may range from about 20 to about 1000 nmol per kilogram (kg) body weight of the recipient per single dose. In some embodiments, the dose may range from about 40 to about 500 nmol per kg body weight per single dose. In some embodiments, the pharmaceutical composition may be administered at a dose of about 40, 50, 100, 150, 200, 250, 300, 350, 400, 450, or 500 nmol per kg body weight per single dose. The pharmaceutical composition may be administered in a single dose or at certain repetition rate. For example, the pharmaceutical composition may be administered once or more times daily, or over longer intervals, such as, e.g., weekly, biweekly, monthly, or yearly. In certain embodiments, the pharmaceutical compositions may be administered twice per week. The pharmaceutical compositions may be administered at regular intervals for a short time period, e.g., daily or weekly for two weeks or less. In some case, the pharmaceutical composition may be administered intermittently over a longer period of time.

In some embodiments, the siRNAs described herein may be used in combination with other pharmaceutically active compounds, including compounds capable of enhancing the effect of the siRNAs described herein, such as, e.g., other siRNAs or anti-inflammatory agents. In some embodiments, the siRNA may be administered simultaneously or sequentially to another drug therapy, such as, e.g., corticosteroids, hyaluronic acid or a salt thereof, non-steroidal anti-inflammatory drugs (NSAIDs, such as, e.g., ibuprofen, paracetamol), disease-modifying anti-rheumatic drugs (DMARDs, such as, e.g., methotrexate), disease modifying osteoarthritic drugs (DMOADs), cartilage protecting agents (such as, e.g., glucosamine, chondroitin sulfate).

In some embodiments, the siRNAs described herein may be used in combination with one or more reagents (such as, e.g., small molecules, monoclonal antibodies, RNAi reagents, etc.) capable of regulating inflammatory cytokines, immune factors, or inflammatory process. Exemplary reagents include, e.g., COX-2 inhibitors (e.g., celecoxib), TNF-α antagonists (e.g., etanercept, adalimumab, infliximab), JAK3 inhibitors, interleukin inhibitors. In some embodiments, the siRNAs described herein may also be used with one or more auxiliary therapeutic agents, such as, e.g., painkillers or analgesics (e.g. dipyrone); or may be used in combination with siRNA targeted against other genes. The pharmaceutical compositions described herein may be combined with other therapies, such as, e.g., surgery (e.g., cartilage transplant, etc.), immunosuppression, radiation treatment, and physical therapy.

VII. Kits

Additional aspects of the disclosure also provide kits for using any of the siRNAs and/or performing any of the methods disclosed herein. In some embodiments, the kits may include one or more siRNA(s) and instructions for use, e.g., instructions for inhibiting expression of ADAMTS-5 or ADAM17 in a cell by contacting the cell with the siRNA(s) in an amount effective to inhibit expression of ADAMTS-5 or ADAM17, or instructions for treating or preventing an ADAMTS-5- or ADAM17-disease in a subject by administering a therapeutically effective amount of the siRNA(s) to the subject. In some embodiments, the instruction may be recorded on a readable carrier. In some embodiments, the instruction may comprise the description of administering the siRNAs, siRNA-encoding nucleic acids, or pharmaceutical compositions described herein into a site where inflammation occurs.

The kits may optionally further comprise means for contacting the cell with the siRNA or administering the siRNA to a subject (e.g., an injection device, such as a device for joint or intra-articular injection), or means for measuring the inhibition of ADAMTS-5 or ADAM17 (e.g., means for measuring the inhibition of ADAMTS-5 or ADAM17 mRNA). Such means for measuring the inhibition of ADAMTS-5 or ADAM17 may comprise a means for obtaining a sample from a subject, such as, e.g., a blood sample or a joint fluid sample. In some embodiments, the joint fluid sample may be from, e.g., hands, feet, wrists, elbows, or ankles. The kits may optionally further comprise means for administering the siRNA(s) to a subject or means for determining the therapeutically effective or prophylactically effective amount.

Unless otherwise defined, all technical and scientific terms used herein have the same meaning as commonly understood by one of ordinary skill in the art to which this invention belongs. Although methods and materials similar or equivalent to those described herein can be used in the practice or testing of the siRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

VIII. Examples

Where no specific instruction is given, materials and reagents in the examples can be obtained from commercial sources. The following materials and reagents were used in the examples: osteoarthritis hFLS cells (Guangdong Traditional Chinese Medicine Hospital); 293T cells (ATCC, catalog number CRL-3216); MCF-7 cells (ATCC, catalog number HTB-22); AssayMax™ Human IL-1β ELISA Kit (AssayPro, catalog number EI2200-1); pGCsi-H1/Neo expression vector (Genscript, also published in Ji et al, "Construction and identification of small hairpin RNA gene Smad4/DPC4 plasmids," Medical Study, 2006, 19(11):973-977); Lipofectamine® 2000 Kit (Invitrogen); Male Sprague Dawley® (SD) rats (220±20 g, Guangdong Medical Experimental Animal Center).

Unless specifically identified, double-stranded siRNAs were used in the examples, and phosphate-buffered saline (PBS) was used as the solution for injection. Unless specifically identified, all hFLS cells mentioned in the examples refer to osteoarthritis hFLS cells.

Example 1

Screening of siRNAs for Inhibiting ADAMTS-5 Expression siRNA Design siRNAs targeted against ADAMTS-5 were designed using bioinformatic techniques, for example, BLAST® alignment. The design process used the ADAMTS-5 mRNA sequence in human (Accession No. NM_007038.3, SEQ ID NO: 191), rat (Accession No. NM_198761.1, SEQ ID NO:

192), or mouse (Accession No. NM_011782, SEQ ID NO: 193). To ensure the specificity of each chosen siRNA targeted against ADAMTS-5, which means the chosen sequence only targets the intended gene but not any other gene, sequence homology analysis was carried out using BLAST®. Only the sequences with maximal sequence divergence from the list of genes with partial sequence identity to the intended mRNA target were chosen. Eight siRNAs capable of inhibiting ADAMTS-5 expression were identified, siRNA-RB-01, siRNA-RB-02, siRNA-RB-03, siRNA-RB-04, siRNA-RB-05, siRNA-RB-06, siRNA-RB-07 and siRNA-RB-08. All eight sequences could target human, rat, and mouse ADAMTS-5.

siRNA Synthesis

5'-O-(4,4'-dimethoxytrityl)-2'-O-t-butyldimethylsilyl-3'-O-(2-cyanoethyl-N,N-diisopropyl) RNA, 2'-deoxy-DNA phosphoramidite, 2'-O-methyl phosphoramidite, the monomers of 6-N-benzoyladenosine (A-Bz), 4-N-acetylcytidine (C-Ac), 2-N-isobutyrylguanosine (G-iBu), and uridine (U) were purchased from Proligo. 2'-deoxy-2'-fluoro phosphoramidite, 5-methyl-2'-deoxyCytidine, Cy5 fluorescence modified phosphoramidites were purchased from Thermo Fisher. 2'-O-TBDMS-inosine, cholesterol phosphoramidites, benzodithiole-3-one-1,1-dioxide (Beaucage reagent), Thiol-Modifier C6 S—S and CPG solid support were purchased from Chemgenes. Peptide cyclo[Arg-Gly-Asp-D-Phe-Lys (PEG-MAL)] (cRGD) was purchased from Peptides International Inc. Locked nucleic acid, unlocked nucleic acid, and galactose modified phosphoramidites were provided by Guangzhou Institutes of Biomedicine and Health, Chinese Academy of Sciences. The other solvents and reagents were purchased from Aladdin Reagents.

All syntheses were conducted on an AM 394 DNA synthesizer using standard protocols with an extended 2-10 min coupling step. A 10-40 fold excess of phosphoramidites and a 150-300 fold excess of 5-(Ethylthio)-1H-tetrazole were used in each coupling cycle. Synthesis scale was 1 μmol. Average coupling yields monitored by trity were 95-98%. The CPG-bound oligoribonucleotides were transferred from the synthesis column to a 5 ml glass screw top vial. 2-3 ml of ethanolic ammonia was added and heated at 55° C. for 12-16 hr. After cooled to −20° C., the ethanolic ammonia was removed from the CPG beads, and the CPG beads were washed with 50:50 ethanol:water. The combined supernatants containing the oligoribonucleotides were dried. To remove the 2'-O-TBDMS protecting groups, 200 μl to 1 ml of 1 M TBAF/THF was added and incubated at room temperature for 12-24 hr. The solution was then added directly to 2-10 ml of 0.1 M TEAB and loaded onto a desalting column. The amount of oligonucleotides was measured by a UV detector; the mass of oligonucleotides was determined by the Oligo HTCS LC-MS system (Novatia). The cRGD peptide siRNA conjugates were prepared following the protocol reported in Liu, et al., "Tumor-targeted in vivo gene silencing via systemic delivery of cRGD-conjugated siRNA," *Nucleic Acids Res.*, 42(18):11805-17 (2014). The double strands were annealed at 95° C. for 3 min, and slowly cooled to 20° C., affording the desired siRNA for ex vivo use. Further desalting and filtration were performed with standard protocols for in vivo use.

Cell Transfection

The experiment was carried out in ten groups, including no target control group (NTC), negative control group (NC), and eight experimental groups, siRNA-RB-01 to siRNA-RB-08.

The experimental groups: hFLS cells were digested with 0.25% trypsin. Then the cell suspension at a density of $10^4$ cells/ml were seeded in 12-well plates with 500 μl per well. When the hFLS cells were grown to the logarithmic phase (i.e., grown to 80% confluence), siRNA (50 nM for single dose screen) were transfected into the cells with Lipofectamine® 2000 using the protocol provided by the manufacturer.

The NTC group: The following random non-specific siRNA was used, with the remaining steps unchanged from the experimental groups:

```
Sense strand:
                                    (SEQ ID NO: 175)
5'-AGAUCGUUAGUUAGGUUGCdTdT-3'

Antisense strand:
                                    (SEQ ID NO: 176)
5'-GCAACCUAACUAACGAUCUdTdT-3'
```

The NC group: No siRNA was transfected, with the remaining steps unchanged from the experimental groups.

Quantitative Real-Time PCR (qPCR)

24 hr after transfection, cells were collected by centrifugation at 1000 rpm for 5 min to remove the supernatant. RNA was then extracted using TRIzol®. The extracted RNA was reverse transcribed into cDNA. qPCR was performed using the cDNA as a template and the following F and R primers. β-actin was used as the reference gene.

```
F:
                                    (SEQ ID NO: 177)
5'-CTGCTCCCAGAAACAACG-3'

R:
                                    (SEQ ID NO: 178)
5'-ATTCAGTGCCATCGGTCA-3'
```

FIG. 1 illustrates the inhibition of ADAMTS-5 expression by all of the eight siRNAs. As indicated in FIG. 1, siRNA-RB-04 was the most effective in inhibiting the expression of ADAMTS-5 mRNA in hFLS cells, reducing the expression level by 90%.

The sense and antisense sequences of siRNA-RB-04 are:

```
Sense strand of siRNA-RB-04:
                                    (SEQ ID NO: 1)
5'-GGAUUUAUGUGGGCAUCAU-3'

Antisense strand of siRNA-RB-04:
                                    (SEQ ID NO: 2)
5'-AUGAUGCCCACAUAAAUCC-3'
```

Western Blotting

Western blot was performed in the hFLS cells from the siRNA-RB-04, NTC, and NC groups. The cell medium was discarded, and cells were washed with PBS for 2 times. The PBS was then discarded, and an appropriate amount of pre-cooled 2× lysis buffer was added. After the cells were scraped with a cellscraper and subsequently incubated on ice for 30 min, the samples were centrifuged under 4° C. at 12000 g for 15 min. Protein concentration in the supernatant was detected by the Bradford method. After the final concentration of the protein was adjusted to 2 μg/μL, the samples can be stored at −80° C. for future use. 12 μg total protein sample was mixed with an equal volume of 2× loading buffer, incubated in boiling water batch for 10 min, and stored at 4° C. Proteins were separated by gel electrophoresis with 10% SDS-PAGE separation gel and 5% stacking gel. After the electrophoresis, the proteins were transferred to a PVDF membrane at 4° C. with 400 mA currency for 2 hr.

Figure 2:
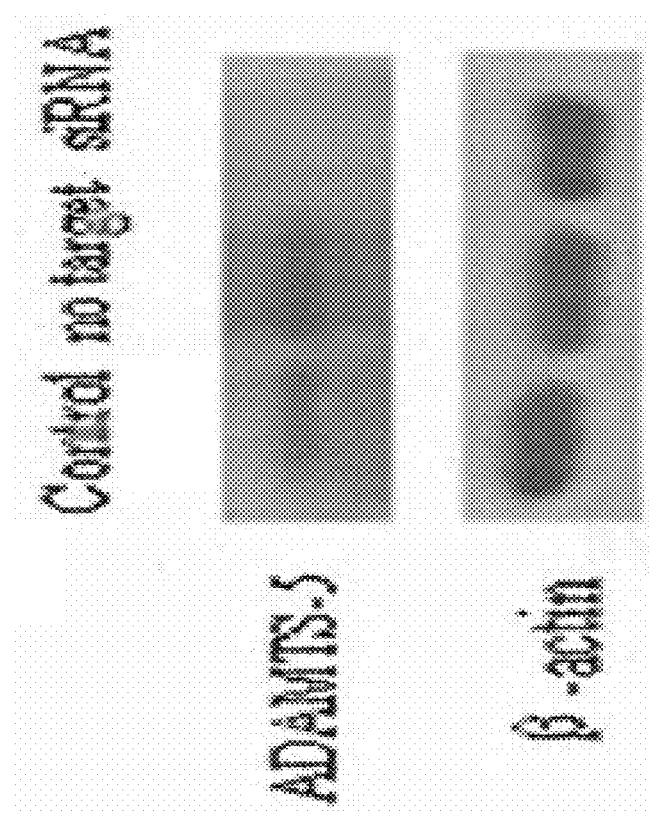
FIG. 2 shows a western blot analysis of siRNA-RB-04.

The results are shown in FIG. 2. "Control" stands for the NC group, "no target" the NTC group, and "siRNA" the siRNA-RB-04 group. FIG. 2 shows that siRNA-RB-04 effectively reduced the expression level of the ADAMTS-5 protein. siRNA-RB-04 was thus taken for subsequent analysis.

$IC_{50}$ Screening $IC_{50}$ (concentration of siRNA resulting in 50% inhibition of ADAMTS-5 mRNA expression compared with untreated control) was determined in hFLS cells transfected with siRNA-RB-04 at the concentrations of 0.01 nM, 0.5 nM, 2.5 nM, 5 nM, 10 nM, 25 nM, 50 nM, and 100 nM. The $IC_{50}$ value was calculated by the Origin 8.0 software. siRNA-RB-04 showed an $IC_{50}$ of 12.6 nM. The expression level of ADAMTS-5 mRNA exhibited a siRNA dose-dependent profile, reduced by 16%, 19%, 36%, 39%, 41%, 63%, 73%, and 74% at above concentrations, respectively.

Example 2

Inhibition of Inflammatory Cytokine Expression by siRNAs

The experiment was carried out in the following groups:

hFLS-siRNA-RB-04 experimental group: Primary hFLS cells were seeded in 6-well plates. When grown to 50% confluence, the cells were transfected with siRNA-RB-04 (50 nM for single dose screen) with Lipofectamine® 2000 using the protocol provided by the manufacturer.

293T-siRNA-RB-04 experimental groups: Primary 293T cells were seeded in 6-well plates. When grown to 50% confluence, the cells were transfected with siRNA-RB-04 (50 nM for single dose screen) with Lipofectamine® 2000 using the protocol provided by the manufacturer.

hFLS-No target control (NTC) group: hFLS cells were transfected with the following random non-specific siRNA, with the remaining steps unchanged from the hFLS-siRNA-RB-04 group.

```
Sense strand:
                              (SEQ ID NO: 175)
5'-AGAUCGUUAGUUAGGUUGCdTdT-3'

Antisense strand:
                              (SEQ ID NO: 176)
5'-GCAACCUAACUAACGAUCUdTdT-3'
```

293T-No target control (NTC) group: 293T cells were transfected with the following random non-specific siRNA, with the remaining steps unchanged from the 293T -siRNA-RB-04 group.

```
Sense strand:
                              (SEQ ID NO: 175)
5'-AGAUCGUUAGUUAGGUUGCdTdT-3'

Antisense strand:
                              (SEQ ID NO: 176)
5'-GCAACCUAACUAACGAUCUdTdT-3'
``` hFLS-Negative control (NC) group: No siRNA was transfected, with the remaining steps unchanged from the hFLS-siRNA-RB-04 group.

293T-Negative control (NC) group: No siRNA was transfected, with the remaining steps unchanged from the 293T-siRNA-RB-04 group.

24 hr after transfection, cells in each group were cultured in a serum-free medium for starvation cultivation for 24 hr. The cells were stimulated by IL-1α with a final concentration of 10 ng/ml for 24 hr. RNA was extracted, and qPCR was performed with the following primers to detect the expression levels of TNF, COX-2 and IL-1β. β-actin was used as the reference gene.

```
TNF-F:
                              (SEQ ID NO: 179)
5'-CGAGTGACAAGCCTGTAGCC-3'

TNF-R:
                              (SEQ ID NO: 180)
5'-TGAAGAGGACCTGGGAGTAGAT-3'

Cox2-F:
                              (SEQ ID NO: 181)
5'-CAGGGTTGCTGGTGGTAGGA-3'

Cox2-R:
                              (SEQ ID NO: 182)
5'-GCATAAAGCGTTTGCGGTAC-3'

IL-1β-F:
                              (SEQ ID NO: 183)
5'-ACGAATCTCCGACCACCA-3'

IL-1β-R:
                              (SEQ ID NO: 184)
5'-GGACCAGACATCACCAAGC-3'
```

Figure 3A:
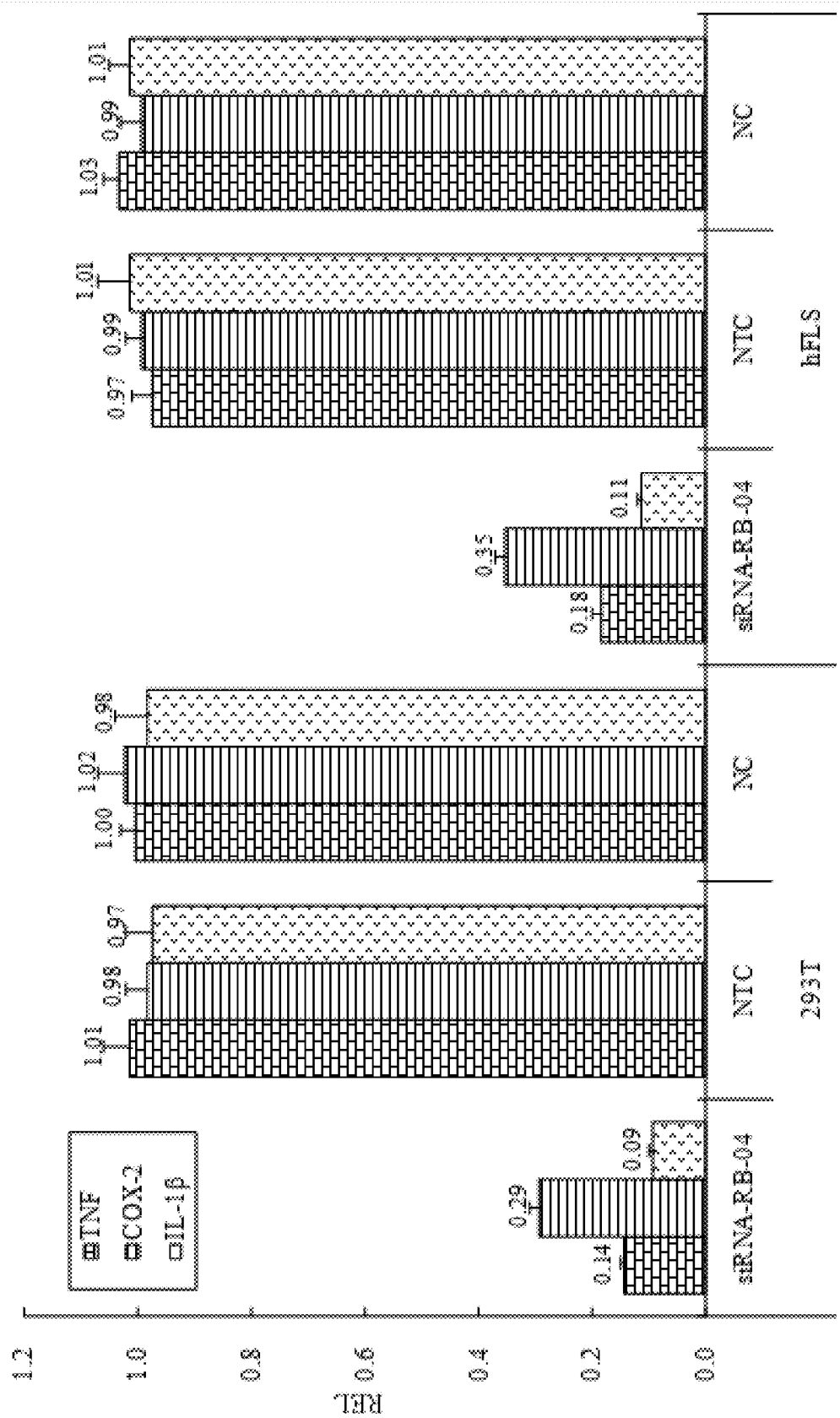
FIG. 3A-3B shows that siRNA-RB-04 down-regulated certain inflammatory cytokines.

FIG. 3A shows that siRNA-RB-04 effectively reduced the mRNA expression of TNF, COX-2, and IL-1β in hFLS and 293T cells. Specifically, the IL-1β expression level in hFLS cells was reduced by 89%.

The cell supernatant was collected to detect the levels of secreted IL-1β by AssayMax™ Human IL-1β ELISA Kit. The cells in the NTC groups were further divided as follows:

hFLS-No target control (NTC+) group: hFLS-NTC group treated with IL-1α.

hFLS-No target control (NTC−) group: hFLS-NTC group not treated with IL-1α.

293T-No target control (NTC+) group: 293T-NTC group treated with IL-1α.

293T-No target control (NTC−) group: 293T-NTC group not treated with IL-1α.

Figure 3B:
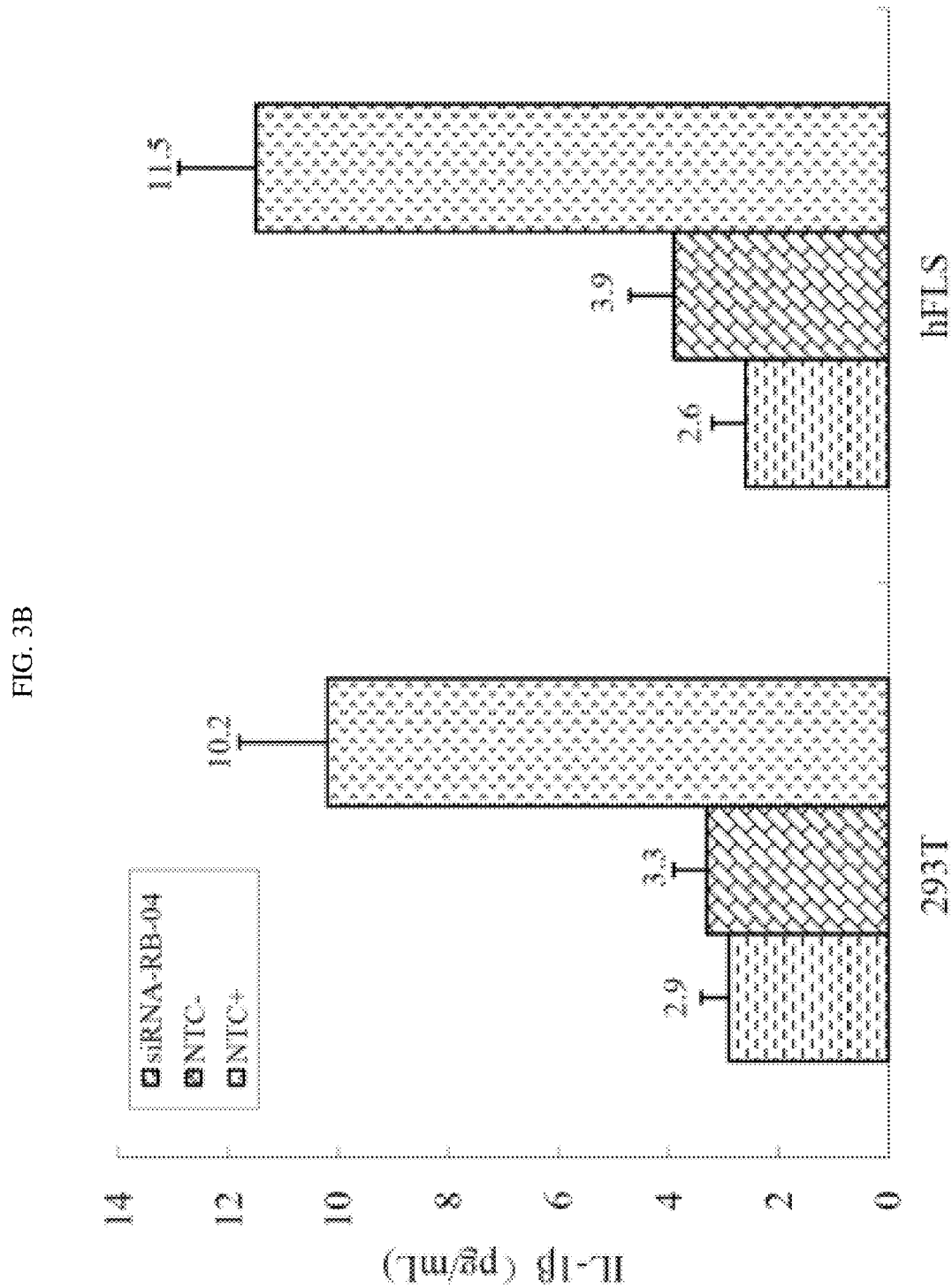

FIG. 3B shows that siRNA-RB-04 inhibited the secretion of the IL-1β protein to a level even lower than that in the unstimulated NTC-groups.

Example 3

Inhibition of ADAMTS-5 by siRNAs with Certain Sequence Identity to siRNA-RB-04

The first set of experiments used siRNAs having the antisense strand of siRNA-RB-04 5'-AUGAUGCCCA-CAUAAAUCC-3' (SEQ ID NO: 2), and a sense strand containing or having certain sequence identity to the sense strand of siRNA-RB-04 5'-GGAUUUAUGUGGGCAU-CAU-3' (SEQ ID NO: 1), as shown in Table 1.

TABLE 1

Antisense Group

| siRNA | S (5'→3') | AS (5'→3') | Identity % | REL |
|---|---|---|---|---|
| RB-09 | AUUUAUGUGGGCAUC (SEQ ID NO: 17) | AUGAUGCCCACAUA AAUCC (SEQ ID NO: 2) | 79 | 0.34 |
| RB-10 | UUAUGUGGGCA (SEQ ID NO: 18) | AUGAUGCCCACAUA AAUCC (SEQ ID NO: 2) | 58 | 0.41 |
| RB-11 | GGAUUUAUGUGGGCAUCAU UCAU (SEQ ID NO: 19) | AUGAUGCCCACAUA AAUCC (SEQ ID NO: 2) | contain | 0.26 |
| RB-12 | GGAUUUAUGUGGGCAUCAU UCAUGUGA (SEQ ID NO: 20) | AUGAUGCCCACAUA AAUCC (SEQ ID NO: 2) | contain | 0.45 |
| RB-14 | CUAG<br>\\ /<br>5'-GGAUUUAUGUGGGCAUCAU-3'<br>(SEQ ID NO: 21) | AUGAUGCCCACAUA AAUCC (SEQ ID NO: 2) | contain | 0.25 |
| RB-42 | G*C*UGUUAUGUGGGCAUCAU (SEQ ID NO: 22) | AUGAUGCCCACAUA AAUCC (SEQ ID NO: 2) | 84 | 0.27 |
| RB-43 | GG*U*UAUAUGUGGGCAUCAU (SEQ ID NO: 23) | AUGAUGCCCACAUA AAUCC (SEQ ID NO: 2) | 89 | 0.26 |
| RB-44 | GGAUUUAUGU*A*GGCAUCAU (SEQ ID NO: 24) | AUGAUGCCCACAUA AAUCC (SEQ ID NO: 2) | 95 | 0.23 |
| RB-45 | G*C*UG*U*AAUGU*A*GGCAUCAU (SEQ ID NO: 25) | AUGAUGCCCACAUA AAUCC (SEQ ID NO: 2) | 74 | 0.32 |
| RB-46 | *AAGUC* *C*UUGUGGGCAUCAU (SEQ ID NO: 26) | AUGAUGCCCACAUA AAUCC (SEQ ID NO: 2) | 68 | 0.37 |
| RB-47 | AUU*A*AUGUGGGCAUC (SEQ ID O: 27) | AUGAUGCCCACAUA AAUCC (SEQ ID NO: 2) | 74 | 0.35 |
| RB-69 | *CAG*UUUAUGUGGGCA (SEQ ID NO: 28) | AUGAUGCCCACAUA AAUCC (SEQ ID NO: 2) | 63 | 0.49 |

Note:
S = sense strand,
AS = antisense strand,
Italics = mismatches,
REL = relative expression level The second set of experiments used siRNAs having the sense strand of siRNA-RB-04 5'-GGAUUUAU-GUGGGCAUCAU-3' (SEQ ID NO: I), and an antisense strand containing or having certain sequence identity to the antisense strand of siRNA-RB-04 5'-AUGAUGCCCA-CAUAAAUCC-3' (SEQ ID NO: 2), as shown in Table 2.

TABLE 2

Sense Group

| siRNA | S (5'→3') | AS (5'→3') | Identity % | REL |
|---|---|---|---|---|
| RB-15 | GGAUUUAUGUGGGC AUCAU (SEQ ID NO: 1) | GAUGCCCACAUAAAU (SEQ ID NO: 29) | 79 | 0.58 |
| RB-16 | GGAUUUAUGUGGGC AUCAU (SEQ ID NO: 1) | UGCCCACAUAA (SEQ ID NO: 30) | 58 | 0.75 |
| RB-17 | GGAUUUAUGUGGGC AUCAU (SEQ ID NO: 1) | AUGAAUGAUGCCCACAUA AAUCC (SEQ ID NO: 31) | contain | 0.43 |
| RB-18 | GGAUUUAUGUGGGC AUCAU (SEQ ID NO: 1) | UCACAUGAAUGAUGCCCAC AUAAAUCC (SEQ ID NO: 32) | contain | 0.47 |
| RB-19 | GGAUUUAUGUGGGC AUCAU (SEQ ID NO: 1) | 5'-AUGAUGCCCACAUAAAUCC-3'<br>/ \\<br>GGUC<br>(SEQ ID NO: 33) | contain | 0.33 |
| RB-48 | GGAUUUAUGUGGGC AUCAU (SEQ ID NO: 1) | AUGAUGCCCACAU*AGA*UUC (SEQ ID NO: 34) | 89 | 0.38 |
| RB-49 | GGAUUUAUGUGGGC AUCAU (SEQ ID NO: 1) | AUGAUGCCCACAUA*CC*AUC (SEQ ID NO: 35) | 79 | 0.36 |
| RB-50 | GGAUUUAUGUGGGC AUCAU (SEQ ID NO: 1) | AUGAUGCCCACAUA*CC*ACC (SEQ ID NO: 36) | 84 | 0.42 |
| RB-51 | GGAUUUAUGUGGGC AUCAU (SEQ ID NO: 1) | AUGAUGCCCACAG*A*CCAUC (SEQ ID NO: 37) | 74 | 0.45 |
| RB-52 | GGAUUUAUGUGGGC AUCAU (SEQ ID NO: 1) | AUGAUGCCCACAUA*C*AUCC (SEQ ID NO: 38) | 95 | 0.29 |

TABLE 2-continued

| | Sense Group | | | |
|---|---|---|---|---|
| siRNA | S (5'→3') | AS (5'→3') | Identity % | REL |
| RB-70 | GGAUUUAUGUGGGC AUCAU (SEQ ID NO: 1) | ACGAUGCCCACAUGCA (SEQ ID NO: 39) | 68 | 0.54 |

Note:
S = sense strand,
AS = antisense strand,
Italics = mismatches,
REL = relative expression level The third set of experiments used siRNAs having a sense strand containing or having certain sequence identity to the sense strand of siRNA-RB-04 5'-GGAUUUAU-GUGGGCAUCAU-3' (SEQ ID NO: 1), and an antisense strand containing or having certain sequence identity to the antisense strand of siRNA-RB-04 5'-AUGAUGCCCA-CAUAAAUCC-3' (SEQ ID NO: 2), as shown in Table 3.

TABLE 3

| | Double Strands Group | | | |
|---|---|---|---|---|
| siRNA | S (5'→3') | AS (5'→3') | Identity % | REL |
| RB-20 | UUAUGUGGGCAdTdT (SEQ ID NO: 40) | UGCCCACAUAAdTdT (SEQ ID NO: 45) | 58 | 0.78 |
| RB-21 | GGAUUUAUGUGGGCAUCAU UCAUGUGAdTdT (SEQ ID NO: 41) | UCACAUGAAUGAUGCCCAC AUAAAUCCdTdT (SEQ ID NO: 46) | contain | 0.53 |
| RB-22 | GGAUUUAUGUGGGCAUCAU UCAU (SEQ ID NO: 19) | GAUGCCCACAUAAAU (SEQ ID NO: 29) | contain/79 | 0.57 |
| RB-23 | AUUUAUGUGGGCAUC (SEQ ID NO: 17) | AUGAAUGAUGCCCACAUAA AUCC (SEQ ID NO: 31) | 79/contain | 0.36 |
| RB-24 | 5'-GGAUUUAUGUGGGCAUCAU-3' with CUAG insertion (SEQ ID NO: 21) | 5'-AUGAUGCCCACAUAAAUCC-3' with GGUC insertion (SEQ ID NO: 33) | contain | 0.46 |
| RB-13 | GGAUUUAUGUGGGCAUCAU dTdT (SEQ ID NO: 3) | AUGAUGCCCACAUAAAUCCd TdT (SEQ ID NO: 4) | contain | 0.09 |
| RB-53 | AUUUAUGUGGGCAUC (SEQ ID NO: 17) | GAUGCCCACAUAAAU (SEQ ID NO: 29) | 79/79 | 0.53 |
| RB-54 | GGUUAUGUGGGCAUCAU (SEQ ID NO: 23) | AUGAUGCCCACAUA*GAUUC* (SEQ ID NO: 34) | 89/89 | 0.42 |
| RB-55 | G*CUG*UUAUGUGGGCAUCAU (SEQ ID NO: 22) | AUGAUGCCCACAUA*C*AUCC (SEQ ID NO: 38) | 85/95 | 0.32 |
| RB-56 | G*CUG*UAAUGUAGGCAUCAU (SEQ ID NO: 25) | AUGAUGCCCACAUA*GAUUC* (SEQ ID NO: 34) | 75/89 | 0.45 |
| RB-57 | GGAUUUAUGU*AG*GCAUCAU (SEQ ID O: 24) | AUGAUGCCCACAUA*C*AUCC (SEQ ID NO: 38) | 95/95 | 0.25 |
| RB-58 | UCGGGAGGAUUUAUGUGGG CAUCAU (SEQ ID NO: 42) | AUGAUGCCCACAUAAAUCC UCCCGA (SEQ ID NO: 47) | contain | 0.47 |
| RB-59 | GGAUUUAUGUGGGCAUCAU AGUACA (SEQ ID NO: 43) | UGUACUAUGAUGCCCACAU AAAUCCAG (SEQ ID NO: 48) | contain | 0.46 |
| RB-60 | GGAUUUAUGUGGGCAUCAU AGUAdCdA (SEQ ID NO: 44) | UGUACUAUGAUGCCCACAU AAAUCCAG (SEQ ID NO: 48) | contain | 0.35 |
| RB-61 | GGAUUUAUGUGGGCAUCAU AGUAdCdA (SEQ ID NO: 44) | UGUACUAUGAUGCCCACAU AAAUCCUU (SEQ ID NO: 49) | contain | 0.39 |
| RB-71 | GG*U*UAUGUGGGCAUCAU (SEQ ID NO: 23) | ACGAUGCCCACAUGCA (SEQ ID NO: 39) | 89/68 | 0.62 |
| RB-72 | *CAG*UUUAUGUGGGCA (SEQ ID NO: 28) | ACGAUGCCCACAUGCA (SEQ ID NO: 39) | 63/68 | 0.71 |

Note:
S = sense strand,
AS = antisense strand,
Italics = mismatches,
REL = relative expression level The siRNAs in Tables 1-3 were each introduced into hFLS cells, and the expression levels of ADAMTS-5 mRNA were detected using the method of Example 1. All of the three sets of experiments used the NTC and NC groups as prepared in Example 1.

As indicated in Tables 1-3, all of the siRNAs in three groups reduced the expression levels of ADAMTS-5 mRNA. The more effective siRNAs included (1) siRNAs having an antisense strand comprising SEQ ID NO: 2, and a sense strand having at least 60% identity to SEQ ID NO: 1; (2) siRNAs having a sense strand comprising SEQ ID NO: 1, and an antisense strand having at least 60% identity to SEQ ID NO: 2; and (3) siRNAs having a sense strand having at least 60% identity to SEQ ID NO: 1, and an antisense strand having at least 60% identity to SEQ ID NO: 2. In particular, 21-nt siRNA-RB-β having 3' overhang nucleotides reduced the expression level of ADAMTS-5 by 91%.

Example 4

Silencing ADAMTS-5 with siRNA-Encoding Plasmids

A DNA oligonucleotide encoding the sequence of siRNA-RB-04 was designed as shown in Table 4.

TABLE 4

DNA Oligonucleotide Encoding siRNA-RB-04

| Sequence number | (5'→3') Sequence of DNA oligonucleotide encoding siRNA-RB-04 |
|---|---|
| SEQ ID NO: 5 | AGCTA<u>AAAAAATGATGCCCACATAAATCCTCTCTTGAAGGA TTTATGTGGGCATCATGGG</u> |
| SEQ ID NO: 6 | GATCCCCATGATGCCCACATAAATCCTTCAAGAGAGGATTT ATGTGGGCATCATTTTTT |

The complementary region of the DNA oligonucleotide is underlined. Nucleotides 10-28 (bold) of SEQ ID NO: 5 encode the sense strand of siRNA-RB-04 (SEQ ID NO: 1). Nucleotides 36-54 (bold) of SEQ ID NO: 6 encode the antisense strand of siRNA-RB-04 (SEQ ID NO: 2).

The DNA strands as shown in Table 4 were annealed and cloned into the region between the BamHI and HindIII restriction sites of siRNA expression vector pGCsi-H1/Neo to obtain a recombinant siRNA expression plasmid, Vector 1.

The experiment was conducted in the following groups:

Experimental group: hFLS cells were seeded in 6-well plates one day before transfection. 50 nM Vector 1 was introduced into the hFLS cells with Lipofectamine® 2000 using the protocol provided by the manufacturer. Cells were collected after transfection for 48 hr, and the expression level of ADAMTS-5 mRNA was detected by the method of Example 1.

No target control (NTC) group: DNA encoding the following random non-specific siRNA was cloned into pGCsi-H1/Neo, with the remaining steps unchanged from the experimental group.

Sense strand:

(SEQ ID NO: 175)
5'-AGAUCGUUAGUUAGGUUGCdTdT-3'

Antisense strand:

(SEQ ID NO: 176)
5'-GCAACCUAACUAACGAUCUdTdT-3'

Negative control (NC) group: The original pGCsi-H1/Neo plasmid without the interference fragment was used, with the remaining steps unchanged from the experimental group. The results are shown in Table 5.

TABLE 5

| Relative Expression Levels of ADAMTS-5 | | |
|---|---|---|
| Experimental group | NC group | NTC group |
| 0.20 ± 0.02 | 1.15 ± 0.18 | 0.97 ± 0.15 |

Table 5 demonstrates that transfection of DNA encoding siRNA-RB-04 also effectively silenced ADAMTS-5.

Example 5

Silencing of ADAMTS-5 by Chemically-Modified siRNAs siRNA-RB-13 and siRNA-RB-04 were subjected to various types or combinations of chemical modifications as shown in Tables 6 and 7 to further increase the stability and interference effect of the siRNA molecules.

TABLE 6

| Chemical Modifications | | | |
|---|---|---|---|
| No | Modification type | Modification location | Illustration |
| 1 | thiophosphoric acid (P—S) | Phosphate backbone | As |
| 2 | 2'-OMe | Ribose or deoxyribose | Am |
| 3 | 2'-F | Ribose or deoxyribose | Af |
| 4 | LNA | Ribose or deoxyribose | <u>A</u> |
| 5 | UNA | Bond breakage between 2'-C and 3'-C in ribose or deoxyribose | An |
| 6 | indole | Base | Ai |
| 7 | 5-methylcytosine | Base | <u>A</u> |
| 8 | 5-ethynyluracil | Base | <u>A</u> |
| 9 | cholesterol | 5'-end or 3'-end | Chol-A or A-Chol |
| 10 | galactose | 3'-end | A-Gal |
| 11 | polypeptide | 5'-end | Pep-A |
| 12 | phosphorylation | 5'-end | p-A |
| 13 | fluorescent marker | 5'-end | Cy-A |
| 14 | biotinylation | 5'-end | Bio-A |

Figure 4:
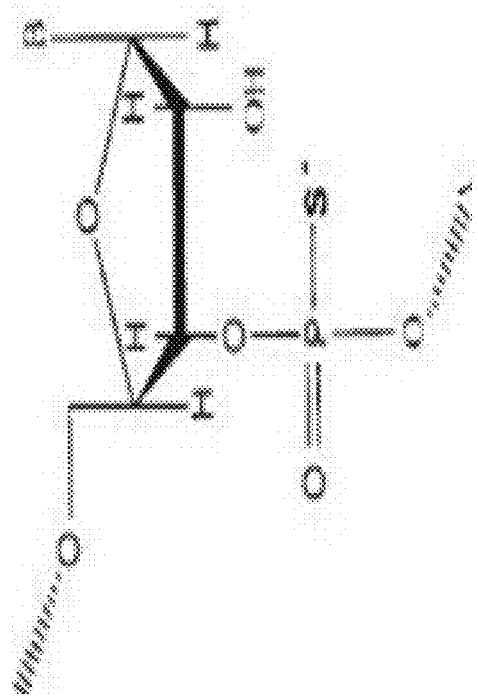
FIG. 4 depicts a phosphorothioate modification resulting in a P—S bond on the phosphate backbone of an siRNA.

The phosphorothioate (P—S bond) modification is illustrated in FIG. 4. The LNA modification formed a cyclic structure between 2'-O and 4'-C in a ribose or deoxyribose. Polypeptide RGD (N'-Arg-Gly-Asp-C', Sigma) was used. "A" represents any nucleotide.

TABLE 7

Silencing of ADAMTS-5 by Chemically-modified siRNAs

| Modification | siRNA | Strand | siRNA sequence (5'→3') | REL |
|---|---|---|---|---|
| none | RB-13 | S | GGAUUUAUGUGGGCAUCAUdTdT (SEQ ID NO: 3) | 0.09 ± 0.01 |
|  |  | AS | AUGAUGCCCACAUAAAUCCdTdT (SEQ ID NO: 4) |  |
| thiophosphoric acid | RB-25 | S | GsGsAsUUUAUGUGGGCAUCsAsUs dTdT (SEQ ID NO: 50) | 0.13 ± 0.02 |
|  |  | AS | AsUsGsAUGCCCACAUAAAUsCsCs dTdT (SEQ ID NO: 51) |  |
| 5-cholesterol | RB-26 | S | Chol-GGAUUUAUGUGGGCAUCAU dTdT (SEQ ID NO: 52) | 0.11 ± 0.02 |
|  |  | AS | AUGAUGCCCACAUAAAUCCdTdT (SEQ ID NO: 53) |  |
| 2'-OMe | RB-27 | S | GmGmAmUUUAUGUGGGCAUCm AmUmdTdT (SEQ ID NO: 54) | 0.08 ± 0.01 |
|  |  | AS | AmUmGmAUGCCCACAUAAAUmCm Cm dTdT (SEQ ID NO: 55) |  |
| 2'-F | RB-28 | S | GfGfAfUUUAUGUGGGCAUCfAfUf dTdT (SEQ ID NO: 56) | 0.16 ± 0.02 |
|  |  | AS | AfUfGfAUGCCCACAUAAAUfCfCf dTdT (SEQ ID NO: 57) |  |
| LNA | RB-29 | S | GGAUUUAUGUGGGCAUCAUdTdT (SEQ ID NO: 58) | 0.11 ± 0.02 |
|  |  | AS | [AUG]AUGCCCACAUAAA[UCC]dTdT (SEQ ID NO: 59) |  |
| UNA | RB-30 | S | GGAUUUAUGUGGGCAUCAUdTdT (SEQ ID NO: 60) | 0.24 ± 0.03 |
|  |  | AS | AnUGAUGCCCACAUAAAUCCdTdT (SEQ ID NO: 61) |  |
| indole | RB-31 | S | GiGiAiUUUAUGUGGGCAUCiAiUi dTdT (SEQ ID NO: 62) | 0.12 ± 0.02 |
|  |  | AS | AiUiGiAUGCCCACAUAAAUiCiCi dTdT (SEQ ID NO: 63) |  |
| 5-methylcytosine | RB-32 | S | GGAUUUAUGUGGG<u>C</u>AUCAUdTdT (SEQ ID NO: 64) | 0.11 ± 0.01 |
|  |  | AS | AUGAUG<u>CCC</u>ACAUAAA<u>CC</u>dTdT (SEQ ID NO: 65) |  |
| 5-ethynyluracil | RB-33 | S | GGA<u>UUU</u>AUGUGGGCA<u>U</u>CA<u>U</u>dTdT (SEQ ID NO: 66) | 0.33 ± 0.02 |
|  |  | AS | A<u>U</u>GA<u>U</u>GCCCACAUAAA<u>U</u>CCdTdT (SEQ ID NO: 67) |  |
| galactose, 2'-OMe | RB-34 | S | GmGmAmUUUAUGUGGGCAUCm AmUmdTdT-Gal (SEQ ID NO: 68) | 0.14 ± 0.01 |
|  |  | AS | AmUmGmAUGCCCACAUAAAUmCm CmdTdT (SEQ ID NO: 69) |  |
| phosphorylation, 2'-OMe | RB-35 | S | GmGmAmUUUAUGUGGGCAUCm AmUmdTdT (SEQ ID NO: 70) | 0.07 ± 0.01 |
|  |  | AS | p-AmUmGmAUGCCCACAUAAAUm CmCmdTdT (SEQ ID NO: 71) |  |
| 2'-OMe, polypeptide | RB-36 | S | Pep-GmGmAmUUUAUGUGGGCAU CmAmUmdTdT (SEQ ID NO: 72) | 0.18 ± 0.02 |
|  |  | AS | AmUmGmAUGCCCACAUAAAUmCm CmdTdT (SEQ ID NO: 73) |  |
| phosphorylation, 2'-OMe, Cy | RB-37 | S | Cy-GmGmAmUUUAUGUGGGCAU CmAmUmdTdT (SEQ ID NO: 74) | 0.16 ± 0.02 |
|  |  | AS | p-AmUmGmAUGCCCACAUAAAUm CmCmdTdT (SEQ ID NO: 75) |  |
| 2'-OMe, thiophosphoric acid | RB-38 | S | GmsGmsAmsUUUAUGUGGGCAU CmsAmsUmsdTdT (SEQ ID NO: 76) | 0.09 ± 0.02 |
|  |  | AS | AmsUmsGmsAUGCCCACAUAAA UmsCmsCmsdTdT (SEQ ID NO: 77) |  |
| 2'-OMe, cholesterol | RB-39 | S | Chol-GmGmAmUUUAUGUGGGCAU CmAmUmdTdT (SEQ ID NO: 78) | 0.10 ± 0.01 |
|  |  | AS | AmUmGmAUGCCCACAUAAAUmCm CmdTdT (SEQ ID NO: 79) |  |
| 2'-OMe, cholesterol, phosphorylation | RB-40 | S | Chol-GmGmAmUUUAUGUGGGCAU CmAmUmdTdT (SEQ ID NO: 80) | 0.07 ± 0.01 |
|  |  | AS | p-AmUmGmAUGCCCACAUAAAUm CmCmdTdT (SEQ ID NO: 81) |  |
| 2'-OMe, thiophosphoric acid, cholesterol, phosphorylation | RB-41 | S | Chol-GmsGmsAmsUUUAUGUGGGCA UCmsAmsUmsdTdT (SEQ ID NO: 82) | 0.07 ± 0.01 |
|  |  | AS | p-AmsUmsGmsAUGCCCACAUAAA UmsCmsCmsdTdT (SEQ ID NO: 83) |  |

TABLE 7-continued

Silencing of ADAMTS-5 by Chemically-modified siRNAs

| Modification | siRNA | Strand | siRNA sequence (5'→3') | REL |
|---|---|---|---|---|
| 5-methylcytosine, 2'-OMe | RB-62 | S | GmGAmUUUAUGUGGGCAUCAU dTdT (SEQ ID NO: 84) | 0.17 ± 0.03 |
| | | AS | AmUmGmAUGCCCACAUAAAUCC dTdT (SEQ ID NO: 85) | |
| 2'-OMe, biotinylation | RB-63 | S | Bio-GmGmAUUUAUGUGGGCAUC AmUmdTdT (SEQ ID NO: 86) | 0.26 ± 0.05 |
| | | AS | AmUmGAUGCCCACAUAAAUCmCm dTdT (SEQ ID NO: 87) | |
| 2'-OMe, 2'-F | RB-64 | S | GfGfAUUUAUGUGGGCAUCAUmUm (SEQ ID NO: 88) | 0.17 ± 0.03 |
| | | AS | AfAfUGAUGCCCACAUAAAUCmCm (SEQ ID NO: 89) | |
| 2'-OMe, 2'-F, thiophosphoric acid | RB-65 | S | GmGfAUUUAUGUGGGCAUCAfUm (SEQ ID NO: 90) | 0.22 ± 0.04 |
| | | AS | AfUmGAUGCCCACAUAAAUCfCm (SEQ ID NO: 91) | |
| 2'-OMe, thiophosphoric acid | RB-66 | S | GGAUUUAUmGUGGGCmAUCmAU dTsdT (SEQ ID NO: 92) | 0.14 ± 0.04 |
| | | AS | AUmGAUmGCCCACAUmAAAUmCC dTsdT (SEQ ID NO: 93) | |
| 2'-OMe, thiophosphoric acid | RB-67 | S | GGAUUUmAUGUGGGCAUmCAsU (SEQ ID NO: 94) | 0.20 ± 0.04 |
| | | AS | AUGAUGCCCACAUmAAAUCmCUs C (SEQ ID NO: 95) | |
| 3'-cholesterol | RB-68 | S | GGAUUUAUGUGGGCAUCAUdTdT- Chol (SEQ ID NO: 96) | 0.18 ± 0.03 |
| | | AS | AUGAUGCCCACAUAAAUCCdTdT (SEQ ID NO: 97) | |

Note:
S = sense strand,
AS = antisense strand,
REL = relative expression level

Chemically-modified siRNA as shown in Table 7 were transfected into hFLS cells, and the expression levels of ADAMTS-5 mRNA were determined by the method of Example 1. Where siRNAs modified with cholesterol, polypeptides, or galactose were used, no transfection reagent was added.

The results in Table 7 show that siRNA-RB-13 and siRNA-RB-04 with appropriate chemical modifications effectively silenced ADAMTS-5.

Example 6

Stabilization of siRNAs in Serum by Chemical Modifications

Serum stability of the chemically-modified siRNAs in example 5 was determined as follows: equal volume fresh rat serum was added into 5 µM siRNAs diluted by RNAase-free water. The mixture was incubated at 37° C. for 30 min and subjected to electrophoresis to check the integrity of the siRNAs.

Figure 5:
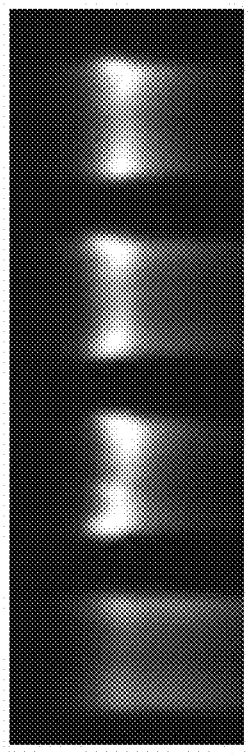
FIG. 5 shows that certain chemical modifications enhanced the stability of certain exemplary siRNAs targeted against ADAMTS-5 in the serum.

As shown in FIG. 5, after 30 min incubation in rat serum, a significantly amount of unmodified siRNA-RB-13 was degraded, while the chemically-modified molecules siRNA-RB-41, siRNA-RB-40, and siRNA-RB-35 exhibited no sign of degradation.

Example 7

Efficacy of siRNAs in Treating Rat Model of Arthritis

A rat model of arthritis was constructed using bovine type H collagen to promote the formation of arthritis, including symptoms of osteoarthritis. Bovine type II collagen (4 mg/mL, Sigma) was injected into the joint cavity of male SD rats (220±20 g) at 100 µL per leg, totally 200 µL per animal.

3 d after the injection of bovine type II collagen, the arthritic rats were randomly divided into four groups with eight rats in each group as follows: PBS group, injected with 100 µL PBS control, and siRNA-RB-40, siRNA-RB-35, and siRNA-RB-41 experimental groups, injected with 10 nmol siRNA solution (1004) at 50 µL per leg. The control or siRNA was administered to each group twice a week for two weeks.

Four rats from each group were sacrificed the day after the fourth administration, and knee joints were fixed in a tissue preservation solution for hematoxylin-eosin (HE) or toluidine blue (TB) staining using a standard procedure and analyzed by light microscopy to determine histological changes in the tissue structure.

Figure 6:
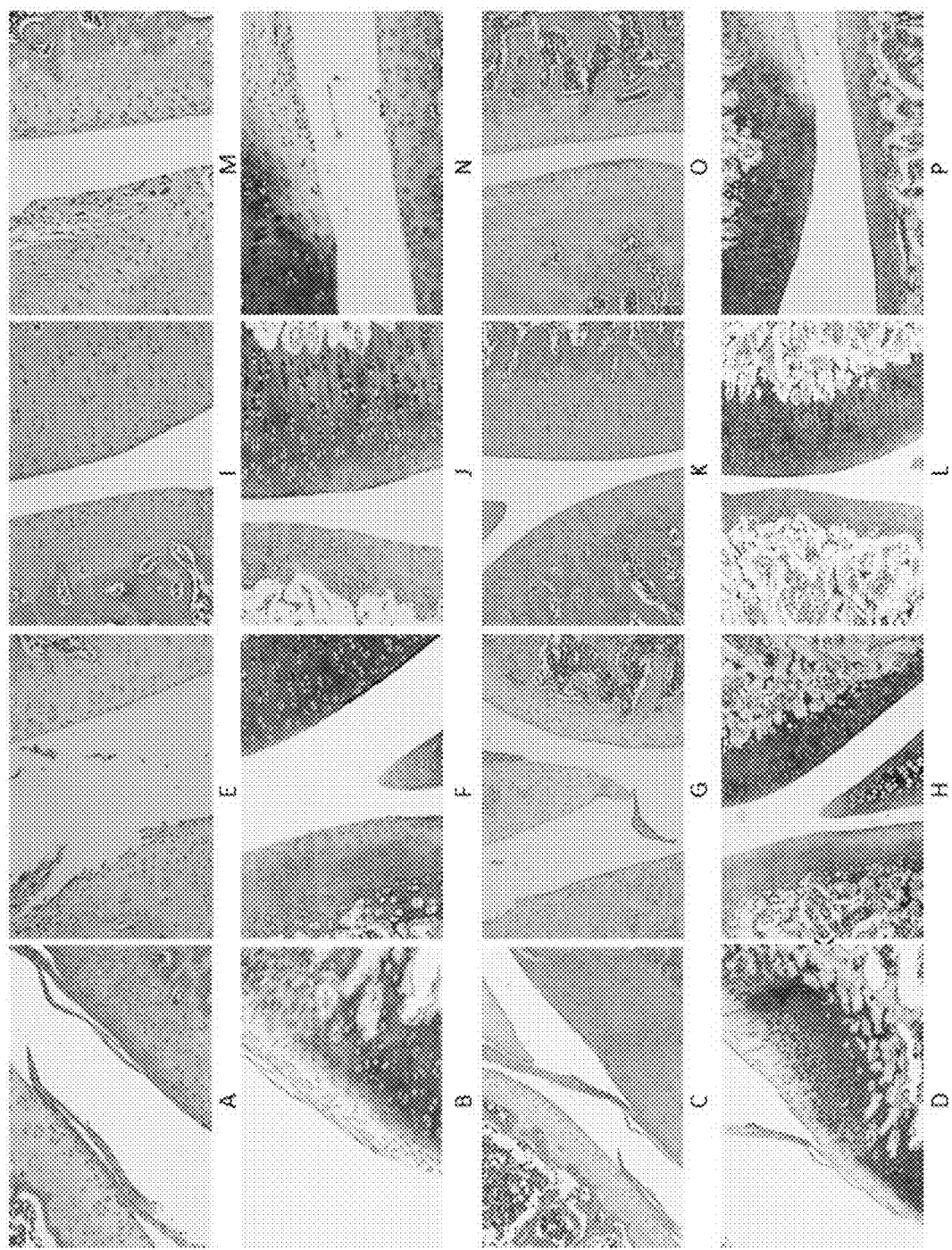
FIG. 6, A-P shows the results of tissue biopsy from a rat model of arthritis treated with certain exemplary siRNAs targeted against ADAMTS-5.

The results are shown in FIG. 6, in which A and B represent HE and TB staining (20×) of the PBS group, C and D represent HE and TB staining (10×) of the PBS group; E and F represent HE and TB staining (20×) of the siRNA-RB-35 group, G and H represent HE and TB staining (10×) of the siRNA-RB-35 group; I and J represent HE and TB staining (20×) of the siRNA-RB-40 group, K and L represent HE and TB staining (10×) of the siRNA-RB-40 group; M and N represent HE and TB staining (20×) of the siRNA-RB-41 group, O and P represent HE and TB staining (10×) the siRNA-RB-41 group.

FIG. 6 demonstrates that after two weeks of administration, the PBS group exhibited the following inflammatory symptoms: ossification at the surface layer of meniscus cartilage and articular cartilage, disordered cartilage cell arrangement and serious collagen loss, finger-like fibrosis projections in the articular cavity, and connective tissue hyperplasia in the articular capsule. Compared with the PBS group, administration of siRNA-RB-40 resulted in smooth articular surfaces, only a small amount of local fibrosis hyperplasia in the joint capsule, and orderly arranged cartilage cells without significant loss of collagen. In the siRNA-RB-35 group, partial collagen loss and articular surface fibrosis occurred, yet the structure of the meniscal and cartilage layers remained intact. The siRNA-RB-41 group maintained smooth articular surfaces and intact cartilage layer structures, with local meniscus and cartilage calcification and no visible fibrosis structure.

The results show that siRNA-RB-40, siRNA-RB-35, and siRNA-RB-41 inhibited the osteoarthritis progression in rats, alleviating various symptoms including, e.g., fibrosis of the articular surface, cartilage erosion, and synovitis. Therefore, the siRNAs described herein may emerge as potential therapeutic agents for treating arthritis diseases.

Example 8

Efficacy of siRNAs in Inhibiting Immune Factors in Rat Joints

The PBS, siRNA-RB-35, siRNA-RB-40, and siRNA-RB-41 groups were established as in Example 7, except that siRNA packaged in chitosan nanoparticles was injected in the siRNA-RB-35 group.

The animals were sacrificed the day after the fourth dose, and knee joints were frozen with liquid nitrogen. RNA was extracted from the knee joints frozen and reverse transcription was carried out using the RNeasy® Mini Kit (QIAGEN). The expression levels of ADAMTS-5 and ADAM17 mRNA were determined using the method in Examples 1 and 9, respectively. The expression levels of TNF, COX-2 and IL-1p were determined using the method in Example 2.

Figure 7:
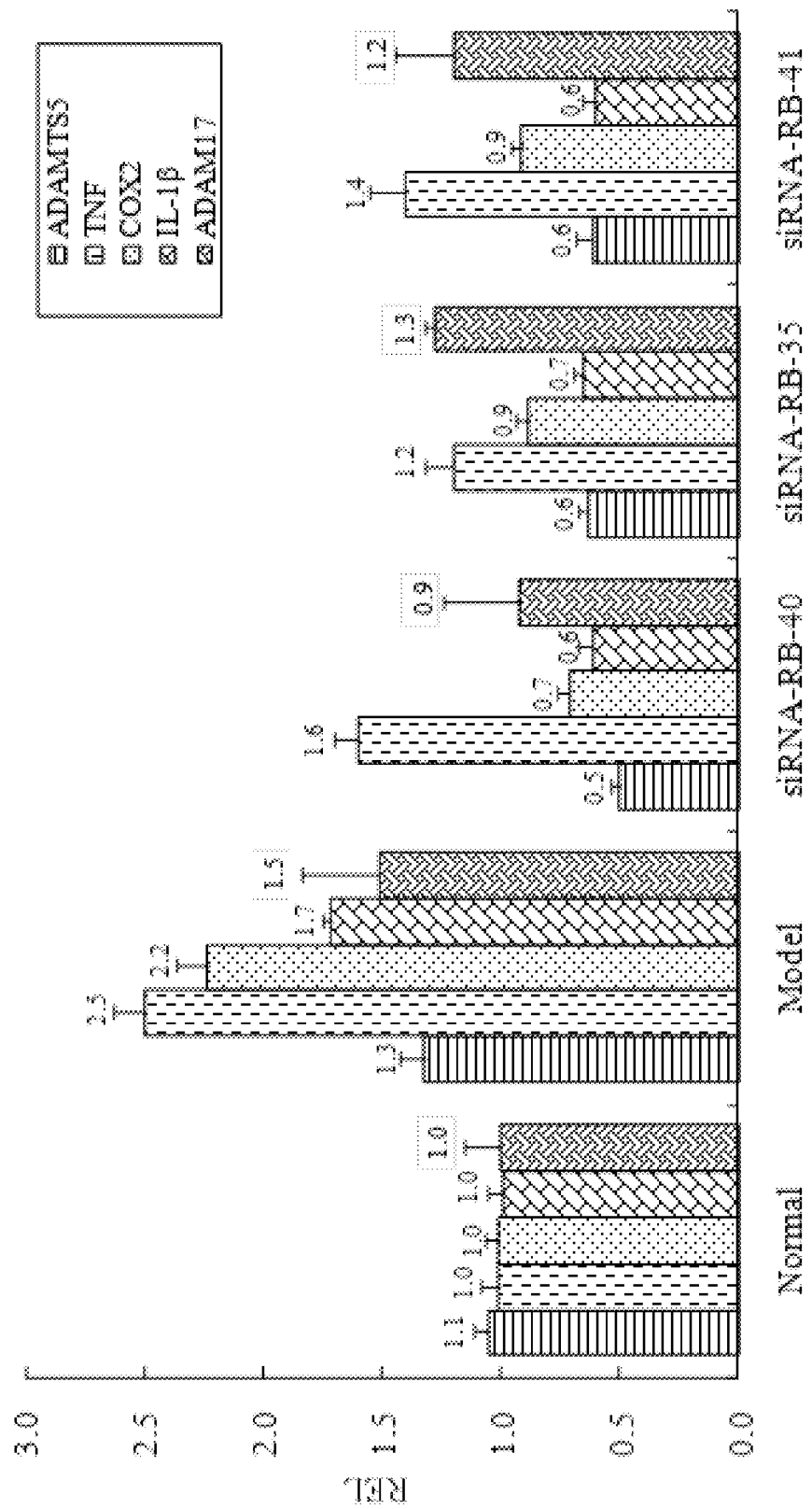
FIG. 7 shows the expression levels of inflammatory cytokines in rat joints treated with certain exemplary siRNAs targeted against ADAMTS-5.

The results are shown in FIG. 7, where "Normal" represents the control group of health male SD rat, and "Model" represents the PBS group. FIG. 7 demonstrates that compared with the normal group, the expression levels of ADAMTS-5, ADAM17, TNF, COX-2, and IL-1β increased in the PBS group. In contrast, siRNA-RB-40, siRNA-RB-35, and siRNA-RB-41 significantly reduced the expression levels of these immune factors, thereby protecting the cartilage and synovial. Based on these results, the siRNAs described herein may be used for effectively preventing and/or treating inflammatory-related diseases.

Example 9

Screening siRNAs for Inhibiting ADAM17 Expression siRNA Design siRNAs targeted against ADAM17 were designed using bioinformatic techniques, for example, BLAST® alignment. The design process used the ADAM17 mRNA sequence in human (Accession No. NM_003183, SEQ ID NO: 194), rat (Accession No. NM_020306, SEQ ID NO: 195), or mouse (Accession No. NM_001277266, SEQ ID NO: 196; NM_001291871, SEQ ID NO: 197; or NM_009615, SEQ ID NO: 198). The specificity of the siRNAs targeted against ADAM17 was ensured as in Example 1. Eight siRNAs capable of inhibiting ADAM17 expression were identified, siRNA-AD-01, siRNA-AD-02, siRNA-AD-03, siRNA-AD-04, siRNA-AD-05, siRNA-AD-06, siRNA-AD-07, and siRNA-AD-08. siRNA Synthesis The siRNAs targeted against ADAM17 were synthesized as in Example 1.

Cell Transfection

The experiment was carried out in ten groups, including no target control group (NTC), negative control group (NC), and eight experimental groups, siRNA-AD-01 to siRNA-AD-08.

The experimental groups: hFLS cells were digested with 0.25% trypsin. Then the cell suspension at a density of $10^4$ cells/ml were seeded in 12-well plates with 500 µl per well. When the hFLS cells were grown to the logarithmic phase (i.e., grown to 80% confluence), siRNAs (50 nM for single dose screen) were transfected into the cells with Lipofectamine® 2000 using the protocol provided by the manufacturer.

The NTC group: The following random non-specific siRNA was used, with the remaining steps unchanged from the experimental groups:

```
Sense strand:
                                    (SEQ ID NO: 185)
5'-AGUAUGCCACAUAAGCAUCdTdT-3'

Antisense strand:
                                    (SEQ ID NO: 186)
5'-GAUGCUUAUGUGGCAUACUdTdT-3'
```

The NC group: No siRNA was transfected, with the remaining steps unchanged from the experimental groups. Quantitative Real-Time PCR (qPCR)

24 hr after transfection, cells were collected by centrifugation at 1000 rpm for 5 min to remove the supernatant. RNA was then extracted using TRIzol®. The extracted RNA was reverse transcribed into cDNA. qPCR was performed using the cDNA as a template and the following ADAM17-F1 and ADAM17-R1 primers. β-actin was used as the reference gene.

```
ADAM17-F1:
                                    (SEQ ID NO: 187)
5'-GGACCAGGGAGGGAAATA-3'

ADAM17-R1:
                                    (SEQ ID NO: 188)
3'-TTGCTGTGGACGACGTTG-5'
```

Figure 8:
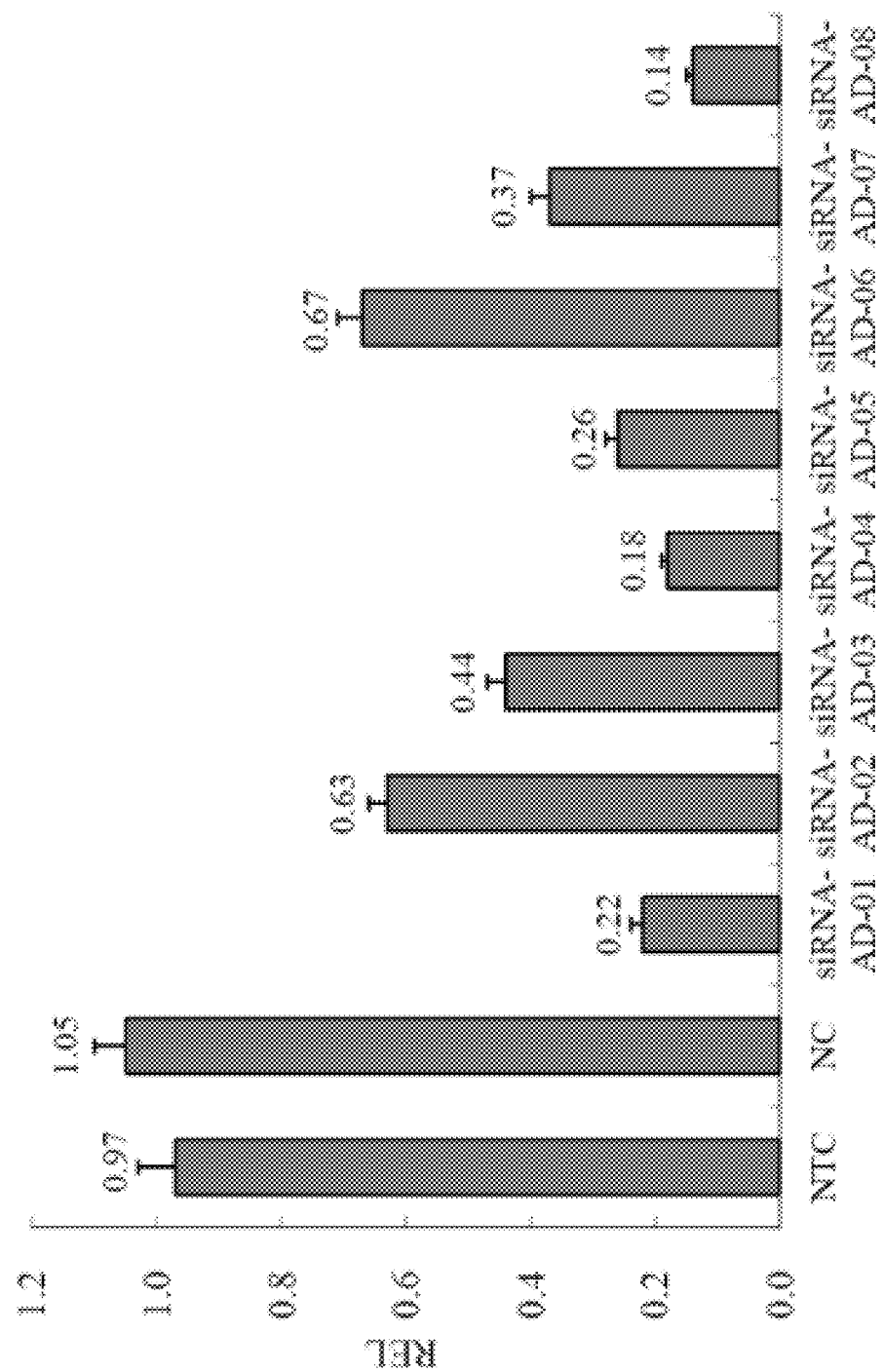
FIG. 8 shows the results of siRNA screening for inhibiting the expression of ADAM17.

FIG. 8 illustrates the inhibition of ADAM17 expression by all of the eight siRNAs. As indicated in FIG. 8, siRNA-AD-08 was the most effective in inhibiting the expression of ADAM17 mRNA in hFLS cells, reducing the expression level by 86%.

The sense and antisense sequences of siRNA-AD-08 are:

```
Sense strand of siRNA-AD-08:
                                    (SEQ ID NO: 7)
5'-GCAUCAUGUAUCUGAACAA-3'

Antisense strand of siRNA-AD-08:
                                    (SEQ ID NO: 8)
5'-UUGUUCAGAUACAUGAUGC-3'
```

Western Blotting

Western blot was performed in the hFLS cells from the siRNA-AD-08, NTC, and NC groups. The cell medium was discarded, and cells were washed with PBS for 2 times. The PBS was then discarded, and an appropriate amount of pre-cooled 2× lysis buffer was added. After the cells were scraped with a cellscraper and subsequently incubated on ice for 30 min, the samples were centrifuged under 4° C. at 12000 g for 15 min. Protein concentration in the supernatant was detected by the Bradford method. After the final concentration of the protein was adjusted to 2 µg/µL, the samples can be stored at −80° C. for future use. 12 µg total protein sample was mixed with an equal volume of 2× loading buffer, incubated in boiling water batch for 10 min, and stored at 4° C. Proteins were separated by gel electrophoresis with 10% SDS-PAGE separation gel and 5% stacking gel. After the electrophoresis, the proteins were transferred to a PVDF membrane at 4° C. with 400 mA currency for 2 hr.

Figure 9:
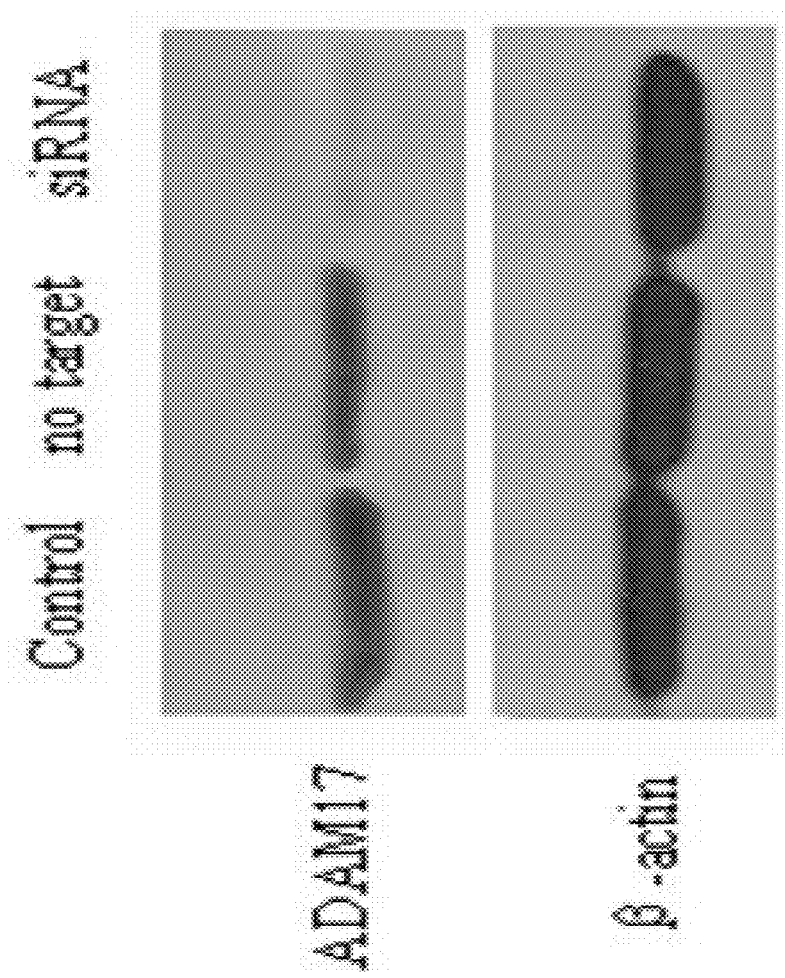
FIG. 9 shows a western blot analysis of siRNA-AD-08.

The results are shown in FIG. 9. "Control" stands for the NC group, "no target" the NTC group, and "siRNA" the siRNA-AD-08 group. FIG. 9 shows that siRNA-AD-08 effectively reduced the expression level of the ADAM17 protein. siRNA-AD-08 was thus taken for subsequent analysis.

$IC_{50}$ Screening $IC_{50}$ (concentration of siRNA resulting in 50% inhibition of ADAM17 mRNA expression compared with untreated control) was determined in hFLS cells transfected with siRNA-AD-08 at the concentrations of 0.01 nM, 0.1 nM, 0.5 nM, 2.5 nM, 25 nM, 50 nM, and 100 nM. The $IC_{50}$ value was calculated by the Origin 8.0 software. siRNA-AD-08 showed an $IC_{50}$ of 0.25 nM. The expression level of ADAM17 mRNA exhibited a siRNA dose-dependent profile, reduced by 26%, 39%, 77%, 84%, 87%, 89%, and 91% at the above concentrations, respectively.

Example 10

Inhibition of Inflammatory Cytokine Expression by siRNAs

The experiment was carried out in the following groups:

hFLS-siRNA-AD-08 experimental groups: Primary hFLS cells were seeded in 6-well plates. When grown to 50% confluence, the cells were transfected with siRNA-AD-08 (50 nM for single dose screen) with Lipofectamine® 2000 using the protocol provided by the manufacturer.

MCF7-siRNA-AD-08 experimental groups: Primary MCF7 cells were seeded in 6-well plates. When grown to 50% confluence, the cells were transfected with siRNA-AD-08 (50 nM for single dose screen) with Lipofectamine® 2000 using the protocol provided by the manufacturer.

hFLS-No target control (NTC) group: hFLS cells were transfected with the following random non-specific siRNA, with the remaining steps unchanged from the hFLS-siRNA-AD-08 group.

```
Sense strand:
                                    (SEQ ID NO: 185)
5'-AGUAUGCCACAUAAGCAUCdTdT-3'

Antisense strand:
                                    (SEQ ID NO: 186)
5'-GAUGCUUAUGUGGCAUACUdTdT-3'
```

(0204) MCF7-No target control (NTC) group: MCF7 cells were transfected with the following random non-specific siRNA, with the remaining steps unchanged from the hFLS-siRNA-AD-08 group.

```
Sense strand:
                                    (SEQ ID NO: 185)
5'-AGUAUGCCACAUAAGCAUCdTdT-3'

Antisense strand:
                                    (SEQ ID NO: 186)
5'-GAUGCUUAUGUGGCAUACUdTdT-3'
``` hFLS-Negative control (NC) group: No siRNA was transfected, with the remaining steps unchanged from the hFLS-siRNA-AD-08 group.

MCF7-Negative control (NC) group: No siRNA was transfected, with the remaining steps unchanged from the MCF7-siRNA-AD-08 group.

24 hr after transfection, cells in each group were cultured in a serum-free medium for starvation cultivation for 24 hr. The cells were stimulated by IL-1α with a final concentration of 10 ng/ml for 24 hr. RNA was extracted, and qPCR was performed with the primers in Example 2 to detect the expression levels of TNF, COX-2 and IL-1β. β-actin was used as the reference gene.

Figure 10A:
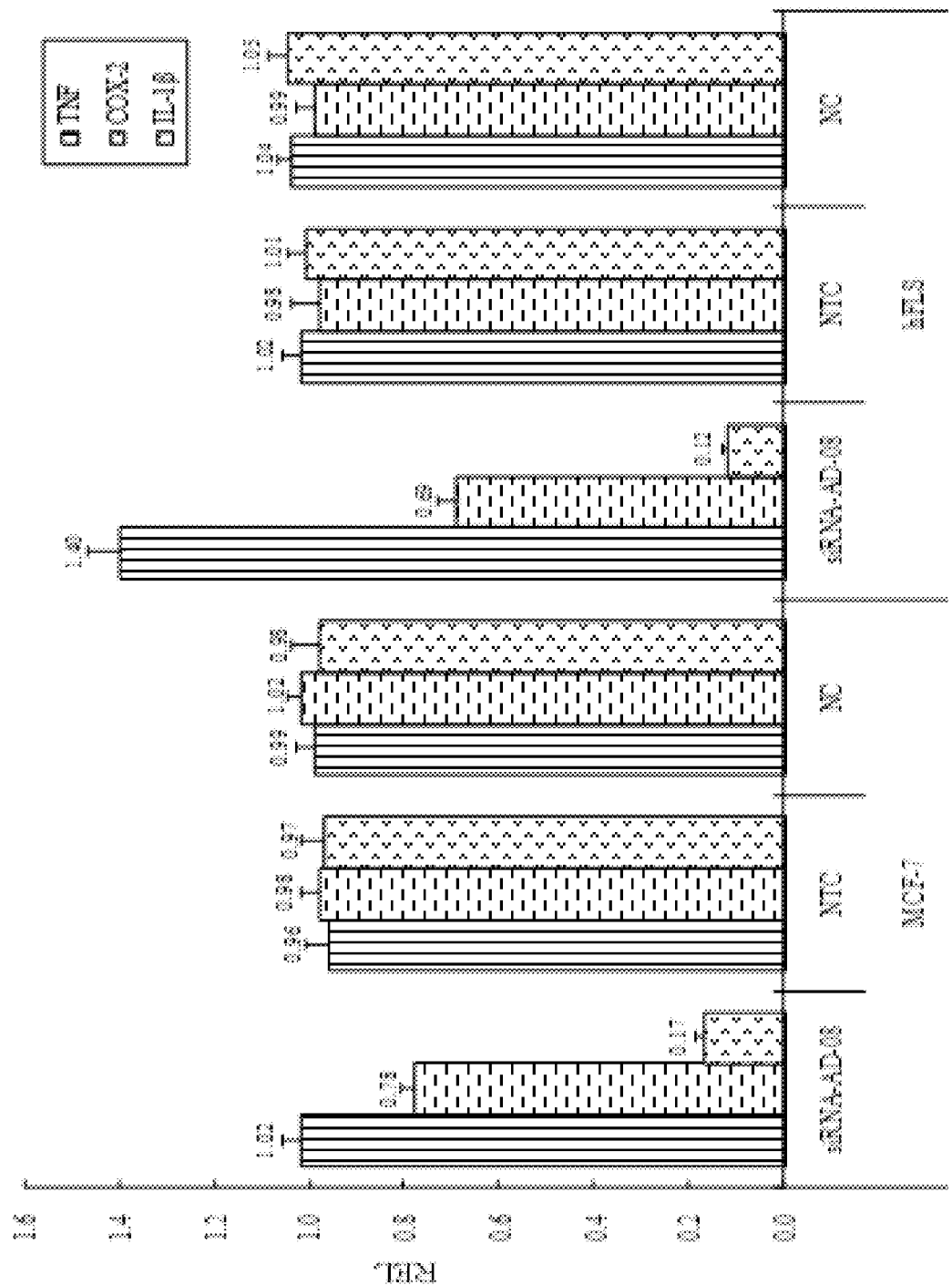
FIG. 10A-10B shows that siRNA-AD-08 down-regulatedcertain inflammatory cytokines.

FIG. 10A shows that siRNA-AD-08 effectively reduced the mRNA expression of COX-2 and IL-1β in hFLS and MCF7 cells. Specifically, the IL-1β expression level in hFLS cells was reduced by 88%. A higher level of TNF in MCF7 cells was observed in the siRNA-AD-08 group than the NTC group, probably because of the complex cellular functions of TNF.

The cell supernatant was collected to detect the levels of secreted IL-1β by AssayMax™ Human IL-1β ELISA Kit. The cells in the NTC groups were further divided as follows:

hFLS-No target control (NTC+) group: hFLS-NTC group treated with IL-1α.

hFLS-No target control (NTC−) group: hFLS-NTC group not treated with IL-1α.

MCF7-No target control (NTC+) group: MCF7-NTC group treated with IL-1α.

MCF7-No target control (NTC−) group: MCF7-NTC group not treated with IL-1α.

Figure 10B:
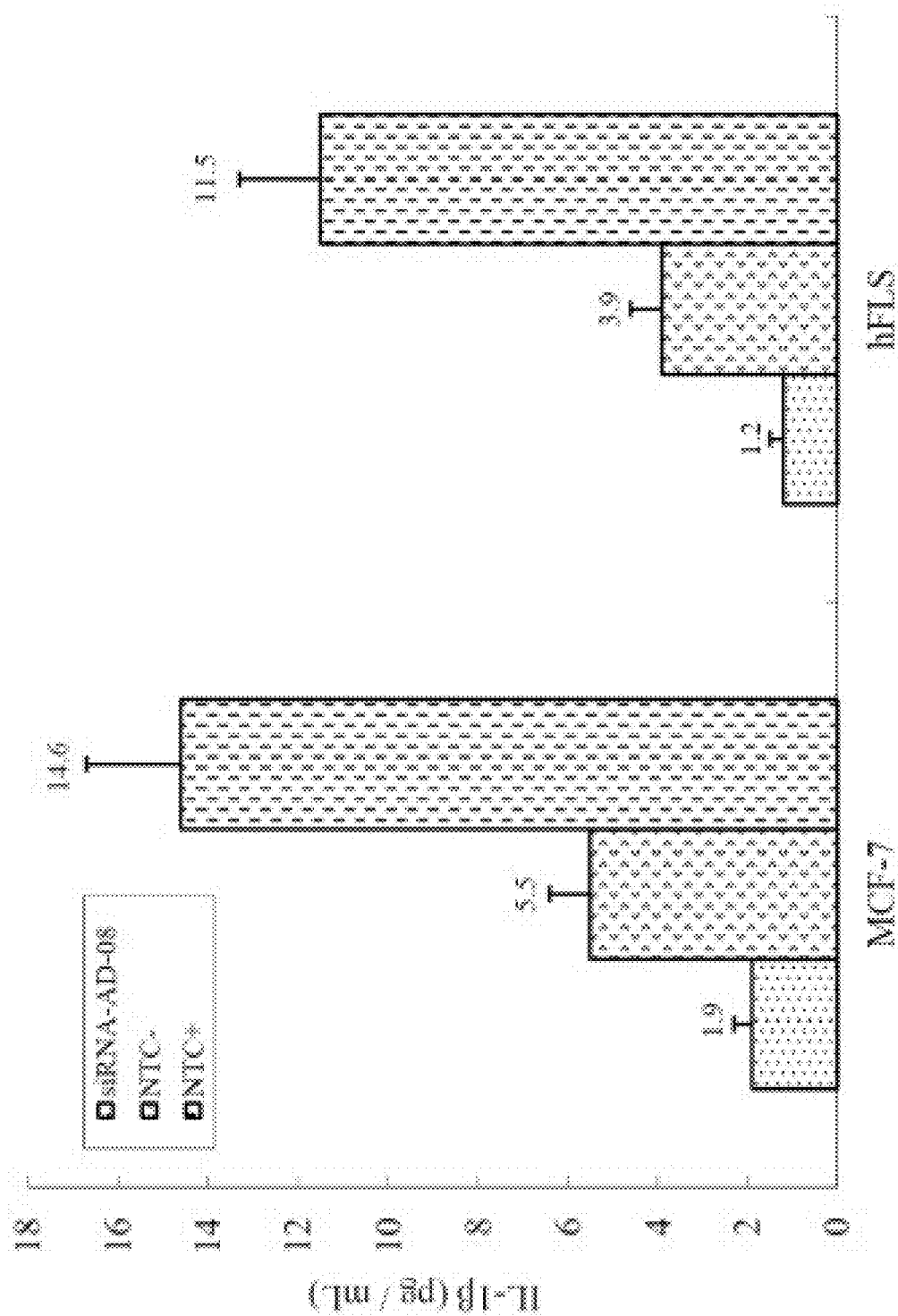

FIG. 10B shows that siRNA-AD-08 inhibited the secretion of the IL-1β protein to a level even lower than that in the unstimulated NTC-groups.

Example 11

Inhibition of ADAM17 by siRNAs with Certain Sequence Identity to siRNA-AD-08

The first set of experiments used siRNAs having the antisense strand of siRNA-AD-08 5'-UUGUUCAGAUA-CAUGAUGC-3' (SEQ ID NO: 8), and a sense strand containing or having certain sequence identity to the sense strand of siRNA-AD-08 5'-GCAUCAU-GUAUCUGAACAA-3' (SEQ ID NO: 7), as shown in Table 8.

TABLE 8

Antisense Group

| siRNA | S (5'→3') | AS (5'→3') | Identity % | REL |
|---|---|---|---|---|
| AD-09 | CAUGUAUCUGA (SEQ ID NO: 98) | UUGUUCAGAUACAUG AUGC (SEQ ID NO: 8) | 58 | 0.46 |
| AD-10 | AUCAUGUAUCUGAAC (SEQ ID NO: 99) | UUGUUCAGAUACAUG AUGC (SEQ ID NO: 8) | 79 | 0.38 |
| AD-11 | UGGCAUCAUGUAUCUGAACA ACG (SEQ ID NO: 100) | UUGUUCAGAUACAUG AUGC (SEQ ID NO: 8) | contain | 0.37 |
| AD-12 | CCUGGCAUCAUGUAUCUGAA CAACGAC (SEQ ID NO: 101) | UUGUUCAGAUACAUG AUGC (SEQ ID NO: 8) | contain | 0.31 |
| AD-14 | AGCA<br>\\/<br>5'GCAUCAUGUAUCUGAACAA3'<br>(SEQ ID NO: 102) | UUGUUCAGAUACAUG AUGC (SEQ ID NO: 8) | contain | 0.39 |
| AD-42 | G*UC*ACAUGUAUCUGAACAA (SEQ ID NO: 103) | UUGUUCAGAUACAUG AUGC (SEQ ID NO: 8) | 84 | 0.41 |
| AD-43 | GC*GUCG*UGUAUCUGAACAA (SEQ ID NO: 104) | UUGUUCAGAUACAUG AUGC (SEQ ID NO: 8) | 89 | 0.36 |
| AD-44 | GCAUCAUGUA*G*CUGAACAA (SEQ ID NO: 105) | UUGUUCAGAUACAUG AUGC (SEQ ID NO: 8) | 95 | 0.28 |
| AD-45 | G*UC*AGA*U*GUA*G*CUGAACAA (SEQ ID NO: 106) | UUGUUCAGAUACAUG AUGC (SEQ ID NO: 8) | 74 | 0.39 |
| AD-46 | A*UC*UGGAGUAUCUGAACAA (SEQ ID NO: 107) | UUGUUCAGAUACAUG AUGC (SEQ ID NO: 8) | 68 | 0.46 |
| AD-47 | AUC*G*UGUAUCUGAAC (SEQ ID NO: 108) | UUGUUCAGAUACAUG AUGC (SEQ ID NO: 8) | 74 | 0.55 |
| AD-60 | GCAUCAUGUAC*C*UGAACAA (SEQ ID NO: 109) | UUGUUCAGAUACAUG AUGC (SEQ ID NO: 8) | 95 | 0.39 |
| AD-61 | CUGA*CG*UCAUGUAUGUGGUC (SEQ ID NO: 110) | UUGUUCAGAUACAUG AUGC (SEQ ID NO: 8) | 68 | 0.42 |

Note:
S = sense strand,
AS = antisense strand,
Italics = mismatches,
REL = relative expression level The second set of experiments used siRNAs having the sense strand of siRNA-AD-08 5'-GCAUCAU-GUAUCUGAACAA-3' (SEQ ID NO: 7), and an antisense strand containing or having certain sequence identity to the antisense strand of siRNA-AD-08 5'-UUGUUCAGAUA-CAUGAUGC-3' (SEQ ID NO: 8), as shown in Table 9.

TABLE 9

Sense Group

| siRNA | S (5'→3') | AS (5'→3') | Identity % | REL |
|---|---|---|---|---|
| AD-15 | GCAUCAUGUAUCUGAA CAA (SEQ ID NO: 7) | UCAGAUACAUG (SEQ ID NO: 111) | 58 | 0.76 |
| AD-16 | GCAUCAUGUAUCUGAA CAA (SEQ ID NO: 7) | GUUCAGAUACAUGAU (SEQ ID NO: 112) | 79 | 0.58 |
| AD-17 | GCAUCAUGUAUCUGAA CAA (SEQ ID NO: 7) | GUCGUUGUUCAGAUACAUG AUGC (SEQ ID NO: 113) | contain | 0.31 |
| AD-18 | GCAUCAUGUAUCUGAA CAA (SEQ ID NO: 7) | GUCGUUGUUCAGAUACAUG AUGCCAGG (SEQ ID NO: 114) | contain | 0.43 |
| AD-19 | GCAUCAUGUAUCUGAA CAA (SEQ ID NO: 7) | 5'-UUGUUCAGAUACAUGAUGC-3'<br>/\\<br>UCUA<br>(SEQ ID NO: 115) | contain | 0.44 |
| AD-48 | GCAUCAUGUAUCUGAA CAA (SEQ ID NO: 7) | UUGUUCAGAUACAUCAUAC (SEQ ID NO: 116) | 89 | 0.43 |
| AD-49 | GCAUCAUGUAUCUGAA CAA (SEQ ID NO: 7) | UUGUUCAGAUACAUCCAAC (SEQ ID NO: 117) | 79 | 0.56 |
| AD-50 | GCAUCAUGUAUCUGAA CAA (SEQ ID NO: 7) | UUGUUCAGAUACAUCCAGC (SEQ ID NO: 118) | 84 | 0.47 |
| AD-51 | GCAUCAUGUAUCUGAA CAA (SEQ ID NO: 7) | UUGUUCAGAUACGUCCAAC (SEQ ID NO: 119) | 74 | 0.54 |
| AD-52 | GCAUCAUGUAUCUGAA CAA (SEQ ID NO: 7) | UUGUUCAGAUACGUCAUGC (SEQ ID NO: 120) | 95 | 0.31 |

TABLE 9-continued

| | Sense Group | | | |
|---|---|---|---|---|
| siRNA | S (5'→3') | AS (5'→3') | Identity % | REL |
| AD-62 | GCAUCAUGUAUCUGAA CAA (SEQ ID NO: 7) | G*C*UCAGAUACAUG*GC*AC (SEQ ID NO: 121) | 68 | 0.65 |

Note:
S = sense strand,
AS = antisense strand,
Italics = mismatches,
REL = relative expression level The third set of experiments used siRNAs having a sense strand containing or having certain sequence identity to the sense strand of siRNA-AD-08 5'-GCAUCAUGUAUCUGAACAA-3' (SEQ ID NO: 7), and an antisense strand containing or having certain sequence identity to the antisense strand of siRNA-AD-08 5'-UUGUUCAGAUACAUGAUGC-3' (SEQ ID NO: 8), as shown in Table 10.

TABLE 10

| | Double Strands Group | | | |
|---|---|---|---|---|
| siRNA | S (5'→3') | AS (5'→3') | Identity % | REL |
| AD-20 | CAUGUAUCUGAdTdT (SEQ ID NO: 122) | UCAGAUACAUGdTdT (SEQ ID NO: 126) | 58 | 0.82 |
| AD-21 | CCUGGCAUCAUGUAUCU GAACAACGACdTdT (SEQ ID NO: 123) | GUCGUUGUUCAGAUACA UGAUGCCAGGdTdT (SEQ ID NO: 127) | contain | 0.61 |
| AD-22 | UGGCAUCAUGUAUCUGA ACAACG (SEQ ID NO: 100) | GUUCAGAUACAUGAU (SEQ ID NO: 112) | contain/79 | 0.59 |
| AD-23 | AUCAUGUAUCUGAAC (SEQ ID NO: 99) | GUCGUUGUUCAGAUACA UGAUGC (SEQ ID NO: 113) | 79/contain | 0.48 |
| AD-24 | 5'GC*A*UCAUGUAUCUGAACAA3' (with AGCA overlay) (SEQ ID NO: 102) | 5'-UUGUUCAGAUACAUGAUGC-3' (with UCUA overlay) (SEQ ID NO: 115) | contain | 0.53 |
| AD-13 | GCAUCAUGUAUCUGAAC AAdTdT (SEQ ID NO: 9) | UUGUUCAGAUACAUGAU GCdTdT (SEQ ID NO: 10) | contain | 0.12 |
| AD-53 | AUCAUGUAUCUGAAC (SEQ ID NO: 99) | GUUCAGAUACAUGAU (SEQ ID NO: 112) | 79 | 0.64 |
| AD-54 | GU*UC*GUGUAUCUGAACA A (SEQ ID NO: 124) | UUGUUCAGAUACAU*C*AU AC (SEQ ID NO: 116) | 89 | 0.53 |
| AD-55 | GU*CA*CAUGUAUCUGAAC AA (SEQ ID NO: 103) | UUGUUCAGAUACGU*C*AU GC (SEQ ID NO: 120) | 84/95 | 0.46 |
| AD-56 | GU*CA*GAUGUAUCUGAAC AA (SEQ ID NO: 125) | UUGUUCAGAUACAUCAU AC (SEQ ID NO: 116) | 79/89 | 0.55 |
| AD-57 | GCAUCAUGUAGCUGAAC AA (SEQ ID NO: 105) | UUGUUCAGAUACGU*C*AU GC (SEQ ID NO: 120) | 95 | 0.35 |
| AD-58 | GCAUCAUGUACCUGAAC AA (SEQ ID NO: 109) | UUGUUCAG*G*UACAUGAU GC (SEQ ID NO: 128) | 95 | 0.49 |
| AD-59 | C*UGACG*UCAUGUAUCUG GUC (SEQ ID NO: 110) | G*C*UCAGAUACAUG*GC*AC (SEQ ID NO: 121) | 68 | 0.76 |

Note:
S = sense strand,
AS = antisense strand,
Italics = mismatches,
REL = relative expression level The siRNAs in Tables 8-10 were each introduced into hFLS cells, and the expression levels of ADAM17 mRNA were detected using the method of Example 8. All of the three sets of experiments used the NTC and NC groups as prepared in Example 8.

As indicated in Tables 8-10, all of the siRNAs in three groups reduced the expression levels of ADAM17 mRNA. The more effective siRNAs included (1) siRNAs having an antisense strand comprising SEQ ID NO: 8, and a sense strand having at least 60% identity to SEQ ID NO: 7; (2) siRNAs having a sense strand comprising SEQ ID NO: 7, and an antisense strand having at least 60% identity to SEQ ID NO: 8; and (3) siRNAs having a sense strand having at least 60% identity to SEQ ID NO: 7, and an antisense strand having at least 60% identity to SEQ ID NO: 8. In particular, 21-nt siRNA-AD-13 having 3' overhang nucleotides reduced the expression level of ADAM17 by 88%.

Example 12

Silencing ADAM17 with siRNA-Encoding Plasmids

A DNA oligonucleotide encoding the sequence of siRNA-AD-08 was designed as shown in Table 11.

TABLE II

DNA Oligonucleotide Encoding siRNA-AD-08

| Sequence (5'→3') number | Sequence of DNA oligonucleotide encoding siRNA-AD-08 |
|---|---|
| SEQ ID NO: 11 | AGCTAAAAATTGTTCAGATACATGATGCTCTCTTGAAGCATC ATGTATCTGAACAAGGG |
| SEQ ID NO: 12 | GATCCCCTTGTTCAGATACATGATGCTTCAAGAGAGCATCA TGTATCTGAACAATTTTT |

The complementary region of the DNA oligonucleotide is underlined. Nucleotides 38-56 (bold) of SEQ ID NO: 11 encode the antisense strand of siRNA-AD-08 (SEQ ID NO: 8). Nucleotides 8-26 (bold) of SEQ ID NO: 12 encode the sense strand of siRNA-AD-08 (SEQ ID NO: 7).

The DNA strands as shown in Table 12 were annealed and cloned into the region between the BamHI and HindIII restriction sites of siRNA expression vector pGCsi-H1/Neo to obtain a recombinant siRNA expression plasmid, Vector 2.

The experiment was conducted in the following groups:

Experimental group: hFLS cells were seeded in 6-well plates one day before transfection. 50 nM Vector 2 was introduced into the hFLS cells with Lipofectamine® 2000 using the protocol provided by the manufacturer. Cells were collected after transfection for 48 hr, and the expression level of ADAM17 mRNA was detected by the method of Example 9.

No target control (NTC) group: DNA encoding the following random non-specific siRNA was cloned into pGCsi-H1/Neo, with the remaining steps unchanged from the experimental group.

Sense strand:
(SEQ ID NO: 185)
5'-AGUAUGCCACAUAAGCAUCdTdT-3'

Antisense strand:
(SEQ ID NO: 186)
5'-GAUGCUUAUGUGGCAUACUdTdT-3'

Negative control (NC) group: The original pGCsi-H1/Neo plasmid without the interference fragment was used, with the remaining steps unchanged from the experimental group. The results are shown in Table 12.

TABLE 12

| Relative Expression Levels of ADAM17 | | |
|---|---|---|
| Experimental group | NC group | NTC group |
| 0.25 ± 0.02 | 1.12 ± 0.08 | 1.07 ± 0.05 |

Table 12 demonstrates that transfection of DNA encoding siRNA-AD-08 also effectively silenced ADAM17.

Example 13

Silencing of ADAM17 by Chemically-Modified siRNAs siRNA-AD-13 was subjected to various types or combinations of chemical modifications as shown in Tables 6 and 14 to further increase the stability and interference effect of the siRNA molecules.

TABLE 13

Silencing of ADAM17 by Chemically-modified siRNAs

| Modification | siRNA | Strand | siRNA sequence (5'→3') | REL |
|---|---|---|---|---|
| none | AD-13 | S | GCAUCAUGUAUCUGAACAA dTdT (SEQ ID NO: 9) | 0.12 ± 0.01 |
| | | AS | UUGUUCAGAUACAUGAUGC dTdT (SEQ ID NO: 10) | |
| thiophosphoric acid | AD-25 | S | GsCsAsUCAUGUAUCUGAACsAsAs dTdT (SEQ ID NO: 129) | 0.16 ± 0.03 |
| | | AS | UsUsGsUUCAGAUACAUGAUsGsCs dTdT (SEQ ID NO: 130) | |
| cholesterol | AD-26 | S | Chol-GCAUCAUGUAUCUGAACAA dTdT (SEQ ID NO: 131) | 0.10 ± 0.01 |
| | | AS | UUGUUCAGAUACAUGAUGCdTdT (SEQ ID NO: 132) | |
| 2'-OMe | AD-27 | S | GmCmAmUCAUGUAUCUGAACmAm AmdTdT (SEQ ID NO: 133) | 0.15 ± 0.01 |
| | | AS | UmUmGmUUCAGAUACAUGAUm GmCm dTdT (SEQ ID NO: 134) | |

TABLE 13-continued

Silencing of ADAM17 by Chemically-modified siRNAs

| Modification | siRNA | Strand | siRNA sequence (5'→3') | REL |
|---|---|---|---|---|
| 2'-F | AD-28 | S | GfCfAfUCAUGUAUCUGAACfAfAf dTdT (SEQ ID NO: 135) | 0.21 ± 0.03 |
| | | AS | UfUfGfUUCAGAUACAUGAUfGfCf dTdT (SEQ ID NO: 136) | |
| LNA | AD-29 | S | GCAUCAUGUAUCUGAACAAdTdT (SEQ ID NO: 137) | 0.31 ± 0.02 |
| | | AS | UUGUUCAGAUACAUGAUGCdTdT (SEQ ID NO: 138) | |
| UNA | AD-30 | S | GCAUCAUGUAUCUGAACAAdTdT (SEQ ID NO: 139) | 0.36 ± 0.03 |
| | | AS | UnUGUUCAGAUACAUGAUGCdTdT (SEQ ID NO: 140) | |
| indole | AD-31 | S | GiCiAiUCAUGUAUCUGAACiAiAi dTdT (SEQ ID NO: 141) | 0.39 ± 0.03 |
| | | AS | UiUiGiUUCAGAUACAUGAUiGiCi dTdT (SEQ ID NO: 142) | |
| 5-methylcytosine | AD-32 | S | GCAUCAUGUAUCUGAACAAdTdT (SEQ ID NO: 143) | 0.33 ± 0.02 |
| | | AS | UUGUUCAGAUACAUGAUGCdTdT (SEQ ID NO: 144) | |
| 5-ethynyluracil | AD-33 | S | GCAUCAUGUAUCUGAACAAdTdT (SEQ ID NO: 145) | 0.51 ± 0.02 |
| | | AS | UUGUUCAGAUACAUGAUGCdTdT (SEQ ID NO: 146) | |
| galactose, 2'-OMe | AD-34 | S | GmCmAmUCAUGUAUCUGAACmAm Am dTdT- Gal (SEQ ID NO: 147) | 0.19 ± 0.03 |
| | | AS | UmUmGmUUCAGAUACAUGAUm GmCm dTdT (SEQ ID NO: 148) | |
| phosphorylation, 2'-OMe | AD-35 | S | GmCmAmUCAUGUAUCUGAACmAm AmdTdT (SEQ ID NO: 149) | 0.13 ± 0.01 |
| | | AS | p-UmUmGmUUCAGAUACAUGAUm GmCmdTdT (SEQ ID NO: 150) | |
| 2'-OMe, polypeptide | AD-36 | S | Pep-GmCmAmUCAUGUAUCUGAA CmAmAmdTdT (SEQ ID NO: 151) | 0.21 ± 0.03 |
| | | AS | UmUmGmUUCAGAUACAUGAUm GmCmdTdT (SEQ ID NO: 152) | |
| 2'-OMe, Cy | AD-37 | S | Cy-GmCmAmUCAUGUAUCUGAA CmAmAmdTdT (SEQ ID NO: 153) | 0.23 ± 0.02 |
| | | AS | UmUmGmUUCAGAUACAUGAUm GmCmdTdT (SEQ ID NO: 154) | |
| 2'-OMe, thiophosphoric acid | AD-38 | S | GmsCmsAmsUCAUGUAUCUGAA CmsAmsAmsdTdT (SEQ ID NO: 155) | 0.15 ± 0.02 |
| | | AS | UmsUmsGmsUUCAGAUACAUGA UmsGmsCmsdTdT (SEQ ID NO: 156) | |
| 2'-OMe, cholesterol | AD-39 | S | Chol-GmCmAmUCAUGUAUCUGAA CmAmAmdTdT (SEQ ID NO: 157) | 0.11 ± 0.01 |
| | | AS | UmUmGmUUCAGAUACAUGAUm GmCmdTdT (SEQ ID NO: 158) | |
| 2'-OMe, cholesterol, phosphorylation | AD-40 | S | Chol-GmCmAmUCAUGUAUCUGAA CmAmAmdTdT (SEQ ID NO: 159) | 0.10 ± 0.01 |
| | | AS | p-UmUmGmUUCAGAUACAUGAUm GmCmdTdT (SEQ ID NO: 160) | |
| 2'-OMe, thiophosphoric acid, cholesterol, phosphorylation | AD-41 | S | Chol-GmsCmsAmsUCAUGUAUCUGA ACmsAmsAmsdTdT (SEQ ID NO: 161) | 0.12 ± 0.02 |
| | | AS | p-UmsUmsGmsUUCAGAUACAUGA UmsGmsCmsdTdT (SEQ ID NO: 162) | |
| 5-methylcytosine, 2'-OMe | AD-58 | S | GmCAmUCAUGUAUCUGAACAmA dTdT (SEQ ID NO: 163) | 0.21 ± 0.05 |
| | | AS | UmUGmUUCAGAUACAUGAUmGmC dTdT (SEQ ID NO: 164) | |
| 2'-OMe, biotinylation | AD-59 | S | Bio-GmCmAmUCAUGUAUCUGAA CmAAmdTdT (SEQ ID NO: 165) | 0.27 ± 0.05 |
| | | AS | UmUGmUUCAGAUACAUGAUmGm CmdTdT (SEQ ID NO: 166) | |
| 2'-OMe, 2'-F | AD-60 | S | GCAUCAUGUAUCUGAACAA (SEQ ID NO: 167) | 0.23 ± 0.04 |
| | | AS | UfUfGfUUCAGAUACAUGAUmGm Cm (SEQ ID NO: 168) | |
| 2'-OMe, 2'-F | AD-61 | S | GfCmAfUmCAUGUAUCUGAACfAAf (SEQ ID NO: 169) | 0.19 ± 0.02 |
| | | AS | UUfGUUCAGfAUACAUGAfUGfC (SEQ ID NO: 170) | |

TABLE 13-continued

Silencing of ADAM17 by Chemically-modified siRNAs

| Modification | siRNA | Strand | siRNA sequence (5'→3') | REL |
|---|---|---|---|---|
| thiophosphoric acid, 2'-OMe | AD-62 | S | GCmAUmCAUmGUmAUmCUmGAA CmAAdTsdT (SEQ ID NO: 171) | 0.17 ± 0.03 |
| | | AS | UmUGUmUCmAGAUACAUmGAUm GCmdTsdT (SEQ ID NO: 172) | |
| thiophosphoric acid, 2'-OMe | AD-63 | S | GmCmAUCAUGUAUCUGAACmAsA (SEQ ID NO: 173) | 0.24 ± 0.04 |
| | | AS | UUGUUmCAGAUACAUGAUGCCms A (SEQ ID NO: 174) | |

Note:
S = sense strand,
AS = antisense strand,
REL = relative expression level

Chemically-modified siRNA as shown in Table 13 were transfected into hFLS cells, and the expression levels of ADAM17 mRNA were determined by the method of Example 9. Where siRNAs modified with cholesterol, polypeptides, or galactose were used, no transfection reagent was added.

The results in Table 13 show that siRNA-AD-13 and siRNA-AD-08 with appropriate chemical modifications effectively silenced ADAM17.

Example 14

Stabilization of siRNAs in Serum by Chemical Modifications

Serum stability of the chemically-modified siRNAs in example 13 was determined as follows: equal volume fresh rat serum was added into 5 µM siRNAs diluted by RNAase-free water. The mixture was incubated at 37° C. for 30 min and subjected to electrophoresis to check the integrity of the siRNAs.

Figure 11:
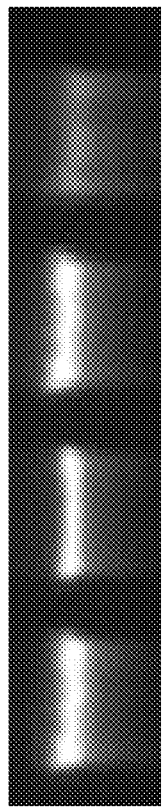
FIG. 11 shows that certain chemical modifications enhanced the stability of certain exemplary siRNAs targeting against ADAM17 in the serum.

As shown in FIG. 11, after 30 min incubation in rat serum, a significantly amount of unmodified siRNA-AD-13 was degraded, while the chemically-modified molecules siRNA-AD-26, siRNA-AD-39, and siRNA-AD-40 exhibited no sign of degradation.

Example 15

Efficacy of siRNAs in Treating Rat Model of Arthritis

A rat model of arthritis was constructed as in example 7

3 d after the injection of bovine type II collagen, the arthritic rats were randomly divided into four groups with eight rats in each group as follows: PBS group, injected with 100 PBS control, and siRNA-AD-26, siRNA-AD-40, and siRNA-AD-39 experimental groups, injected with 10 nmol siRNA solution (100 µL) at 50 µL per leg. The control or siRNA was administered to each group twice a week for two weeks.

Four rats from each group were sacrificed the day after the fourth administration, and knee joints were fixed in a tissue preservation solution for hematoxylin-eosin (HE) or toluidine blue (TB) staining using a standard procedure and analyzed by light microscopy to determine histological changes in the tissue structure.

Figure 12:
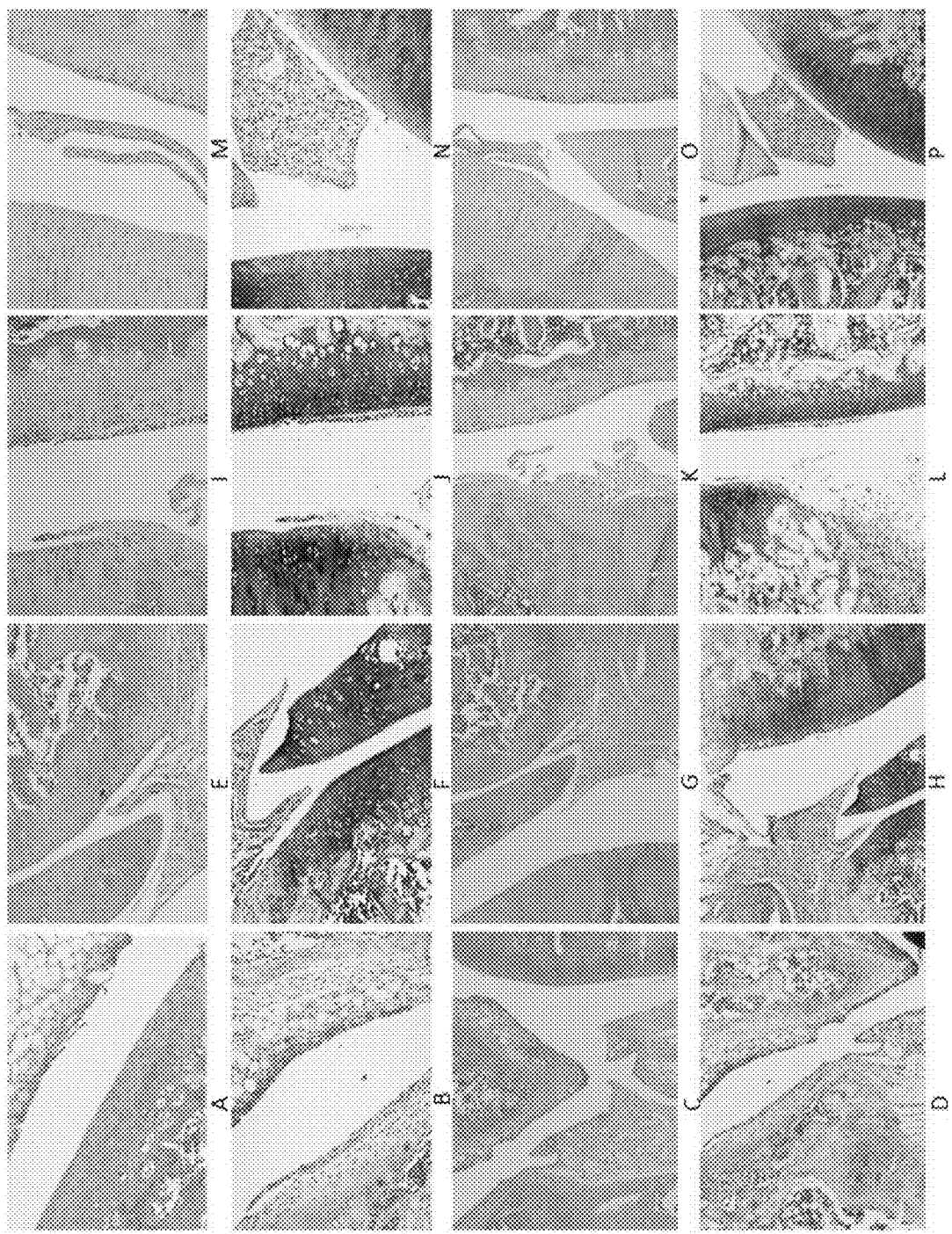
FIG. 12, A-P shows the results of tissue biopsy from a rat model of arthritis treated with certain exemplary siRNAs targeted against ADAM17.

The results are shown in FIG. 12, in which A and B represent HE and TB staining (20×) of the PBS group, C and D represent HE and TB staining (10×) of the PBS group; E and F represent HE and TB staining (20×) of the siRNA-AD-40 group, G and H represent HE and TB staining (10×) of the siRNA-AD-40 group; I and J represent HE and TB staining (20×) of the siRNA-AD-26 group, K and L represent HE and TB staining (10×) of the siRNA-AD-26 group; M and N represent HE and TB staining (20×) of the siRNA-AD-39 group, 0 and P represent HE and TB staining (10×) the siRNA-AD-39 group.

FIG. 12 demonstrates that after two weeks of administration, the PBS group exhibited the following inflammatory symptoms: a high level of fibrosis in the articular cavity and surface, meniscus ossification, disordered cartilage cells, and significant loss of collagen. Compared with the PBS group, administration of siRNA-AD-40 resulted in ossificated but normally shaped meniscus, smooth articular surfaces, local ossification and fibrosis, orderly arranged cartilage cells, and local loss of collagen. In the siRNA-AD-26 group, meniscus ossification and local collagen loss occurred, but the articular cavity remained clear. The siRNA-AD-39 group showed smooth articular surfaces, a small amount of fibrosis in the joint cavity, local meniscus and cartilage ossification, orderly arranged cartilage cells, and only partial loss of collagen.

The results demonstrate that siRNA-AD-26, siRNA-AD-39, and siRNA-AD-40 inhibited the disease progression in the arthritic rats. Therefore, the siRNAs described herein may emerge as potential therapeutic agents for treating arthritis diseases.

Example 16

Efficacy of siRNAs in Inhibiting Immune Factors in Rat Joints

The PBS, siRNA-AD-26, siRNA-AD-39, and siRNA-AD-40 groups were established as in Example 15, except that siRNA packaged in chitosan nanoparticles was injected in the siRNA-AD-41 group.

The animals were sacrificed the day after the fourth dose, and knee joints were frozen with liquid nitrogen. RNA was extracted from the knee joints frozen and reverse transcription was carried out using the RNeasy® Mini Kit (QIAGEN). The expression levels of ADAMTS-5 and ADAM17 mRNA were determined using the method in Examples 1 and 9, respectively. The expression levels of TNF, COX-2 and IL-1β were determined using the method in Example 10.

Figure 13:
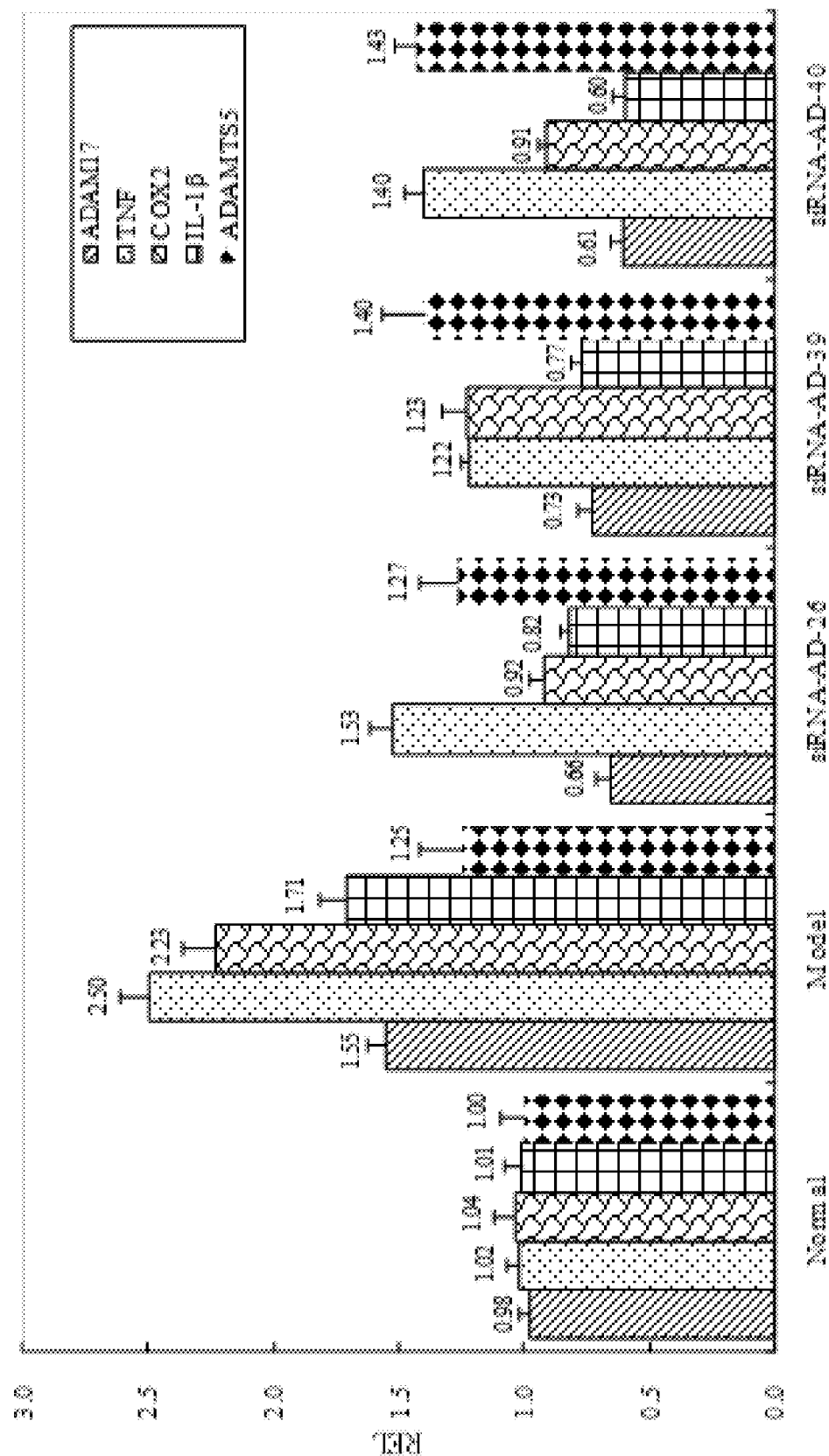
FIG. 13 the expression levels of inflammatory cytokines in rat joints treated with certain exemplary siRNAs targeted against ADAM17.

The results are shown in FIG. 13, where "Normal" represents the control group of health male SD rat, and "Model" represents the PBS group. FIG. 13 demonstrates that compared with the normal group, the expression levels of ADAMTS-5, ADAM17, TNF, COX-2, and IL-1β increased in the PBS group. In contrast, siRNA-AD-40, siRNA-AD-39, and siRNA-AD-26 significantly reduced the expression levels of these immune factors, thereby protecting the cartilage and synovial. Based on these results, the siRNAs described herein may be used for effectively preventing and/or treating inflammatory-related diseases.

Example 17

Efficacy of Long-Term Administration of siRNAs

The PBS group, the single-dose siRNA-AD-40 group (single dose, expression levels examined 1.5 or 3 weeks following dosing), and the long-term siRNA-AD-40 (long-term administration, once every 0.5 weeks for 1.5 or 3 weeks) groups were established as in Example 16. The expression levels of ADAM17 mRNA were determined using the method in Example 9. The expression levels of TNF, COX-2 and IL-1β were determined using the method in Example 10.

Figure 14A:
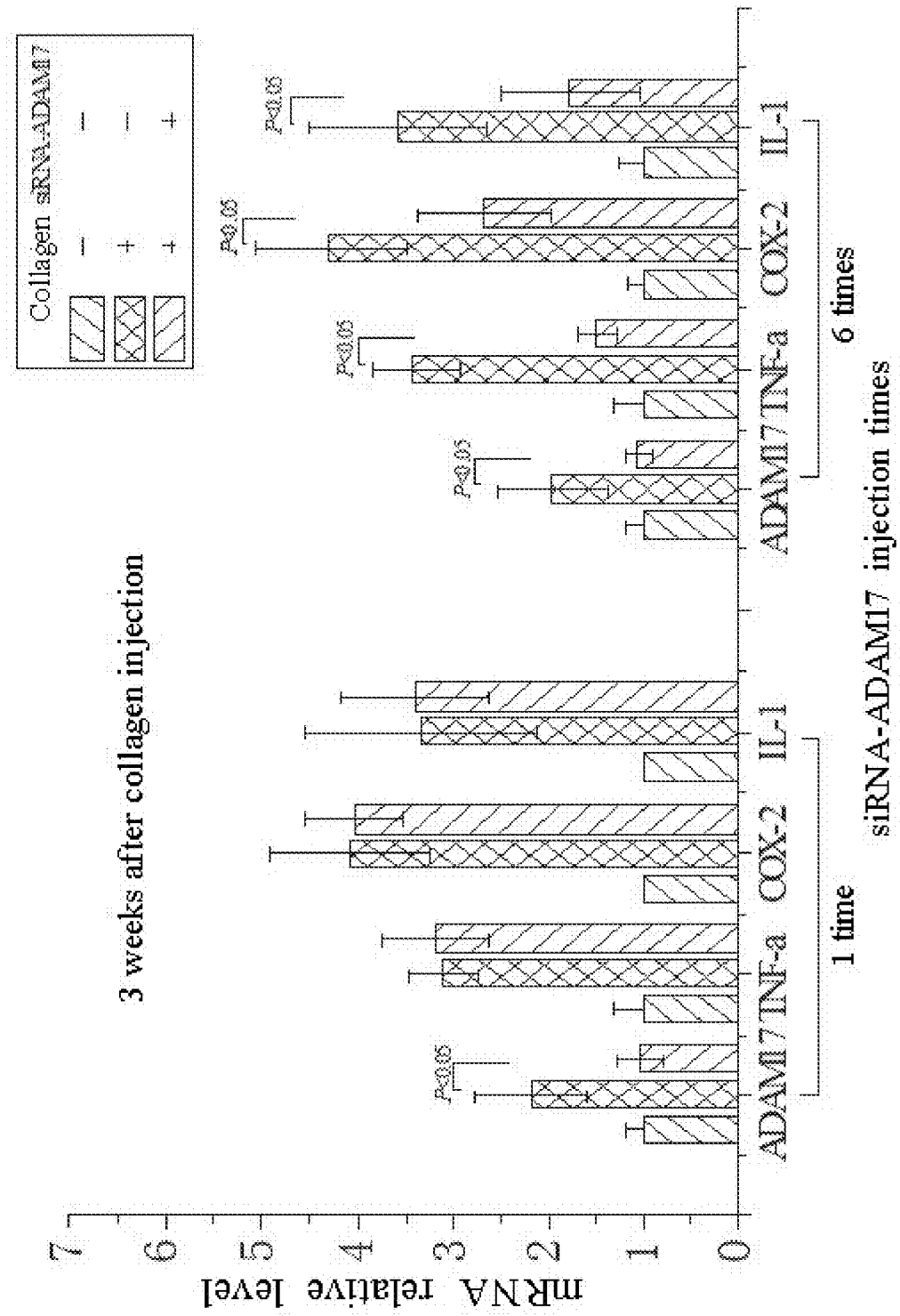
FIG. 14A-14B shows the results of long-term administration of certain exemplary siRNAs targeted against ADAM-17.
Figure 14B:
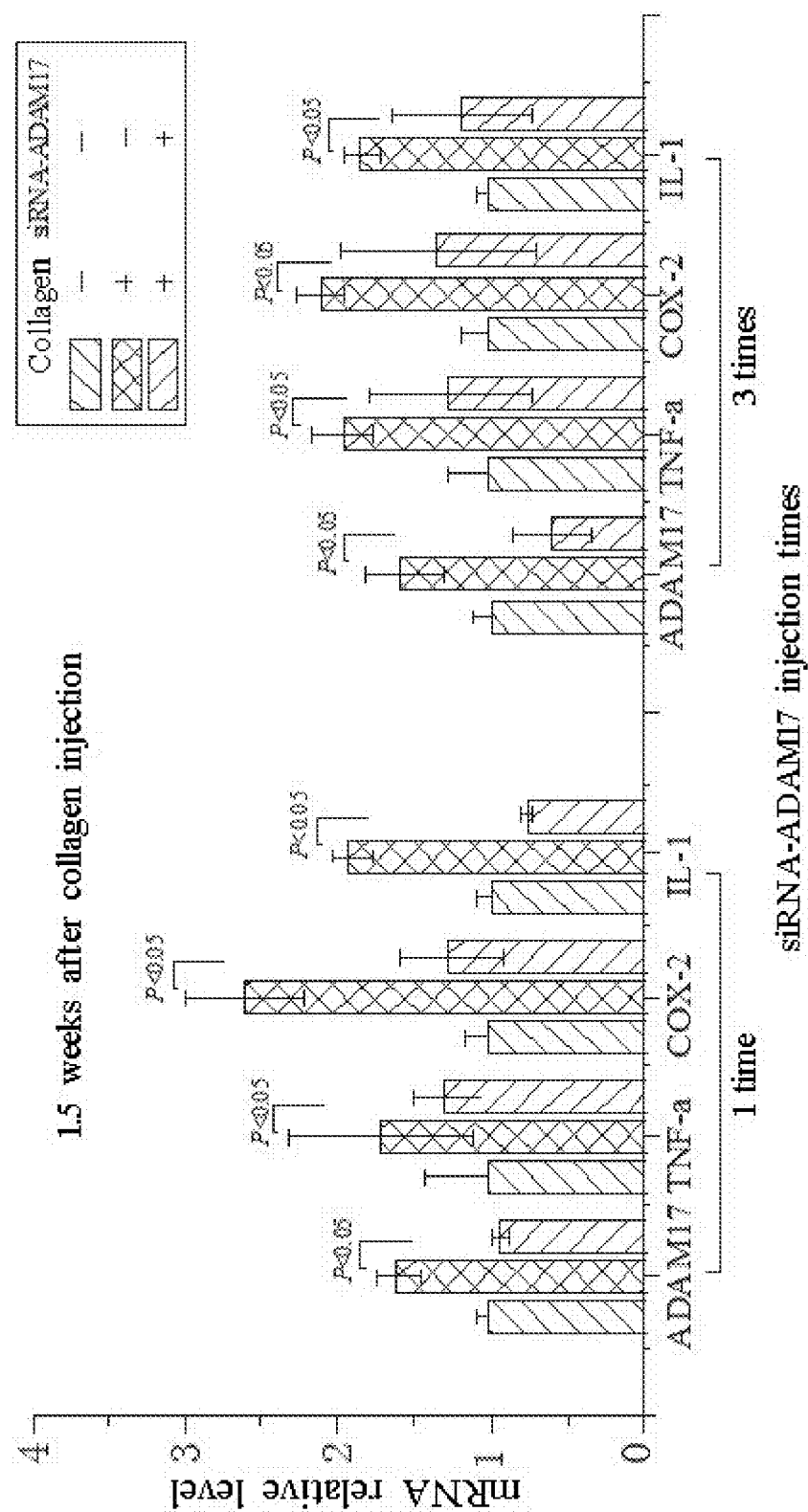

As shown in FIG. 14B, the single-dose treatment and long-term treatment for 1.5 weeks exhibited similar efficacy in inhibiting the expression levels of immune factors. Under both dosing regimens, the expression levels of ADAM17, TNF, COX-2, and IL-1β were reduced. In contrast, as shown in FIG. 14A, long-term administration had a better inhibitory effect when the treatment was extended to three weeks.

Example 18

Inhibition of Inflammatory Cytokines with Combination of siRNAs

ADAMTS-5+ADAM17 group: Primary hFLS cells were seeded in 6-well plates. When grown to 50% confluence, the cells were transfected with 25 nM siRNA-RB-β and 25 nM siRNA-AD-13 using Lipofectaminer® 2000 according to the protocol provided by the manufacturer.

ADAMTS-5 group: hFLS cells were transfected with 50 nM siRNA-RB-13, with the remaining steps unchanged from the ADAMTS-5+ADAM17 group.

ADAM17 group: hFLS cells were transfected with 50 nM siRNA-AD-13, with the remaining steps unchanged from the ADAMTS-5+ADAM17 group.

No target control (NTC) group: hFLS cells were transfected with the following random non-specific siRNA, with the remaining steps unchanged from the ADAMTS-5+ADAM17 group.

```
Sense:
                                    (SEQ ID NO: 189)
5'-UUCUCCGAACGUGUCACGUdTdT-3'

Antisense:
                                    (SEQ ID NO: 190)
5'-ACGUGACACGUUCGGAGAAdTdT-3'
```

Negative control (NC) group: No siRNA was transfected, with the remaining steps unchanged from the ADAMTS-5+ADAM17 group.

24 hr after transfection, the cells in each group were cultured in a serum-free medium for starvation cultivation for 24 hr and stimulated with IL-1α at a final concentration of 10 ng/ml for about 24 hr. The levels of secreted IL-1β were determined as in Example 2.

Figure 15:
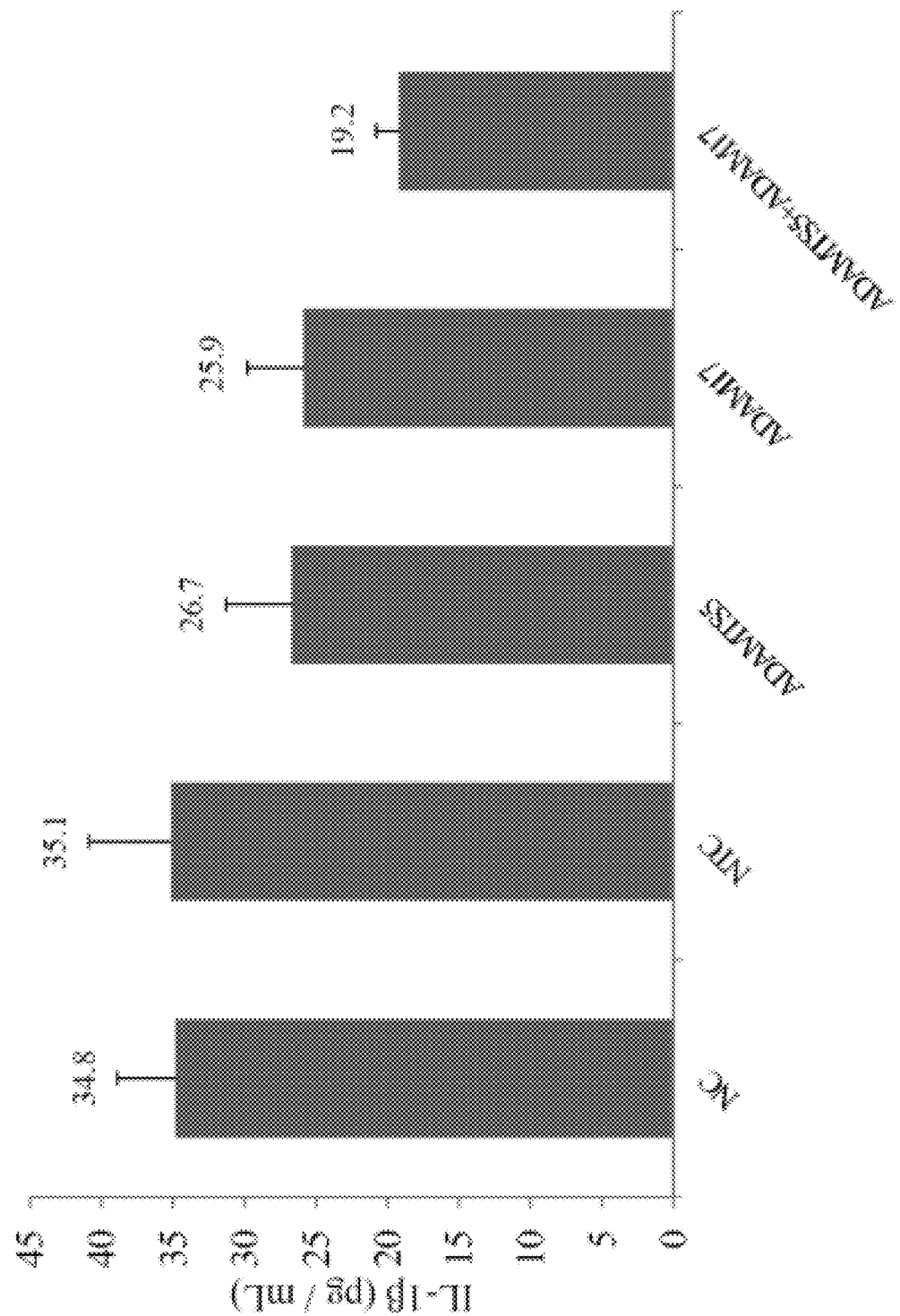
FIG. 15 shows that a combination of certain exemplary siRNAs targeted against ADAMTS-5 and ADAM-17 reduced the expression levels of certain inflammatory cytokines.

The results in FIG. 15 shows that compared with the single siRNA groups, the co-administration of siRNA-RB-13 and siRNA-AD-13 significantly enhanced the inhibitory effect on secreted IL-1l1.

Example 19

Efficacy of siRNA Combination in Treating Rat Model of Arthritis

A rat model of arthritis was constructed as in example 7.

3 d after the injection of bovine type II collagen, twelve arthritic rats were each injected with 100 μl PBS in one hind leg as the control group, and 10 nmol siRNA-RB-40 and 10 nmol siRNA-AD-26 at a total volume of 100 μL in the other hind leg as the AD5&17 group. Dosing was twice a week for three weeks. Animals were sacrificed the day after the second, fourth, and sixth doses, respectively. Knee joints were taken and fixed in a tissue preservation solution for hematoxylin-eosin (HE) or toluidine blue (TB) staining using a standard procedure and analyzed by light microscopy to determine histological changes in the tissue structure.

Figure 16A:
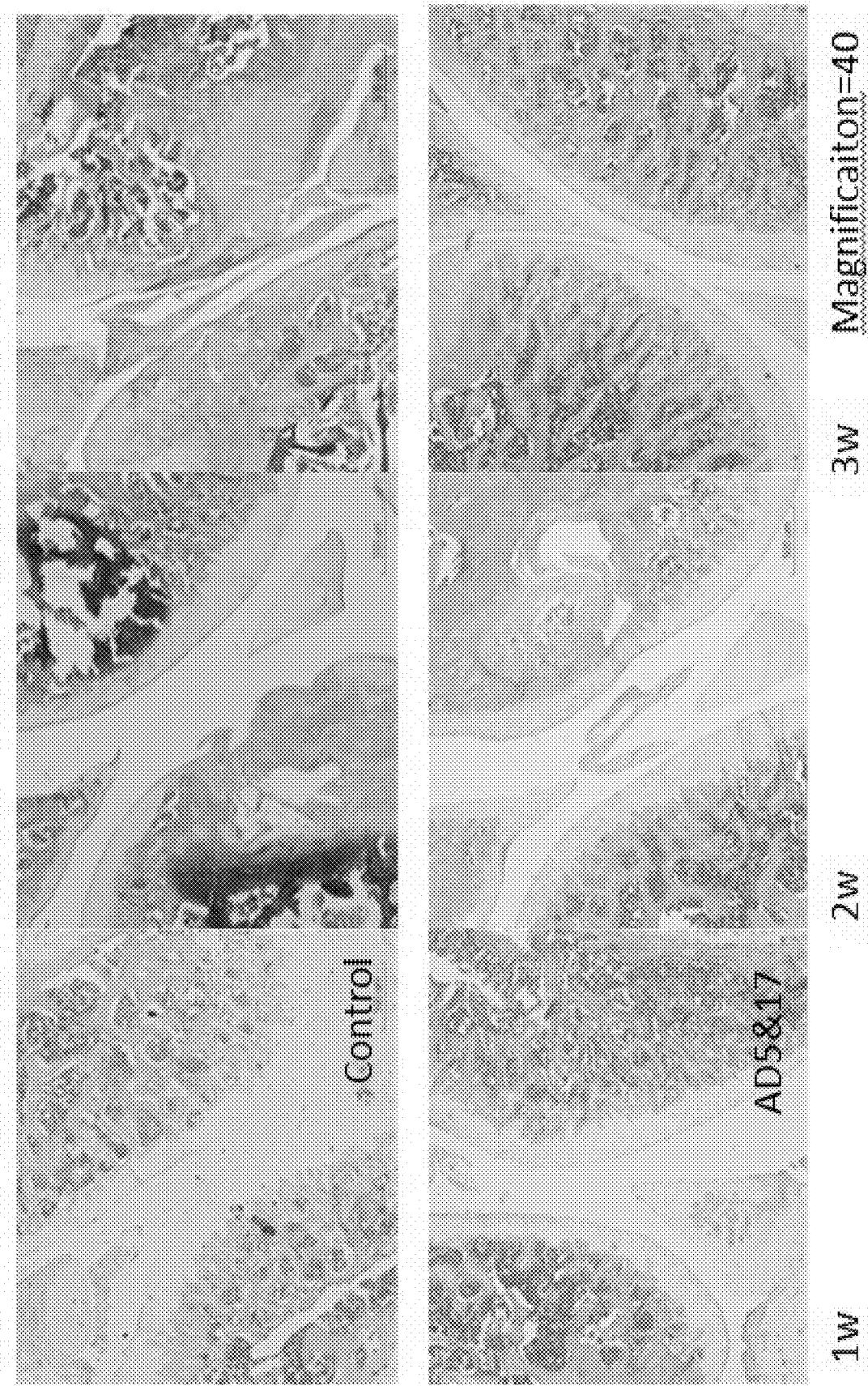
FIG. 16A-16B shows the results of tissue biopsy from a rat model of arthritis treated with a combination of certain targeted against ADAM-17 siRNAs targeted against ADAMTS-5 and ADAM17.
Figure 16B:
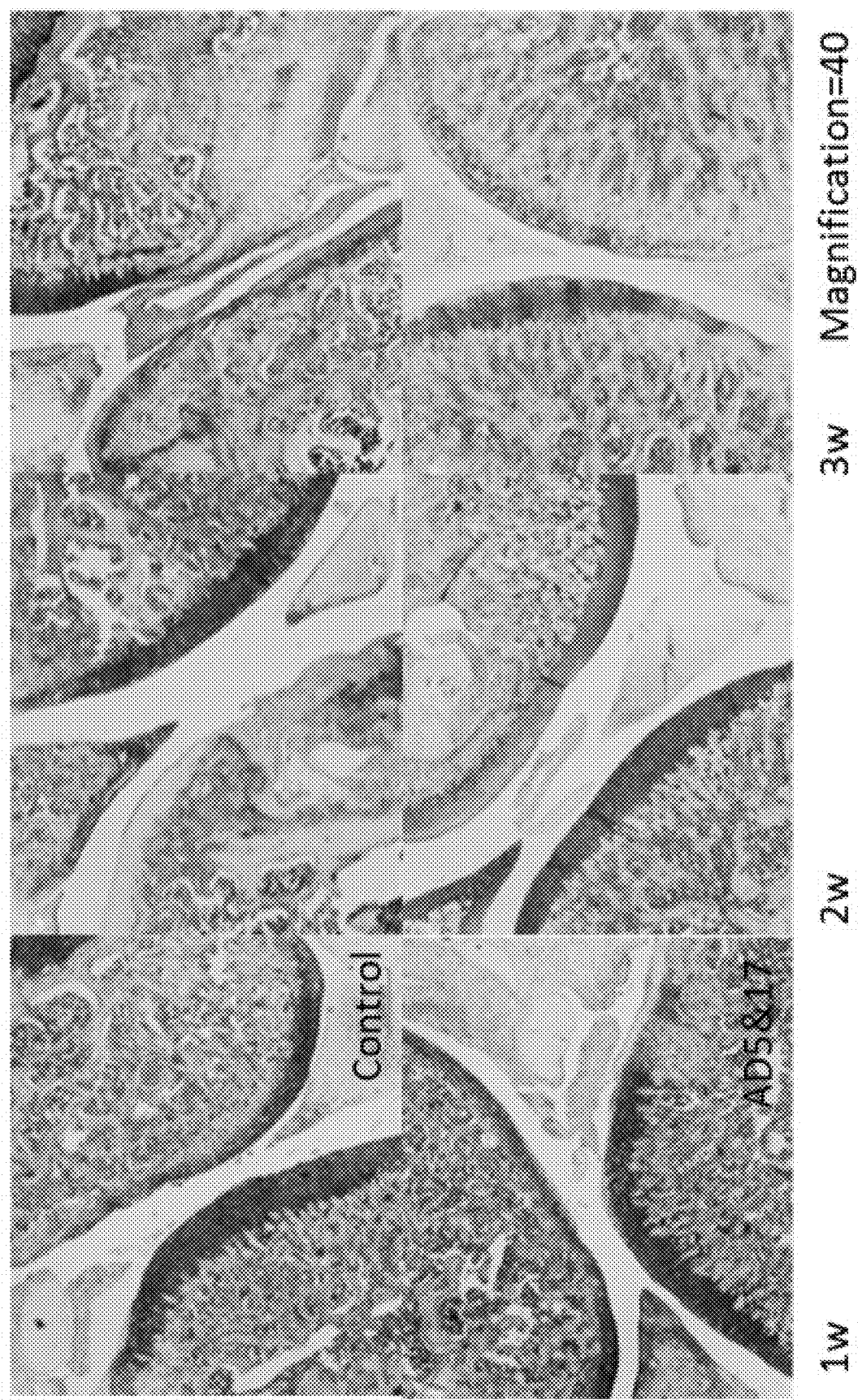

The results of HE and TB staining are shown in FIGS. 16A and 16B, respectively. One week after modeling, the control group exhibited disordered arrangement of cartilage cells, thickening of the articular cartilage, meniscus ossification, and cartilage collagen loss. In contrast, cartilage collagen loss was not obvious in the AD5&17 group, with only slight meniscus ossification. Two weeks after modeling, local fibrosis occurred in the subchondral bone of the control group, and fibrosis hyperplasia was observed in cartilage layers near the joint cavity and synovium, accompanied by serious loss of collagen, severe fibrosis of the joint capsule, and meniscus ossification. The AD5&17 group, however, showed only slight loss of local cartilage collagen. Three weeks after modeling, severe fibrosis of the articular surface, debris in the joint cavity, and serious infiltration of inflammatory cells occurred in control group. Yet the AD5&17 group maintained smooth articular surfaces and active cartilage cells. Thus, the AD5&17 group exhibited lighter pathological changes than the control group, indicating that the combination of AD5&17 siRNAs can inhibit the arthritic progression in rats.

Example 20

Efficacy of siRNA Combination in Inhibiting Immune Factors in Rat Joints

The ADAMTS-5-siRNA & ADAM17-siRNA group was established using the method of Example 7, with siRNA-RB-40 and siRNA-AD-26 each dosed at 5 nmol per leg, twice a week. The arthritis model group was constructed as in Example 7 and injected with PBS with the same dosing. The healthy rats group used male SD rats (220±20 g).

The animals were sacrificed the day after the second, fourth, and sixth dose, respectively, and the knee joints were frozen with liquid nitrogen. RNA was extracted from the knee joints frozen and reverse transcription was carried out using the RNeasy® Mini Kit (QIAGEN). The expression levels of ADAMTS-5 and ADAM17 mRNA were determined using the method in Examples 1 and 9, respectively. The expression levels of TNF, COX-2 and IL-1D were determined using the method in Example 2. The results are shown in Table 14.

TABLE 14

Expression of Immune factors in Rat Joints Treated
by Combination of ADAMTS-5 and ADAM17 siRNAs

| | Gene | Healthy rats | Arthritic rats | ADAMTS-5-siRNA & ADAM17-siRNA |
|---|---|---|---|---|
| 1 w | ADAM 17 | 1.02 ± 0.06 | 1.41 ± 0.13 | 0.60 ± 0.05 |
| | ADAMTS-5 | 0.99 ± 0.06 | 1.76 ± 0.09 | 0.53 ± 0.04 |
| | TNFα | 1.03 ± 0.05 | 2.12 ± 0.14 | 0.64 ± 0.04 |
| | COX2 | 1.02 ± 0.04 | 2.03 ± 0.13 | 0.82 ± 0.05 |
| | IL-1β | 0.96 ± 0.07 | 1.81 ± 0.16 | 0.47 ± 0.06 |
| 2 w | ADAM 17 | 1.02 ± 0.08 | 1.72 ± 0.10 | 0.54 ± 0.05 |
| | ADAMTS-5 | 0.99 ± 0.05 | 1.33 ± 0.12 | 0.52 ± 0.07 |
| | TNFα | 1.05 ± 0.06 | 2.21 ± 0.15 | 1.20 ± 0.09 |
| | COX2 | 1.03 ± 0.05 | 2.10 ± 0.14 | 0.93 ± 0.08 |
| | IL-1β | 0.97 ± 0.07 | 1.92 ± 0.16 | 0.55 ± 0.03 |
| 3 w | ADAM17 | 1.05 ± 0.04 | 2.15 ± 0.12 | 1.06 ± 0.06 |
| | ADAMTS-5 | 1.07 ± 0.06 | 1.15 ± 0.13 | 0.57 ± 0.06 |
| | TNFα | 1.02 ± 0.04 | 3.22 ± 0.17 | 1.21 ± 0.04 |
| | COX2 | 1.05 ± 0.05 | 3.87 ± 0.15 | 1.48 ± 0.11 |
| | IL-1β | 1.01 ± 0.07 | 3.38 ± 0.15 | 1.17 ± 0.07 |

Compared with the healthy rats group, the expression levels of ADAMTS-5, ADAM17, TNF, COX-2, and IL-1β increased in the arthritis model group, whereas the combination group showed notable gene silencing from 1-3 weeks after administration. Thus, combination therapy using ADAMTS-5 and ADAM17 siRNAs may treat inflammation-related diseases with high efficacy.

Example 21

Toxicity Test (Data Not Shown)

To evaluate the toxic effects of various concentrations of siRNAs on normal rats, one group of healthy male SD rats (220±20 g) received intravenous tail vein injection, and the other group received local articular injection. The injection volume was 0.2 ml for both groups. The intravenous injection group was further divided into a PBS subgroup and 10 nmol, 50 nmol, and 100 nmol siRNA subgroups, each with six rats. A combination of siRNA-RB-40 and siRNA-AD-26, each siRNA at 10 nmol, 50 nmol, or 100 nmol, was injected in the three siRNA subgroups, respectively. The local articular injection group was similarly divided into four subgroups, each with nine rats. Dosing was twice a week.

In the intravenous injection group, animals were weighed before administration and killed three weeks later. In the local articular injection group, three animals in each subgroup were sacrificed at the third day after the second, fourth, and sixth doses, respectively, for pathological analysis and biochemical tests. All of the animals in the intravenous injection group survived the experiment without significant weight loss. The local articular injection group also survived, showing no abnormal behavior or significant fibrosis.

Example 22

Effects of Pre-administered siRNAs (Data Not Shown)

Each knee joint of 45 healthy male SD rats (220±20 g) was pre-treated with a combination of siRNA-RB-40 and siRNA-AD-26, each siRNA at 10 nmol, 50 nmol, or 100 nmol, and then given 0.2 ml bovine collagen II (2 mg/ml) to stimulate OA at a predetermined time. Animals were sacrificed three days after the collagen stimulation.

10 nmol Group: Pretreatment at 3 and 5 days before collagen stimulation showed a protective effect compared with an arthritis model group injected with PBS. Pre-administration of the siRNAs resulted in slight knee injuries, intact and orderly arranged cartilage cells, no significant fibrosis or proliferation of synovial layers, intact meniscus. Pretreatment at 8 and 12 days before collagen stimulation showed similar symptoms as the model group, including obvious fibrosis injuries, partial or entire meniscus damage, fibrosis hyperplasia in articular surfaces, disordered cartilage cells, and local ossification.

50 nmol and 100 nmol Groups: Pretreatment at 3 and 8 days before collagen stimulation provided protection against collagen-induced injuries. Rats pretreated at 3 days before collagen stimulation had similar results to a normal group of healthy male SD rats without collagen stimulation. Those pretreated at 8 days before collagen stimulation showed slight meniscus damage and ossification, fibrosis hyperplasia in periarticular connective tissues, but intact and smooth articular surfaces, orderly arranged cartilage cells, and local chondrocytes ossification. Pretreatment at 12 days before collagen stimulation had similar symptoms as the model group.

Thus, siRNA treatment before the onset of OA may have protective effects, depending on the timing of the pretreatment.

What is claimed is:

1. A pharmaceutical composition comprising at least one siRNA targeted against ADAMTS-5, and at least one siRNA targeted against ADAM17, and optionally a pharmaceutically acceptable carrier, wherein the sense strand of the double-stranded siRNA targeted against ADAMTS-5 comprises a nucleotide sequence of SEQ ID NO: 3, and the antisense strand of double-stranded siRNA targeted against ADAMTS-5 comprises a nucleotide sequence of SEQ ID NO: 4, and wherein the sense strand of the double-stranded siRNA targeted against ADAM17 comprises a nucleotide sequence of SEQ ID NO: 7, and the antisense strand of the double-stranded siRNA targeted against ADAM17 comprises a nucleotide sequence of SEQ ID NO: 8.

2. The pharmaceutical composition of claim 1, wherein the at least one strand of the siRNA comprises at least one chemical modification chosen from end modifications, base modifications, sugar modifications, and backbone modifications.

3. The pharmaceutical composition of claim 2, wherein the sense strand comprises the nucleotide sequence selected from SEQ ID NO: 3 and SEQ ID NO: 9; and the antisense strand molecule comprises the nucleotide sequence selected from SEQ ID NO: 4 and SEQ ID NO: 10.

4. The pharmaceutical composition of claim 2, wherein at least one strand of the siRNA comprises at least one chemical modification chosen from:

(a) a phosphorothioate modification in the phosphate backbone;
(b) 2'-O-methyl modification in a ribose or deoxyribose;
(c) 2'-deoxy-2'-fluoro modification in a ribose or deoxyribose;
(d) a locked nucleic acid (LNA) modification;
(e) an open-loop nucleic acid modification;
(f) an indole modification;
(g) a 5-methylcytosine modification in a base;
(h) a 5-ethynyluracil modification in a base;
(i) a terminal nucleotide linked to a cholesteryl derivative;
(j) a terminal nucleotide linked to a galactose;
(k) a terminal nucleotide linked to a polypeptide;
(l) a phosphorylation modification;
(m) a terminal nucleotide linked to a fluorescent marker; and
(n) a terminal nucleotide linked to a biotin molecule.

5. The pharmaceutical composition of claim 4, wherein the sense strand comprises the nucleotide sequence 5'-K-LLMUUUAUGUGGGCAUPMQdTdT-3' (SEQ ID NO: 13), and the antisense strand comprises the nucleotide sequence 5'-R-MQLAUGCCCACAUAAAQPPdTdT-3' (SEQ ID NO: 14), wherein:

K is an optional cholesterol group linked to a 5'-end nucleotide;

R is an optional phosphorylation modification on a 5'-end nucleotide;

dT is a thymine deoxyribonucleotide;

L is an unmodified or 2'-O-methyl modified guanine deoxyribonucleotide;

M is an unmodified or 2'-O-methyl modified adenine deoxyribonucleotides;

P is an unmodified or 2'-O-methyl modified cytosine deoxyribonucleotide; and

Q is an unmodified or 2'-O-methyl modified uracil ribonucleotide; and optionally, at least one of L, M, P, and Q has a phosphorothioate backbone;

or, wherein the sense strand comprises the nucleotide sequence 5'-K'-L'P'M'UCAUGUAUCUGAAP'M-'M'dTdT-3' (SEQ ID NO: 15), and the antisense strand comprises the nucleotide sequence 5'-R'-Q' Q'L'UUCAGAUACAU GAQ'L'P'dTdT-3' (SEQ ID NO: 16), wherein:

K' is an optional cholesterol group linked to a 5'-end nucleotide;

R' is an optional phosphorylation modification on a 5'-end nucleotide;

dT is a thymine deoxyribonucleotide;

L' is an unmodified or 2'-O-methyl modified guanine deoxyribonucleotide;

M' is an unmodified or 2'-O-methyl modified adenine deoxyribonucleotides;

P' is an unmodified or 2'-O-methyl modified cytosine deoxyribonucleotide; and

Q' is an unmodified or 2'-O-methyl modified uracil ribonucleotide; and optionally, at least one of L', M', P', and Q' has a phosphorothioate backbone.

6. The pharmaceutical composition of claim 1, wherein the sense strand comprises a sense sequence chosen from Table 7 or 13, and the antisense strand comprises an antisense sequence chosen from Table 7 or 13.

7. The pharmaceutical composition of claim 6, wherein the sense strand comprises a sense sequence selected from SEQ ID NO: 80 and SEQ ID NO: 159, and the antisense strand comprises an antisense sequence selected from SEQ ID NO: 81 and SEQ ID NO: 160.

* * * * *